United States Patent
Chan-Hui et al.

(10) Patent No.: US 7,402,397 B2
(45) Date of Patent: *Jul. 22, 2008

(54) DETECTING AND PROFILING MOLECULAR COMPLEXES

(75) Inventors: Po-Ying Chan-Hui, Oakland, CA (US); Sharat Singh, Los Altos, CA (US); Hossein Salimi-Moosavi, Sunnyvale, CA (US); Hasan Tahir, Foster City, CA (US); Gerald J. Wallweber, La Honda, CA (US); Hrair Kirakosssian, San Jose, CA (US); Tracy J. Matray, Campbell, CA (US)

(73) Assignee: Monogram BioSciences, Inc., South San Francisco, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 10/916,291

(22) Filed: Aug. 10, 2004

(65) Prior Publication Data
US 2005/0079565 A1 Apr. 14, 2005

Related U.S. Application Data

(63) Continuation-in-part of application No. 10/623,057, filed on Jul. 17, 2003, now Pat. No. 7,105,308, and a continuation-in-part of application No. 10/154,042, filed on May 21, 2002, now Pat. No. 7,255,999.

(60) Provisional application No. 60/512,941, filed on Oct. 20, 2003, provisional application No. 60/508,034, filed on Oct. 1, 2003, provisional application No. 60/494,482, filed on Aug. 11, 2003.

(51) Int. Cl.
*G01N 33/53* (2006.01)
*G01N 33/532* (2006.01)
*G01N 33/554* (2006.01)
*C07K 1/10* (2006.01)
*C07K 1/14* (2006.01)

(52) U.S. Cl. .......... 435/7.1; 436/544; 436/546; 436/161; 436/824; 530/402; 530/412

(58) Field of Classification Search .......... 435/7.1, 435/9.92; 530/388.9, 402, 412; 436/544, 436/546, 161, 824
See application file for complete search history.

(56) References Cited

U.S. PATENT DOCUMENTS 4,331,590 A 5/1982 Bocuslaski .......... 260/112 B (Continued)

FOREIGN PATENT DOCUMENTS

EP 0 484 027 5/1992

(Continued)

OTHER PUBLICATIONS

Agus, et al., "Targeting ligand-activated ErbB2 signaling inhibits breast and prostate tumor growth", Cancer Cell, 2002, 2:127-137.

(Continued)

*Primary Examiner*—Long V. Le
*Assistant Examiner*—Shafiqul Haq
(74) *Attorney, Agent, or Firm*—Fenwick & West LLP

(57) ABSTRACT

Methods are provided for detecting the formation of complexes of molecules, especially proteins, in a sample, such as a cell or tissue lysate. In one aspect, a cleaving probe specific for a first protein in a complex and one or more binding compounds specific for one or more second proteins in a complex are provided. Upon binding, the cleaving probe is induced to generate an active species, such as singlet oxygen, that cleaves molecular tags attached to the binding compounds only in the local region of the cleaving probe. The released molecular tags are separated from the assay mixture and from one another to provide a readout that is related to the number and types of proteins present in the complex.

10 Claims, 38 Drawing Sheets

U.S. PATENT DOCUMENTS

| | | | |
|---|---|---|---|
| 4,650,750 A | 3/1987 | Giese | 435/7 |
| 4,709,016 A | 11/1987 | Giese | 530/389 |
| 4,772,550 A | 9/1988 | Greenquist | 435/7 |
| 4,780,421 A | 10/1988 | Kameda | 436/518 |
| 4,891,324 A | 1/1990 | Pease | 436/519 |
| 4,968,603 A | 11/1990 | Slamon | 435/6 |
| 5,057,412 A | 10/1991 | Rabin | 435/6 |
| 5,108,896 A | 4/1992 | Philo | 435/7.5 |
| 5,137,609 A | 8/1992 | Manian | |
| 5,192,660 A | 3/1993 | Reed-Gitomer | 435/7.21 |
| 5,340,716 A | 8/1994 | Ullman | 435/6 |
| 5,360,819 A | 11/1994 | Giese | 514/538 |
| 5,436,128 A | 7/1995 | Harpold | 435/6 |
| 5,470,705 A | 11/1995 | Grossman | 435/6 |
| 5,480,968 A | 1/1996 | Kraus | 530/326 |
| 5,494,793 A | 2/1996 | Schindele | 435/6 |
| 5,514,543 A | 5/1996 | Grossman | 435/6 |
| 5,516,636 A | 5/1996 | McCapra | 435/6 |
| 5,516,931 A | 5/1996 | Giese | 560/59 |
| 5,536,834 A | 7/1996 | Singh | 544/98 |
| 5,565,324 A | 10/1996 | Still | 435/6 |
| 5,571,680 A | 11/1996 | Chen | |
| 5,578,498 A | 11/1996 | Singh | 436/518 |
| 5,580,732 A | 12/1996 | Grossman | 435/6 |
| 5,602,273 A | 2/1997 | Giese | 560/60 |
| 5,604,104 A | 2/1997 | Giese | 435/7.1 |
| 5,610,020 A | 3/1997 | Giese | 435/7.1 |
| RE35,491 E | 4/1997 | Cline | 435/6 |
| 5,616,719 A | 4/1997 | Davalian | 546/334 |
| 5,624,800 A | 4/1997 | Grossman | 435/6 |
| 5,646,001 A | 7/1997 | Terstappen | 435/7.21 |
| 5,650,270 A | 7/1997 | Giese | 435/6 |
| 5,703,222 A | 12/1997 | Grossman | 536/24.3 |
| 5,705,622 A | 1/1998 | McCapra | 536/23.1 |
| 5,709,994 A | 1/1998 | Pease | 435/4 |
| 5,721,099 A | 2/1998 | Still | 435/6 |
| 5,756,726 A | 5/1998 | Hemmi | 540/474 |
| 5,766,481 A | 6/1998 | Zambias | 210/656 |
| 5,777,096 A | 7/1998 | Grossman | 536/24.3 |
| 5,789,172 A | 8/1998 | Still | 435/6 |
| 5,800,999 A | 9/1998 | Bronstein | 435/6 |
| 5,804,396 A | 9/1998 | Plowman | 435/7.23 |
| 5,807,675 A | 9/1998 | Davalian | 435/6 |
| 5,807,682 A | 9/1998 | Grossman | 435/6 |
| 5,834,209 A | 11/1998 | Korsmeyer | 435/7.1 |
| 5,843,655 A | 12/1998 | McGall | 435/6 |
| 5,843,666 A | 12/1998 | Akhavan-Tafti | 435/6 |
| 5,843,680 A | 12/1998 | Manian | |
| 5,846,839 A | 12/1998 | Gallop | 436/518 |
| 5,849,878 A | 12/1998 | Cantor | 530/391.9 |
| 5,874,542 A | 2/1999 | Rockwell | 530/387.3 |
| 5,886,238 A | 3/1999 | Schaap | 568/650 |
| 5,952,654 A | 9/1999 | Giese | 250/288 |
| 5,958,202 A | 9/1999 | Regnier | 204/451 |
| 5,968,511 A | 10/1999 | Akita | 424/141.1 |
| 5,986,076 A | 11/1999 | Rothschild | 536/22.1 |
| 5,989,871 A | 11/1999 | Grossman | 435/91.1 |
| 6,001,573 A | 12/1999 | Roelant | 435/6 |
| 6,001,579 A | 12/1999 | Still | 435/7.1 |
| 6,027,890 A | 2/2000 | Ness | 435/6 |
| 6,248,546 B1 | 6/2001 | Khosravi | 435/7.94 |
| 6,251,581 B1 | 6/2001 | Ullman | 435/4 |
| 6,312,893 B1 | 11/2001 | Van Ness | 435/6 |
| 6,322,980 B1 | 11/2001 | Singh | 435/6 |
| 6,331,530 B1 | 12/2001 | Breslow | 514/58 |
| 6,335,201 B1 | 1/2002 | Allbritton | 436/63 |
| 6,346,384 B1 | 2/2002 | Pollner | 435/6 |
| 6,346,529 B1 | 2/2002 | Floyd | 514/226.2 |
| 6,358,682 B1 | 3/2002 | Jaffee | 435/6 |
| 6,365,362 B1 | 4/2002 | Terstappen | 435/7.23 |
| 6,368,874 B1 | 4/2002 | Gallop | 436/518 |
| 6,383,740 B2 | 5/2002 | Collins | 435/5 |
| 6,388,063 B1 | 5/2002 | Plowman | 536/23.5 |
| 6,417,168 B1 | 7/2002 | Greene | 514/44 |
| 6,489,116 B2 | 12/2002 | Wagner | 435/6 |
| 6,558,928 B1 | 5/2003 | Landegren | 435/91.1 |
| 6,573,043 B1 | 6/2003 | Cohen | 435/6 |
| 6,627,196 B1 | 9/2003 | Baughman | 424/138.1 |
| 6,627,400 B1 | 9/2003 | Singh | 435/6 |
| 6,649,351 B2 * | 11/2003 | Matray et al. | 435/6 |
| 6,727,072 B2 | 4/2004 | Spaulding | 435/7.21 |
| 6,770,439 B2 * | 8/2004 | Singh et al. | 435/6 |
| 7,105,308 B2 * | 9/2006 | Chan-Hui et al. | 435/7.2 |
| 7,135,300 B2 * | 11/2006 | Chan-Hui et al. | 435/7.2 |
| 2002/0037542 A1 | 3/2002 | Allbritton | 435/7.23 |
| 2002/0064779 A1 | 5/2002 | Landegren | 435/6 |
| 2002/0172984 A1 | 11/2002 | Holland | 435/7.21 |
| 2003/0170734 A1 | 9/2003 | Williams et al. | 435/7.1 |
| 2003/0190689 A1 | 10/2003 | Crosby | 435/7.23 |
| 2003/0207403 A1 | 11/2003 | Paszty | 435/69.1 |
| 2004/0018528 A1 | 1/2004 | Morimoto | 435/6 |
| 2004/0018562 A1 | 1/2004 | Rouhani | 435/7.1 |
| 2004/0023288 A1 | 2/2004 | Ridder | 435/6 |
| 2004/0029194 A1 | 2/2004 | Parish | 435/7.23 |
| 2004/0033542 A1 | 2/2004 | Frackelton | 435/7.23 |

FOREIGN PATENT DOCUMENTS

| | | |
|---|---|---|
| WO | WO 93/06121 | 4/1993 |
| WO | WO 96/24061 | 8/1996 |
| WO | WO 97/27325 | 7/1997 |
| WO | WO 97/27327 | 7/1997 |
| WO | WO 97/28275 | 8/1997 |
| WO | WO 98/01533 | 1/1998 |
| WO | WO 98/15830 | 4/1998 |
| WO | WO 99/05319 | 2/1999 |
| WO | WO 99/42838 | 8/1999 |
| WO | WO 99/64519 | 12/1999 |
| WO | WO 00/56925 | 9/2000 |
| WO | WO 00/66607 | 11/2000 |
| WO | WO 03/028659 | 4/2003 |
| WO | WO 03/045990 | 6/2003 |
| WO | WO 2004/008099 | 1/2004 |
| WO | WO 2004/009798 | 1/2004 |

OTHER PUBLICATIONS

Baselga, "A new anti-ErbB2 strategy in the treatment of cancer: Prevention of ligand-dependent ErbB2 receptor heterodimerization", Cancer Cell, 2002, 2:93-95.

Beaudet, et al., "Homogenous Assays for Single-Nucleotide Polymorphism Typing Using AlphaScreen", Genome Research, 2001, 11:600-608.

Blagoev, et al., "A proteomics strategy to elucidate functional protein-protein interactions applied to EGF signaling", Nature Biotechnology, 2003, 21:315-318.

Blakely, et al., "Epidermal growth factor receptor dimerization monitored in live cells", Nature Biotechnology, 2000, 18:218-222.

Dikic, "CIN85/CMS family of adaptor molecules", FEBS Letters, 2002, 529:110-115.

Fredriksson, et al., "Protein detection using proximity-dependent DNA ligation assays", Nature Biotechnology, 2002, 20:473-477.

Galarneau, et al., "β-Lactamase protein fragment complementation assays in vivo and in vitro sensors of protein-protein interactions", Nature Biotechnology, 2002, 20:619-622.

Gamett, et al., "Secondary Dimerization between Memebers of the Epidermal Growth Factor Receptor Family", The Journal of Biological Chemistry, 1997, 272:12052-12056.

Graham, et al., "Application of β-Galactosidase Enzyme Complementation Technology as a High Throughput Screening format for Antagonists of the Epidermal Growth Factor Receptor", Journal of Biomolecular Screening, 2001, 6:401-411.

Graus-Porta, et al., "ErbB-2, the preferred heterodimerization partner of all ErbB receptors, is a mediator of lateral signaling", The EMBO Journal, 1997, 16:1647-1655.

Irvine, et al., "A colorimetric bead-binding assay for detection of intermolecular interactions", Experimental Dermatology, 2002, 11:462-467.

Karin, et al., "NF-κB in Cancer: From Innocent Bystander to Major Culprit", Nature Reviews Cancer, 2002, 2:301-310.

Kolch, "Meaningful relationships: the regulation of the Ras/Raf/MEK/ERK pathway by protein interaction", Biochem. J., 2000, 351:289-305.

Lund-Johansen, et al., "Flow Cytometric Analysis of Immunoprecipitates: High-Throughput Analysis of Protein Phosphorylation and Protein-Protein Interactions", Cytometry, 2000, 39:250-259.

McDonald, et al., "A Scintillation Proximity Assay for the Raf/MEK/ERK Kinase Cascade: High-Throughput Screening and Identification of Selective Enzyme Inhibitors", Analytical Biochemistry, 1999, 268:318-329.

Mallon, et al., "An Enzyme-Linked Immunosorbent Assay for the Raf/MEK1/MAPK Signaling Cascade", Analytical Biochemistry, 2001, 294:48-54.

Matko, et al., "Energy Transfer Methods for Detecting for the Raf/MEK1/MAPK Signaling Cascade", Analytical Biochemistry, 2001, 294:48-54.

Muthuswamy, et al., "Controlled Dimerization of ErbB Receptors Provides Evidence for Differential Signaling by Homo- and Heterodimers", Molecular Cell Biology, 1999, 6845-6857.

Orlowski, et al., "NF-κB as a therapeutie target in cancer", Trends in Molecular Medicine, 2002, 8:385-389.

Packard BioScience, "Principles of AlphaScreen", Application Note ASC-001, 2001.

Pawson, et al., "Assembly of Cell Regulatory Systems Through Protein Interaction Domains", Science, 2003, 300:445-452.

Pawson, et al., "Interaction domains: from simple binding events to complex cellular behavior", FEBS Letters, 2002, 513:2-10.

Petricoin, et al., "Use of proteomic patterns in serum to identify ovarian cancer", The Lancet, 2002, 359:572-577.

Price, et al., "Methods for the Study of Protein-Protein Interactions in Cancer Cell Biology", Methods in Molecular Biology, 2003, 218:255-267.

Sidransky, "Emerging Molecular Markers of Cancer", Nature Reviews Cancer, 2002, 2:210-219.

Sklar, et al., "Flow Cytometric Analysis of Ligand-Receptor Interactions and Molecular Assemblies", Annu. Rev. Biomol. Struct., 2002, 31:97-119.

Stagljar, "Finding Partners: Emerging Protein Interaction Technologies Applied to Signaling Networks", Sci. STKE, 2003, pe56:1-5.

Stancato, et al., "Figherprinting of signal transduction pathways using a combination of anti-phosphotyrosine immunoprecipitations and two-dimensional polycrylamide gel electrophoresis", Electrophoresis, 2001, 22:2120-2124.

Szöllösi, et al.; "Applications of fluorescence resonance energy transfer for mapping biological membranes", Reviews in Molecular Biotechnology, 2002, 82:251-266.

Xenarios, et al., "DIP: the Database of Interacting Proteins", Nucleic Acid Research, 2000, 28:289-291.

Xenarios, et al., "Protein interaction databases", Current Opinion in Biotechnology, 2001, 12:334-339.

Yan, et al., "Analysis of protein interactions using fluorescence technologies", Current Opinion in Chemical Biology, 2003, 7:635-640.

Yarmush, et al., "Advances in Proteomic Technologies", Annu. Rev. Biomed. Eng. 2002, 4:349-373.

Fitch et al., "Improved Methods for Encoding and Decoding Dialkylamine-Encoded Combinatorial Libraries", J. Comb. Chem., I, 1999, pp. 188-194.

Giese, "Electrophoric Release Tags: Ultrasensitive Molecular Labels Providing Multiplicity", Trends in Analytical Chemistry, vol. 2, No. 7, 1983, pp. 166-168.

Kochevar et al., "Photosensitized Production of Singlet Oxygen", Methods in Enzymology, vol. 319, 2000, pp. 20-29.

Liu et al., "Capillary Electrochromatography-laser-induced Fluorescence Method for Separation and Detection of Dansylated Dialkylamine Tags in Encoded Combinatorial Libraries", Journal of Chromatorgraphy, Art. 924, 2001, pp. 323-329.

Lum et al., "Ability of Specific Monoclonal Antibodies and Conventional Antisera Conjugated to Hematoporphyrin to Label and Kill Selected Cell Lines Subsequent to Light Activation", Cancer Research, vol. 45, 1985, pp. 4380-4386.

Oseroff et al., "Antibody-Targeted Photolysis: Selective photodestruction of Human T-Cell Leukemia Cells Using Monoclonal Antibody-Chlorin $e_6$ Conjugates", Proc. Natl. Acad. Sci. USA, vol. 83, 1986, pp. 8744-8748.

Rakestraw et al., "Antibody-Targeted photolysis: In vitro Studies with Sn(IV) Chlorin e6 Covalently Bound to Monoclonal Antibodies Using a Modified Dextran Carrier", Proc. Natl. Acad. Sci. USA, vol. 87, 1990, pp. 4217-4221.

Da Ros et al., "DNA-Photocleavage Agents", Current Pharmaceutical Design, vol. 7, 2001, pp. 1781-1821.

Sharman et al., "Role of Activated Oxygen Species in Photodynamic Therapy", Methods in Enzymology, vol. 319, 2000, pp. 376-400.

Still, "Discovery of Sequence-Selective Peptide Binding by Synthetic Receptors Using Encoded Combinatorial Libraries", Acc. Chem. Res., vol. 29, 1996, pp. 155-163.

Strong, "Antibody-Targeted Photolysis", Annals New York Academy of Sciences, vol. 745, 1994, pp. 297-320.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426-5430.

Yarmush et al., "Antibody Targeted Photolysis", Critical Reviews in Therapeutic Drug Carrier Systems, vol. 10, 1993, pp. 197-252.

Yemul et al., "Selective Killing of T Lymphocytes by Phototoxic Liposomes", Proc. Natl. Acad. Sci. USA, vol. 84, 1987, pp. 246-250.

Joppich-Kuhn et al, "Release Tags: A new class of analytical reagents," Clin. Chem., 28: 1844-1847 (1982).

McVey et al, "Monitoring receptor oligomerization using time-resolved fluorescence resonance energy transfer and bioluminescence resonance energy transfer," J. Biol. Chem., 276: 14092-14099 (2001).

Salim et al, "Oligomerization of G-protein-coupled Receptors Shown by Selective Co-immunoprecipitation", Journal of Bioligical Chemistry, 2002, vol. 277, No. 18, Issue of May 3, 2002, 15482-15485.

Angers et al, "Detection of $\beta_2$-Adrenergic Receptor Dimerization in Living Cells Using Bioluminescence Resonance Energy Transfer (BRET)", PNAS, Mar. 28, 2000, vol. 97, No. 7, 3684-3689.

* cited by examiner

Thiazole cleavable linkage

Oxazole cleavable linkage

Olefin cleavable linkage

X = morpholino
= OR'
= SR''

Thioether cleavable linkage

Pro1-NHS

Pro2-NHS

Pro3-NHS

Pro4-NHS

Pro5-NHS

Pro6-NHS

Pro7-NHS

Pro8-NHS

Pro9-NHS

Pro10-NHS

Pro11-NHS

Pro12-NHS

Pro13-NHS

Pro14-NHS

Pro15-NHS

Pro16-NHS

Pro17-NHS

Pro18-NHS

Pro19-NHS

Pro20-NHS

Pro21-NHS

Pro22-NHS

Pro23-biotin

Pro24-biotin

Pro25-biotin

Pro26-biotin

Pro27-biotin

Pro28-NHS

Pro28-biotin

Pro29-NHS

Pro29-biotin

Pro30-NHS

Pro30-biotin

Pro31-NHS

Pro32-NHS

Pro32-biotin

Pro33-NHS

Pro33-biotin

Synthesis of Pro15

Synthesis of Pro28

Shc/Her-2 Complex in MCF-7 Cells

DETECTING AND PROFILING MOLECULAR COMPLEXES

CROSS-REFERENCE TO RELATED APPLICATIONS AND PATENTS

This is a continuation-in-part of U.S. patent applications Ser. No. 10/623,057 filed 17 Jul. 2003 now U.S. Pat. No. 7,105,308 and Ser. No. 10/154,042 filed 21 May 2002, now U.S. Pat. No. 7,255,999, and further claims priority from U.S. provisional applications Ser. No. 60/494,482 filed 11 Aug. 2003, Ser. No. 60/508,034 filed 1 Oct. 2003, and Ser. No. 60/512,941 filed 20 Oct. 2003, each of the foregoing applications being incorporated by reference in its entirety.

FIELD OF THE INVENTION

The present invention relates generally to methods for detecting and measuring molecular complexes, and more particularly, to methods for simultaneously measuring complexes among multiple proteins, especially within biological cells.

BACKGROUND OF THE INVENTION

The formation and disassociation of molecular complexes are crucial to regulatory processes in living organisms. In particular, signaling pathways between the surface and nucleus of cells involve the formation of many molecular complexes in which multiple proteins are assembled to directly or indirectly induce molecular events, such as phosphorylation or dephosphorylation, which are steps in the signaling process, Gomperts et al, Signal Transduction (Academic Press, New York, 2002). Such pathways and their components have been the subject of intense investigation because of the role aberrant pathway behavior plays in many disease conditions, especially cancer, e.g. McCormick, Trends in Cell Biology, 9: 53-56 (1999); Blume-Jensen and Hunter, Nature, 411: 355-365 (2001); Nicholson et al, Cellular Signalling, 14: 381-395 (2002); and the like. It has been observed that many cancers are associated with an accumulation of mutations or other genetic alterations that affect components of signaling pathways, e.g. by over expression, particularly those pathways involved with cell proliferation, cell motility, differentiation, and cell death, e.g. Blume-Jensen and Hunter (cited above). Unfortunately, such signaling pathways have been difficult to study not only because of their complexity and interconnectedness, but also because of the disruptive procedures required for analysis of intracellular complexes, e.g. Weng et al, Science, 284: 92-96 (1999); Machida et al, Molecular & Cellular Proteomics, 2.4: 215-233 (2003); Price et al, Methods in Molecular Biology, 218: 255-267 (2003). In particular, the study of phosphorylation states of signaling proteins has been difficult because during sample preparation the phosphorylation state is rapidly altered by the actions of enzymes, such as phosphatases.

A wide variety of techniques have been used to study cellular protein-protein interactions and complexes, including immunoprecipitation, chemical cross-linking, bioluminescence resonance energy transfer (BRET), fluorescence resonance energy transfer (FRET), and the like, e.g. Price et al (cited above); Sorkin et al, Curr. Biol., 10: 1395-1398 (2000); McVey et al, J. Biol. Chem., 17: 14092-14099 (2001); Salim et al, J. Biol. Chem., 277: 15482-15485 (2002); Angers et al, Proc. Natl. Acad. Sci., 97: 3684-3689 (2000). Unfortunately, such techniques are difficult to apply, and generally lack sufficient sensitivity to provide an accurate picture of the state of a signaling pathway.

In view of the above, the availability of a convenient, sensitive, and cost effective technique for simultaneously detecting or measuring one or more molecular complexes, particularly those in signaling pathways, would advance many fields where such measurements are becoming increasingly important, including life science research, medical research and diagnostics, drug discovery, and the like.

SUMMARY OF THE INVENTION

The invention provides methods of detecting and/or measuring complexes of molecules, especially complexes comprising two or more proteins. In one aspect, the method of the invention uses at least two reagents that are specific for different members of a complex: one member, referred to herein as a cleaving probe, has a cleavage-inducing moiety that may be induced to cleave susceptible bonds within its immediate proximity; and the other member, referred to herein as a binding compound, has one or more molecular tags attach by linkages that are cleavable by the cleavage-inducing moiety. In accordance with the method, whenever such different members form a complex, the cleavable linkages are brought within the effective cleaving proximity of the cleavage-inducing moiety so that molecular tags can be released. The molecular tags are then separated from the reaction mixture and quantified to provide a measure of complex formation.

In one aspect, the invention includes a method for detecting or measuring the amounts of one or more complexes comprising the following steps: (i) providing for each of the one or more complexes a cleaving probe specific for a first protein in each of the one or more complexes, each cleaving probe having a cleavage-inducing moiety with an effective proximity; (ii) providing one or more binding compounds specific for a second protein of each of the one or more complexes, such that each binding compound has one or more molecular tags each attached thereto by a cleavable linkage, and such that the one or more molecular tags attached to different binding compounds have different separation characteristics so that upon separation molecular tags from different binding compounds form distinct peaks in a separation profile; (iii) mixing the cleaving probes, the binding compounds, and the one or more complexes such that cleaving probes specifically bind to first proteins of the complexes and binding compounds specifically bind to the second proteins of the complexes and such that cleavable linkages of the binding compounds are within the effective proximity of cleavage-inducing moieties of the cleaving probes so that molecular tags are released; and (iv) separating and identifying the released molecular tags to determine the presence or absence or the amount of the one or more complexes of proteins.

In another aspect, the invention includes a method for detecting or measuring the amount of a single complex comprising the steps: (i) providing a cleaving probe specific for an antigenic determinant of a first protein of the complex, the cleaving probe having a cleavage-inducing moiety with an effective proximity; (ii) providing one or more binding compounds each specific for an antigenic determinant of one or more second proteins of the complex, such that each binding compound has one or more molecular tags each attached thereto by a cleavable linkage, and such that the one or more molecular tags attached to different binding compounds have different separation characteristics so that upon separation molecular tags from different binding compounds form distinct peaks in a separation profile; (iii) mixing the cleaving probe, the one or more binding compounds, and the biological sample such that the cleaving probe specifically binds to the first protein and the one or more binding compounds specifically bind to the one or more second proteins, and such that cleavable linkages of the binding compounds are within the effective proximity of cleavage-inducing moieties of the cleaving probes so that molecular tags are released; and (iv) separating and identifying the released molecular tags to determine the presence or absence or the amount of the complex in the biological sample.

The present invention provides a method of detecting or measuring the formation of one or more molecular complexes that has several advantages over current techniques including, but not limited to, (1) the detection and/or measurement of molecular tags that are separated from an assay mixture provide greatly reduced background and a significant gain in sensitivity; and (2) the use of molecular tags that are specially designed for ease of separation and detection thereby providing convenient multiplexing capability. The present invention also provides a alternative measure of the state of signal transduction whenever phosphorylation is associated with the formation of complexes.

DEFINITIONS

Figure 1A:
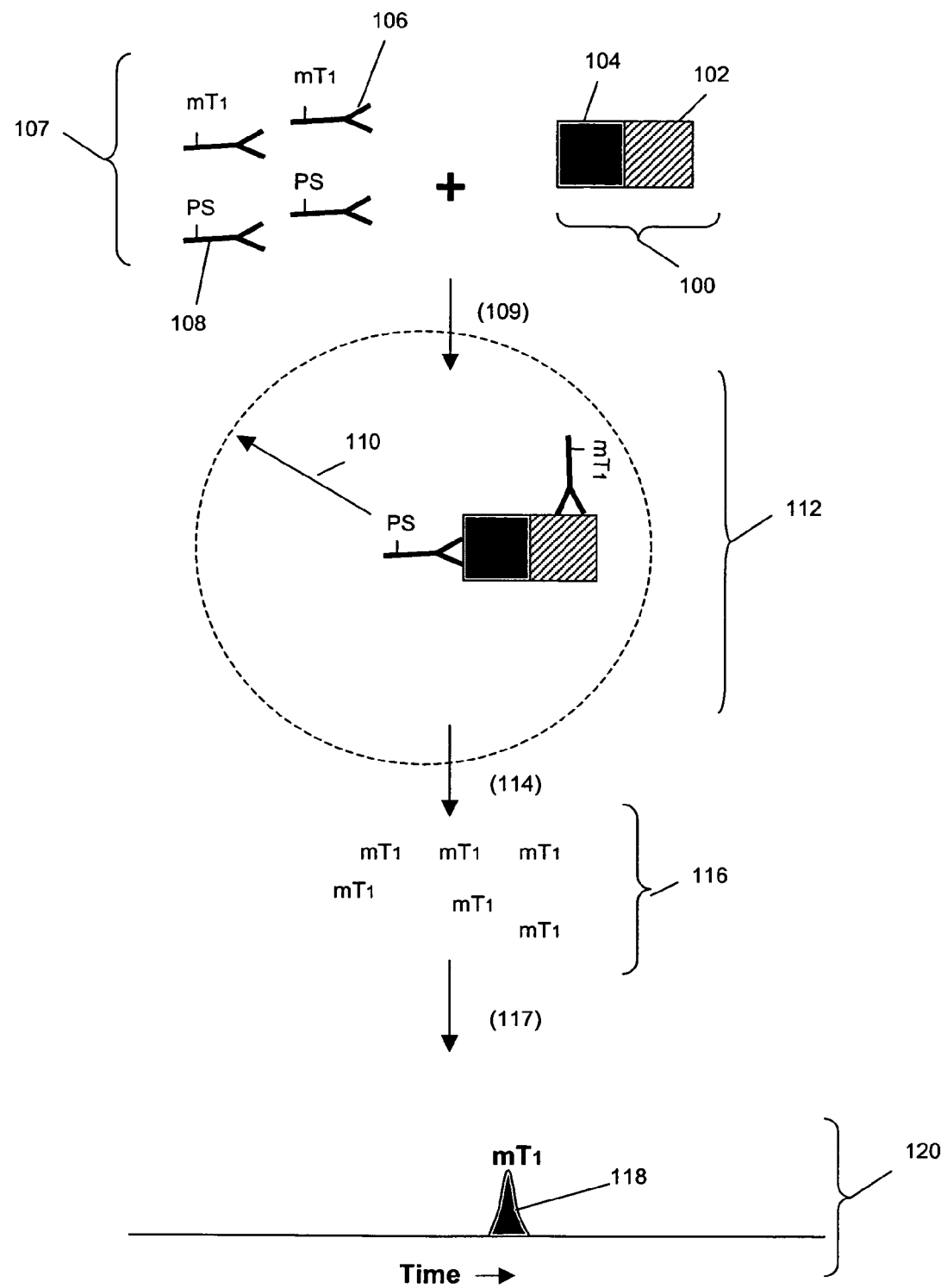
FIGS. 1A-1I illustrate diagrammatically several embodiments of the method of the invention for measuring the presence of protein complexes.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained. Guidance in the production and selection of antibodies for use in immunoassays, including such assays employing releasable molecular tag (as described below) can be found in readily available texts and manuals, e.g. Harlow and Lane, Antibodies: A Laboratory Manual (Cold Spring Harbor Laboratory Press, New York, 1988); Howard and Bethell, Basic Methods in Antibody Production and Characterization (CRC Press, 2001); Wild, editor, The Immunoassay Handbook (Stockton Press, New York, 1994), and the like.

"Antibody binding composition" means a molecule or a complex of molecules that comprises one or more antibodies, or fragments thereof, and derives its binding specificity from such antibody or antibody fragment. Antibody binding compositions include, but are not limited to, (i) antibody pairs in which a first antibody binds specifically to a target molecule and a second antibody binds specifically to a constant region of the first antibody; a biotinylated antibody that binds specifically to a target molecule and a streptavidin protein, which protein is derivatized with moieties such as molecular tags or photosensitizers, or the like, via a biotin moiety; (ii) antibodies specific for a target molecule and conjugated to a polymer, such as dextran, which, in turn, is derivatized with moieties such as molecular tags or photosensitizers, either directly by covalent bonds or indirectly via streptavidin-biotin linkages; (iii) antibodies specific for a target molecule and conjugated to a bead, or microbead, or other solid phase support, which, in turn, is derivatized either directly or indirectly with moieties such as molecular tags or photosensitizers, or polymers containing the latter.

"Antigenic determinant," or "epitope" means a site on the surface of a molecule, usually a protein, to which a single antibody molecule binds; generally a protein has several or many different antigenic determinants and reacts with antibodies of many different specificities. A preferred antigenic determinant is a phosphorylation site of a protein.

"Binding moiety" means any molecule to which molecular tags can be directly or indirectly attached that is capable of specifically binding to an analyte. Binding moieties include, but are not limited to, antibodies, antibody binding compositions, peptides, proteins, nucleic acids, and organic molecules having a molecular weight of up to 1000 daltons and consisting of atoms selected from the group consisting of hydrogen, carbon, oxygen, nitrogen, sulfur, and phosphorus. Preferably, binding moieties are antibodies or antibody binding compositions.

"Capillary-sized" in reference to a separation column means a capillary tube or channel in a plate or microfluidics device, where the diameter or largest dimension of the separation column is between about 25-500 microns, allowing efficient heat dissipation throughout the separation medium, with consequently low thermal convection within the medium.

"Chromatography" or "chromatographic separation" as used herein means or refers to a method of analysis in which the flow of a mobile phase, usually a liquid, containing a mixture of compounds, e.g. molecular tags, promotes the separation of such compounds based on one or more physical or chemical properties by a differential distribution between the mobile phase and a stationary phase, usually a solid. The one or more physical characteristics that form the basis for chromatographic separation of analytes, such as molecular tags, include but are not limited to molecular weight, shape, solubility, pKa, hydrophobicity, charge, polarity, and the like. In one aspect, as used herein, "high pressure (or performance) liquid chromatography" ("HPLC") refers to a liquid phase chromatographic separation that (i) employs a rigid cylindrical separation column having a length of up to 300 mm and an inside diameter of up to 5 mm, (ii) has a solid phase comprising rigid spherical particles (e.g. silica, alumina, or the like) having the same diameter of up to 5 µm packed into the separation column, (iii) takes place at a temperature in the range of from 35° C. to 80° C. and at column pressure up to 150 bars, and (iv) employs a flow rate in the range of from 1 µL/min to 4 mL/min. Preferably, solid phase particles for use in HPLC are further characterized in (i) having a narrow size distribution about the mean particle diameter, with substantially all particle diameters being within 10% of the mean, (ii) having the same pore size in the range of from 70 to 300 angstroms, (iii) having a surface area in the range of from 50 to 250 $m^2/g$, and (iv) having a bonding phase density (i.e. the number of retention ligands per unit area) in the range of from 1 to 5 per $nm^2$. Exemplary reversed phase chromatography media for separating molecular tags include particles, e.g. silica or alumina, having bonded to their surfaces retention ligands, such as phenyl groups, cyano groups, or aliphatic groups selected from the group including $C_8$ through $C_{18}$. Chromatography in reference to the invention includes "capillary electrochromatography" ("CEC"), and related techniques. CEC is a liquid phase chromatographic technique in which fluid is driven by electroosmotic flow through a capillary-sized column, e.g. with inside diameters in the range of from 30 to 100 µm. CEC is disclosed in Svec, Adv. Biochem. Eng. Biotechnol. 76: 147 (2002); Vanhoenacker et al, Electrophoresis, 22: 4064-4103 (2001); and like references. CEC column may use the same solid phase materials as used in conventional reverse phase HPLC and additionally may use so-called "monolithic" non-particular packings. In some forms of CEC, pressure as well as electroosmosis drives an analyte-containing solvent through a column.

"Complex" as used herein means an assemblage or aggregate of molecules in direct or indirect contact with one another. In one aspect, "contact," or more particularly, "direct contact" in reference to a complex of molecules, or in reference to specificity or specific binding, means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. It is understood that complexes in fixed tissue samples may be transformed by the fixation process from an assembly of noncovalently interacting molecules to an assembly of covalently linked molecules. That is, as used herein, the term "complex" includes assemblies or complexes of proteins that become covalently linked because of a fixation process. As used herein, "complex" usually refers to a stable aggregate of two or more proteins, and is equivalently referred to as a "protein-protein complex." Most typically, a "complex" refers to a stable aggregate of two proteins. As used herein, an "intracellular complex" or "intracellular protein-protein complex," refers to a complex of proteins normally found in the cytoplasm or nucleus of a biological cell, and may include complexes of one or more intracellular proteins and a surface membrane receptor. Exemplary intracellular proteins that may be part of such complexes include, but are not limit to, PI3K proteins, Grb2 proteins, Grb7 proteins, Shc proteins, and Sos proteins, Src proteins, Cbl proteins, PLCγ proteins, Shp2 proteins, GAP proteins, Nck proteins, Vav proteins, and Crk proteins. In one aspect, such complexes include PI3K or Shc proteins. In another aspect, a complex is a stable aggregate comprising two proteins, or from 2 to 4 proteins, or from 2 to 6 proteins. As used herein, a "signaling complex" is an intracellular protein-protein complex that is a component of a signaling pathway. "Dimer" in reference to a complex of molecules means a complex of two molecules, usually proteins, that may be the same or different. Dimers of identical molecules are referred to as "homodimers" and dimers of different molecules are referred to as "heterodimers."

"ErbB receptor" or "Her receptor" is a receptor protein tyrosine kinase which belongs to the ErbB receptor family and includes EGFR ("Her1"), ErbB2 ("Her2"), ErbB3 ("Her3") and ErbB4 ("Her4") receptors. The ErbB receptor generally comprises an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a native sequence ErbB receptor or an amino acid sequence variant thereof. Preferably the ErbB receptor is native sequence human ErbB receptor. In one aspect, ErbB receptor includes truncated versions of Her receptors, including but not limited to, EGFRvIII and p95Her2, disclosed in Chu et al, Biochem. J., 324: 855-861 (1997); Xia et al, Oncogene, 23: 646-653 (2004); and the like.

The terms "ErbB1", "epidermal growth factor receptor" and "EGFR" and "Her1" are used interchangeably herein and refer to native sequence EGFR as disclosed, for example, in Carpenter et al. Ann. Rev. Biochem. 56:881-914 (1987), including variants thereof (e.g. a deletion mutant EGFR as in Humphrey et al. PNAS (USA) 87:4207-4211 (1990)). erbB1 refers to the gene encoding the EGFR protein product. Examples of antibodies which bind to EGFR include MAb 579 (ATCC CRL RB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225) and reshaped human 225 (H225) (see, WO 96/40210, Imclone Systems Inc.).

"Her2", "ErbB2" "c-Erb-B2" are used interchangeably. Unless indicated otherwise, the terms "ErbB2" "c-Erb-B2" and "Her2" when used herein refer to the human protein. The human ErbB2 gene and ErbB2 protein are, for example, described in Semba et al., PNAS (USA) 82:6497-650 (1985) and Yamamoto et al. Nature 319:230-234 (1986) (Genebank accession number X03363). Examples of antibodies that specifically bind to Her2 are disclosed in U.S. Pat. Nos. 5,677, 171; 5,772,997; Fendly et al, Cancer Res., 50: 1550-1558 (1990); and the like.

"ErbB3" and "Her3" refer to the receptor polypeptide as disclosed, for example, in U.S. Pat. Nos. 5,183,884 and 5,480, 968 as well as Kraus et al. PNAS (USA) 86:9193-9197 (1989), including variants thereof. Examples of antibodies which bind Her3 are described in U.S. Pat. No. 5,968,511, e.g. the 8B8 antibody (ATCC HB 12070).

The terms "ErbB4" and "Her4" herein refer to the receptor polypeptide as disclosed, for example, in EP Pat Appln No 599,274; Plowman et al., Proc. Natl. Acad. Sci. USA, 90:1746-1750 (1993); and Plowman et al., Nature, 366:473-

475 (1993), including variants thereof such as the Her4 isoforms disclosed in WO 99/19488.

"Insulin-like growth factor-1 receptor" or "IGF-1R" means a human receptor tyrosine kinase substantially identical to those disclosed in Ullrich et al, EMBO J., 5: 2503-2512 (1986) or Steele-Perkins et al, J. Biol. Chem., 263: 11486-11492 (1988).

"Kit" refers to any delivery system for delivering materials. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Phosphatidylinositol 3 kinase protein," or equivalently a "PI3K protein," means a human intracellular protein of the set of human proteins describe under NCBI accession numbers NP_852664, NP_852556, and NP_852665, and proteins having amino acid sequences substantially identical thereto.

"Platelet-derived growth factor receptor" or "PDGFR" means a human receptor tyrosine kinase protein that is substantially identical to PDGFRα or PDGFRβ, or variants thereof, described in Heldin et al, Physiological Reviews, 79: 1283-1316 (1999). In one aspect, the invention includes determining the status of cancers, pre-cancerous conditions, fibrotic or sclerotic conditions by measuring one or more dimers of the following group: PDGFRα homodimers, PDGFRβ homodimers, and PDGFRα-PDGFRβ heterodimers. In particular, fibrotic conditions include lung or kidney fibrosis, and sclerotic conditions include atherosclerosis. Cancers include, but are not limited to, breast cancer, colorectal carcinoma, glioblastoma, and ovarian carcinoma. Reference to "PDGFR" alone is understood to mean "PDGFRα" or "PDGFRβ."

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

"Protein" refers to a polypeptide, usually synthesized by a biological cell, folded into a defined three-dimensional structure. Proteins are generally from about 5,000 to about 5,000,000 or more in molecular weight, more usually from about 5,000 to about 1,000,000 molecular weight, and may include posttranslational modifications, such acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, phosphorylation, prenylation, racemization, selenoylation, sulfation, and ubiquitination, e.g. Wold, F., Post-translational Protein Modifications: Perspectives and Prospects, pgs. 1-12 in Post-translational Covalent Modification of Proteins, B. C. Johnson, Ed., Academic Press, New York, 1983. Proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, proteoglycans, and the like.

"Receptor tyrosine kinase," or "RTK," means a human receptor protein having intracellular kinase activity and being selected from the RTK family of proteins described in Schlessinger, Cell, 103: 211-225 (2000); and Blume-Jensen and Hunter (cited above). "Receptor tyrosine kinase dimer" means a complex in a cell surface membrane comprising two receptor tyrosine kinase proteins. In some aspects, a receptor tyrosine kinase dimer may comprise two covalently linked receptor tyrosine kinase proteins.

"Sample" means a quantity of material that is suspected of containing one or more molecular complexes that are to be detected or measured. As used herein, the term includes a specimen (e.g., a biopsy or medical specimen) or a culture (e.g., microbiological culture). It also includes both biological and environmental samples. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. In regard to a human sample or "tissue sample" or "patient sample" or "patient cell or tissue sample" or "specimen," each means a collection of similar cells obtained from a tissue of a subject or patient. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. The tissue sample may contain compounds which are not naturally intermixed with the tissue in nature such as preservatives, anticoagulants, buffers, fixatives, nutrients, antibiotics, or the like. In one aspect of the invention, tissue samples or patient samples are fixed, particularly conventional formalin-fixed paraffin-embedded samples. Such samples are typically used in an assay for complexes in the form of thin sections, e.g. 3-10 μm thick, of fixed tissue mounted on a microscope slide, or equivalent surface. Such samples also typically undergo a conventional re-hydration procedure, and optionally, an antigen retrieval procedure as a part of, or preliminary to, assay measurements.

"Separation profile" in reference to the separation of molecular tags means a chart, graph, curve, bar graph, or other representation of signal intensity data versus a parameter related to the molecular tags, such as retention time, mass, or the like, that provides a readout, or measure, of the number of molecular tags of each type produced in an assay. A separation profile may be an electropherogram, a chromatogram, an electrochromatogram, a mass spectrogram, or like graphical representation of data depending on the separation technique employed. A "peak" or a "band" or a "zone" in reference to a separation profile means a region where a separated compound is concentrated. There may be multiple separation profiles for a single assay if, for example, different molecular tags have different fluorescent labels having distinct emission spectra and data is collected and recorded at multiple wavelengths. In one aspect, released molecular tags are separated by differences in electrophoretic mobility to form an electropherogram wherein different molecular tags correspond to distinct peaks on the electropherogram. A measure of the distinctness, or lack of overlap, of adjacent peaks in an electropherogram is "electrophoretic resolution," which may be taken as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of molecular tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like. Electropherograms may be analyzed to associate features in the data with the presence, absence, or quantities of molecular tags using analysis programs, such as disclosed in Williams et al, U.S. patent publication 2003/0170734.

"SHC" (standing for "Src homology 2/α-collagen-related") means any one of a family of adaptor proteins (66, 52, and 46 kDalton) in RTK signaling pathways substantially identical to those described in Pelicci et al, Cell, 70: 93-104 (1992). In one aspect, SHC means the human versions of such adaptor proteins.

"Signaling pathway" or "signal transduction pathway" means a series of molecular events usually beginning with the interaction of cell surface receptor and/or receptor dimer with an extracellular ligand or with the binding of an intracellular molecule to a phosphorylated site of a cell surface receptor. Such beginning event then triggers a series of further molecular interactions or events, wherein the series of such events or interactions results in a regulation of gene expression, for example, by regulation of transcription in the nucleus of a cell, or by regulation of the processing or translation of mRNA transcripts. In one aspect, signaling pathway means either the Ras-MAPK pathway, the PI3K-Akt pathway, or an mTOR pathway. "Ras-MAPK pathway" means a signaling pathway that includes the phosphorylation of a MAPK protein subsequent to the formation of a Ras-GTP complex. "PI3K-Akt pathway" means a signaling pathway that includes the phosphorylation of an Akt protein by a PI3K protein. "mTOR pathway" means a signaling pathway comprising one or more of the following entities; an mTOR protein, a PI3K protein, an Akt protein, an S6K1 protein, an FKBP protein, including an FKBP12 protein, a TSC1 protein, a TSC2 protein, a p70S6K protein, a raptor protein, a rheb protein, a PDK protein, a 4E-BP1 protein, wherein each of the proteins may be phosphorylated at a post-translational modification site. mTOR pathways may also include the following complexes: FKBP12//mTOR, raptor//mTOR, raptor//4E-BP1, raptor//S6K1, raptor//4E-BP1//mTOR, raptor//S6K1//mTOR (where "X//Y" indicates that X and Y form complex). The proteins of the preceding two sentences are well known to those of skill in the art and are described in the following references, which are incorporated by reference: Sawyers, Cancer Cell, 4: 343-348 (2003); Xu et al, International J. Oncol., 24: 893-900 (2004); Fong et al, Proc. Natl. Acad. Sci., 100: 14253-14258 (2003); Fruman et al, Eur. J. Immunol., 25: 563-571 (1995); Hidalgo et al, Oncogene, 19: 6680-6686 (2000); and the like.

"Specific" or "specificity" in reference to the binding of one molecule to another molecule, such as a binding compound, or probe, for a target analyte or complex, means the recognition, contact, and formation of a stable complex between the probe and target, together with substantially less recognition, contact, or complex formation of the probe with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like.

As used herein, the term "spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al, pgs. 21-76, in Flow Cytometry: Instrumentation and Data Analysis (Academic Press, New York, 1985).

As used herein, "tagged probe" is used synonymously with "binding compound."

"VEGF receptor" or "VEGFR" as used herein refers to a cellular receptor for vascular endothelial growth factor (VEGF), ordinarily a cell-surface receptor found on vascular endothelial cells, as well as variants thereof which retain the ability to bind human VEGF. VEGF receptors include VEGFR1 (also known as Flt1), VEGFR2 (also know as Flk1 or KDR), and VEGFR3 (also known as Flt4). These receptors are described in DeVries et al., Science 255:989 (1992); Shibuya et al., Oncogene 5:519 (1990); Matthews et al., Proc. Nat. Acad. Sci. 88:9026 (1991); Terman et al., Oncogene 6:1677 (1991); Terman et al., Biochem. Biophys. Res. Commun. 187:1579 (1992). Dimers of VEGF receptors are described in Shibuya, Cell Structure and Function, 26: 25-35 (2001); and Ferrara et al, Nature Medicine, 9: 669-676 (2003).

DETAILED DESCRIPTION OF THE INVENTION

The invention provides methods of detecting or measuring amounts molecular complexes in a sample by the use of compositions comprising cleaving probes that generate a locally acting cleaving agent and binding compounds labeled with releasable molecular tags that are released by the cleaving agent. Complex formation is detected by designing cleaving probes and binding compounds such that at least one cleaving probe specifically binds to a different component of a complex than at least one of the binding compounds. In this manner, molecular tags of a predetermined type are released only when a complex is formed.

Figure 1B:
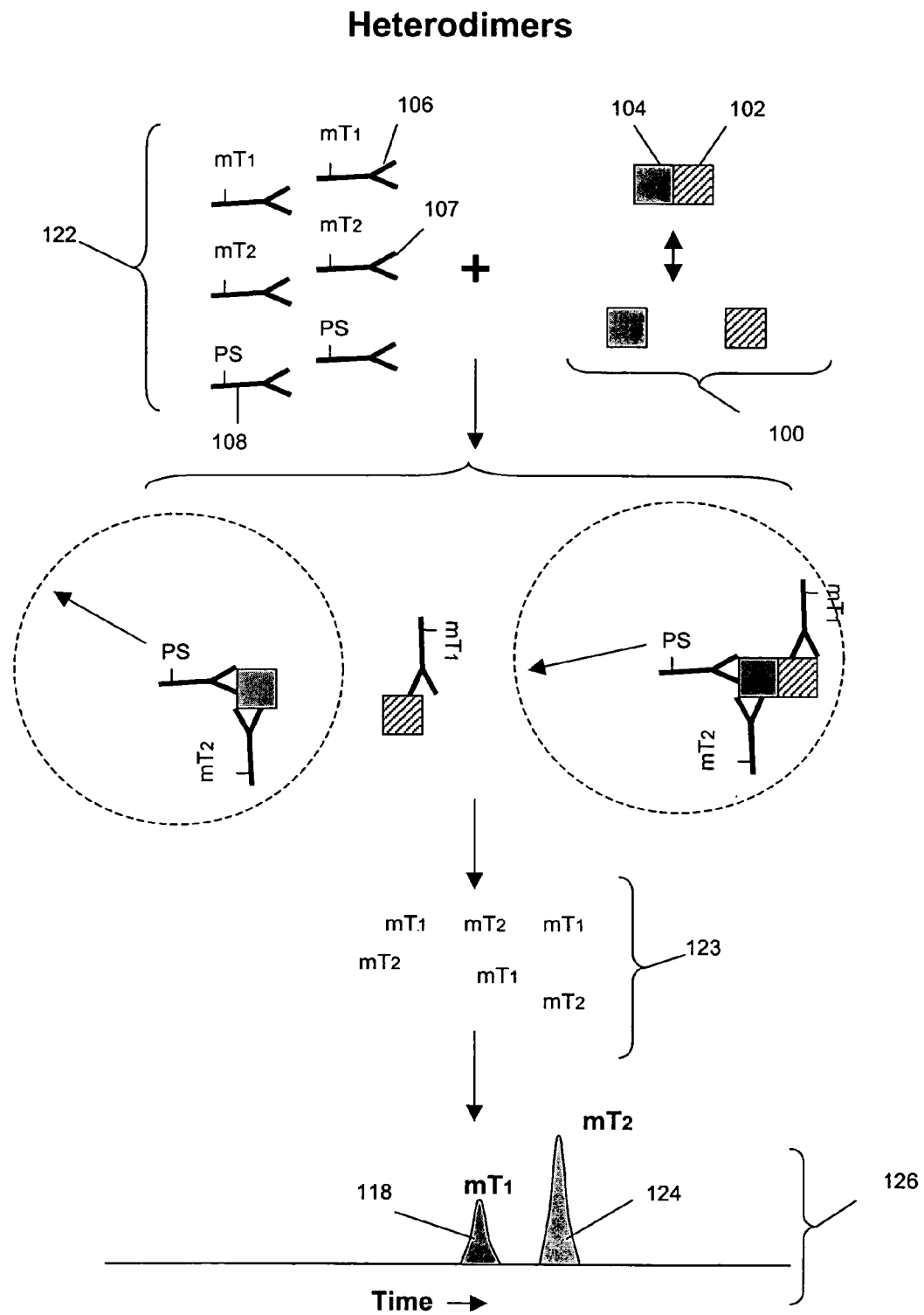

The operation of one embodiment of the invention is illustrated in FIG. 1A. Molecular complex (100) forms by the binding of proteins (104) and (102). Reagents (107) of the invention, comprising cleaving probes (108) (in this illustration having photosensitizer "PS" attached) and binding compounds (106), are mixed (109) with a sample containing complex (100) under conditions that permit the specific binding (112) of cleaving probes (108) and binding compounds (106) to their respective antigenic determinants on complex (100) that are on different proteins of the complex. After binding, and optionally washing or buffer exchange, cleaving probes (108) are activated to generate an active species that, e.g. in the case of singlet oxygen, diffuses out from a photosensitizers to an effective proximity (110). Cleavable linkages within this proximity are cleaved and molecular tags are released (114). Released molecular tags (116) are then separated (117) and a separation profile (120), such as an electropherogram, is produced, in which peak (118) is identified and correlated to molecular tag, "$mT_1$." As slightly more complex embodiment is illustrated in FIG. 1B. Reagents (122) of the invention comprise (i) cleaving probes (108), first binding compound (106), and second binding compound (107), wherein first binding compound (106) is specific for protein (102) and second binding compound (107) is specific for protein (104) at a different antigenic determinant than that cleaving probe (108) is specific for. As with the embodiment of FIG. 1A, after binding of the reagents, cleaving probe (108) is activated to produce active species that cleave the cleavable linkages of the molecular tags within the effective proximity of the photosensitizer. Released molecular tags (123) are separated, and peaks (118 and 124) in a separation profile (126) are correlated to the amounts of the released molecular tags. In this embodiment, relative peak heights, or areas, may reflect (i) the differences in affinity of the first and second binding compounds for their respective antigenic determinants, and/or (ii) the presence or absence of the antigenic determinant that the binding compound is specific for. The later situation is important whenever a binding compound is used to monitor the post-translational state of a protein, e.g. phosphorylation state.

Figure 1C:
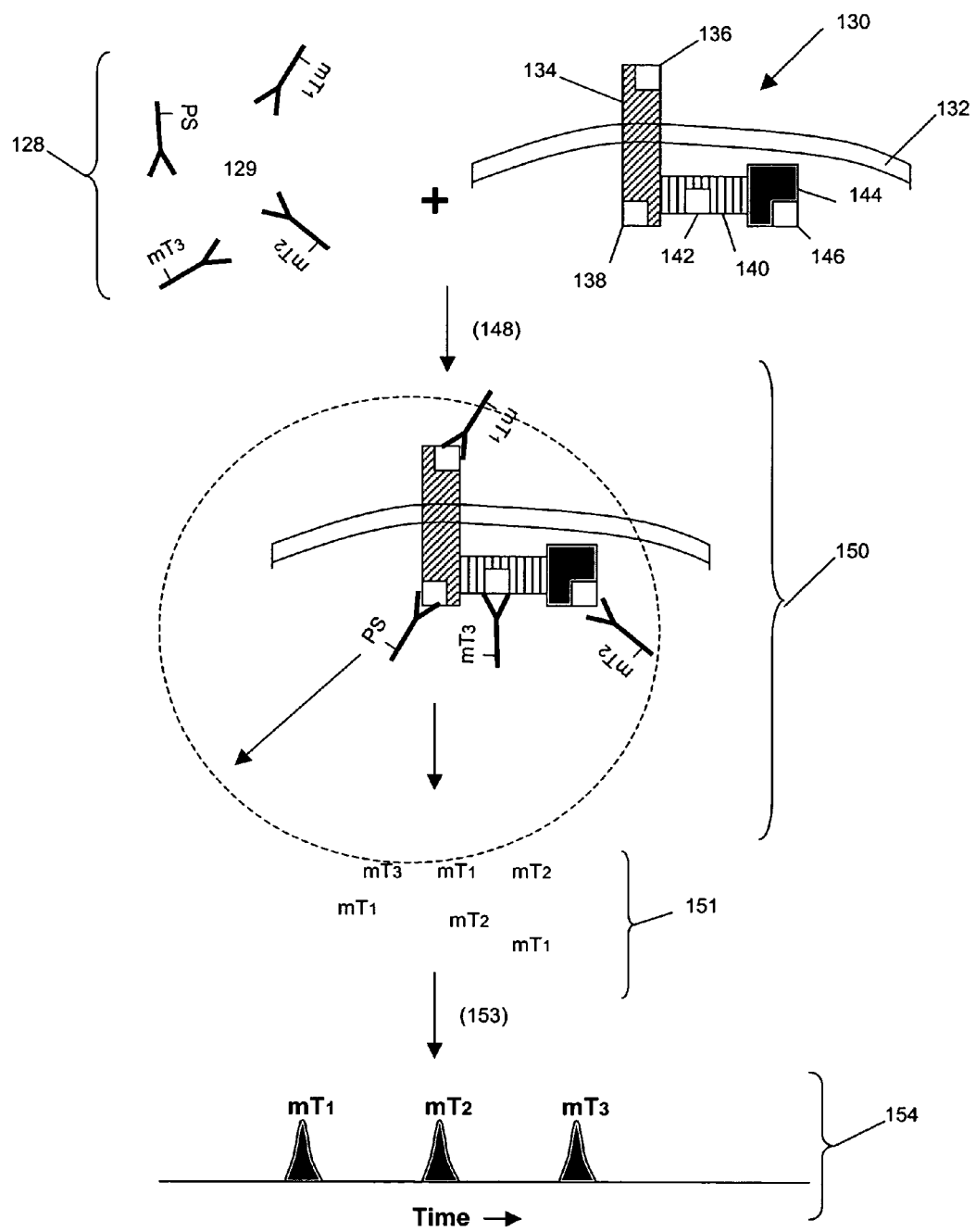

Methods of the invention may be employed to detect or measure the amounts of more complicated complexes, such as that illustrated in FIG. 1C. Complex (130) comprises transmembrane receptor (134) having antigenic determinants (136 and 138), adaptor protein (140) having antigenic determinant (142), and intracellular protein (144) having antigenic determinant (146), all of these components being associated with membrane (132). Many assay designs are possible for detecting and/or measuring a complex such as (130). In the particular design illustrated, cleaving probe (129) is specific for antigenic determinant (138) of transmembrane receptor (134), but in other designs, the reagents could be directed to alternative antigenic determinants. Whenever cleaving probes and binding compounds comprise antibody binding compositions, the assay design may depend on antibody availability, the nature of the complex (e.g. is every component always present, or is the complex dynamic in that some components are only present a small fraction of the time on average), sample preparation, and the like. Generally, cleaving probe (129) binds specifically to a first protein of complex (130); however, depending on the assay design, a first protein could be any of the proteins in the complex. After a first protein is selected, the rest of the proteins in the complex are "second" proteins. In accordance with the invention, at least one second protein is different from the first protein. Returning to FIG. 1C, reagents (128) are combined (148) with a sample containing complex (130) under conditions that allow specific binding (150) of reagents (128), after which cleavage-inducing moiety of cleaving probe (129) is activated to release molecular tags (151). Released molecular tags (151) are then separated and identified in separation profile (154) as described above.

Figure 1D:
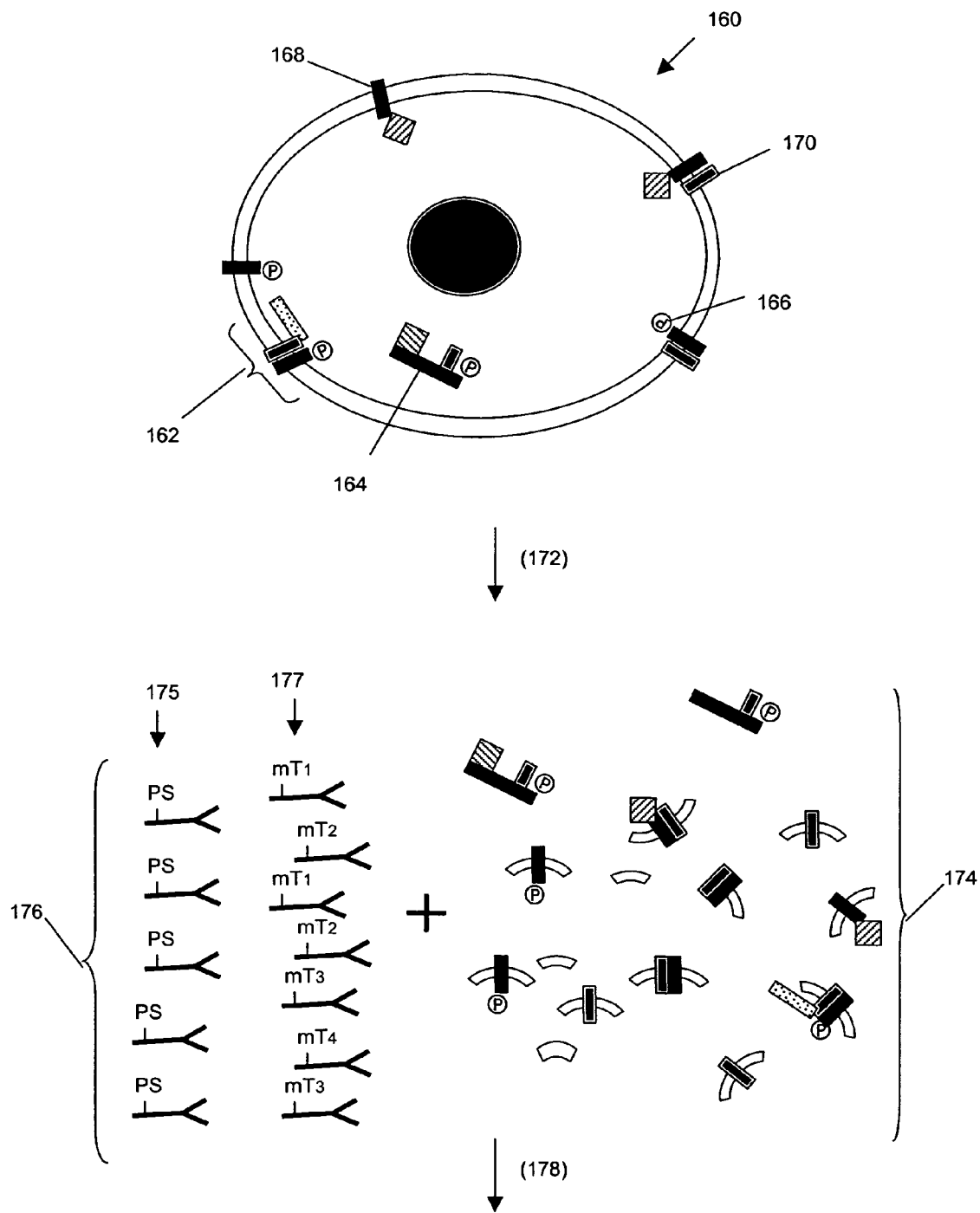
Figure 1E:
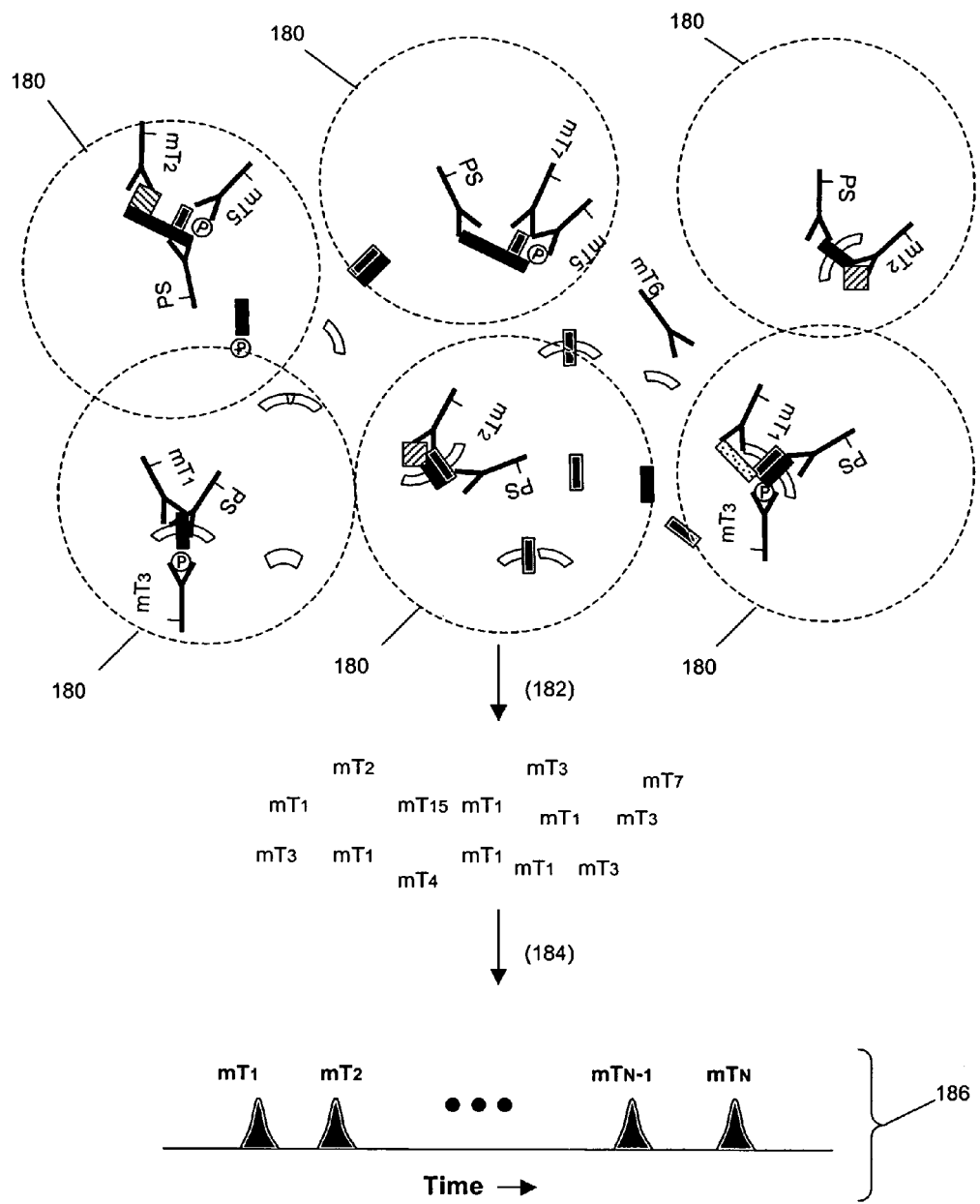

Another aspect of the invention is illustrated in FIGS. 1D and 1E, which provides for the simultaneous detection or measurement of multiple complexes in a cellular sample. Cells (160), which may be from a sample from in vitro cultures or from a specimen of patient tissue, are lysed (172) to render accessible molecular complexes associated with the cell membrane, and/or within the cytosol, and/or within the cell nucleus. Of particular interest are complexes associated with signal transduction processes including, but not limited to, surface receptor complexes, such as dimers, receptor complexes including adaptor or scaffold molecules of various types, phosphorylation sites of proteins in such complexes, and the like. After lysing, the resulting lysate (174) is combined with assay reagents (176) that include multiple cleaving probes (175) and multiple binding compounds (177). Assay conditions are selected (178) that allow reagents (176) to specifically bind to their respective targets, so that upon activation cleavable linkages within the effective proximity (180) of the cleavage-inducing moieties are cleaved and molecular tags are released (182). As above, after cleavage, the released molecular tags are separated (184) and identified in a separation profile (186), such as an electropherogram, and based on the number and quantities of molecular tags measured, a profile is obtained of the selected molecular complexes in the cells of the sample.

Figure 1F:
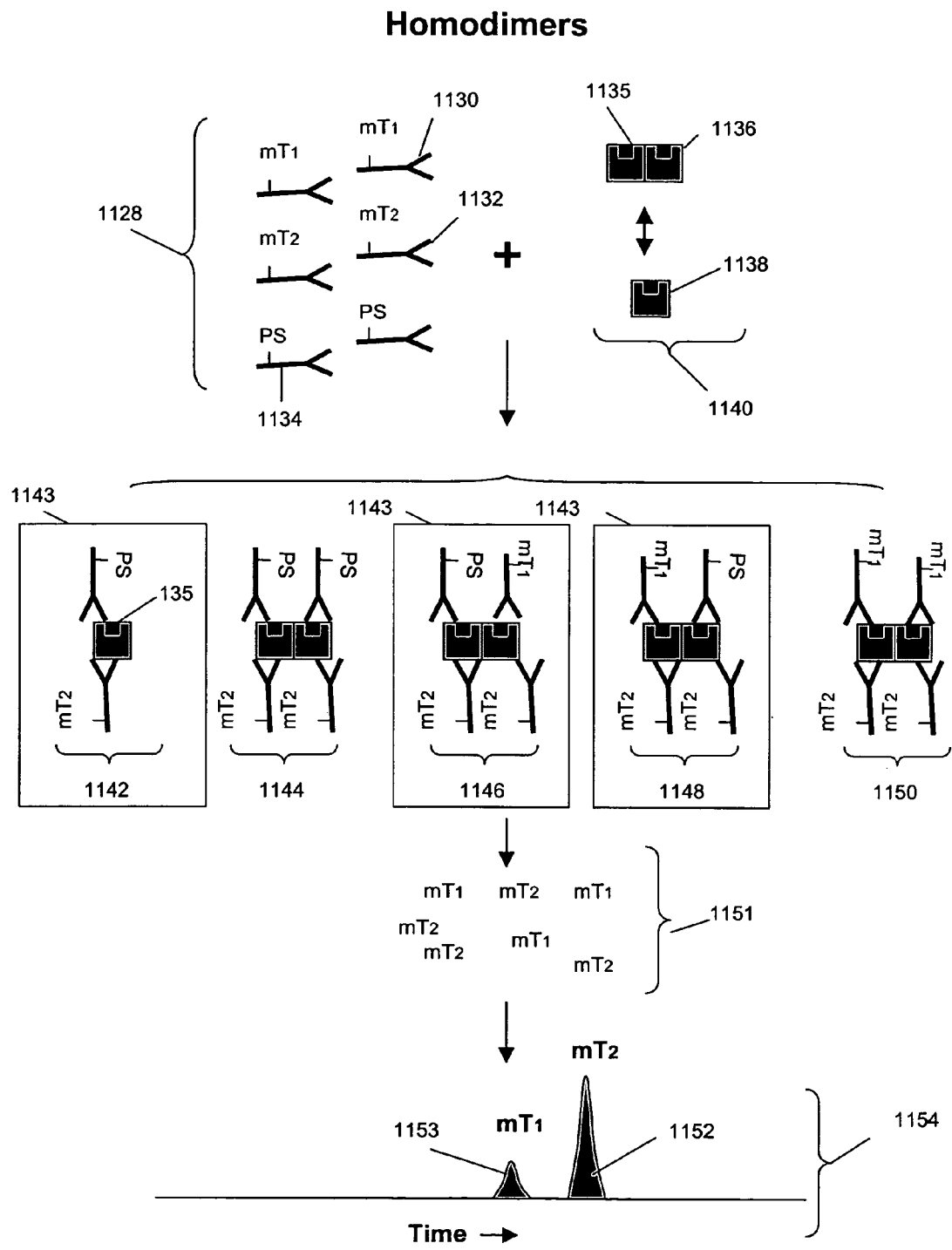

Homodimers may be measured as illustrated in FIG. 1F. As above, an assay may comprise three reagents (1128): cleaving probes (1134), first binding compound (1130), and second binding compound (1132). First binding compound (1130) and cleaving probe (1134) are constructed to be specific for the same antigenic determinant (1135) on protein (1138) that exists (1140) in a sample as either a homodimer (1136) or a monomer (1138). After reagents (1128) are combined with a sample under conditions that promote the formation of stable complexes between the reagents and their respective targets, multiple complexes (1142 through 1150) form in the assay mixture. Because cleaving probe (1134) and binding compound (1130) are specific for the same antigenic determinant (1135), four different combinations (1144 through 1150) of reagents may form complexes with homodimers. Of the complexes in the assay. mixture, only those (1143) with both a cleaving probe (1134) and at least one binding compound will contribute released molecular tags (1151) for separation and detection (1154). In this embodiment, the size of peak (1153) is proportional to the amount of homodimer in the assay mixture, while the size of peak (1152) is proportional to the total amount of protein (1138) in the assay mixture, both in monomeric form (1142) or in homodimeric form (1146 and 1148). FIG. 1E illustrates the analogous measurements for cell surface receptors that form heterodimers in cell surface membrane (1161). One skilled in the art would understand that dimers may be measured in either lysates of cells or tissues, or in fixed samples whose membranes have been permeabilized or removed by the fixing process. In such cases, binding compounds may be specific for either extracellular or intracellular domains of cell surface membrane receptors.

Figure 1G:
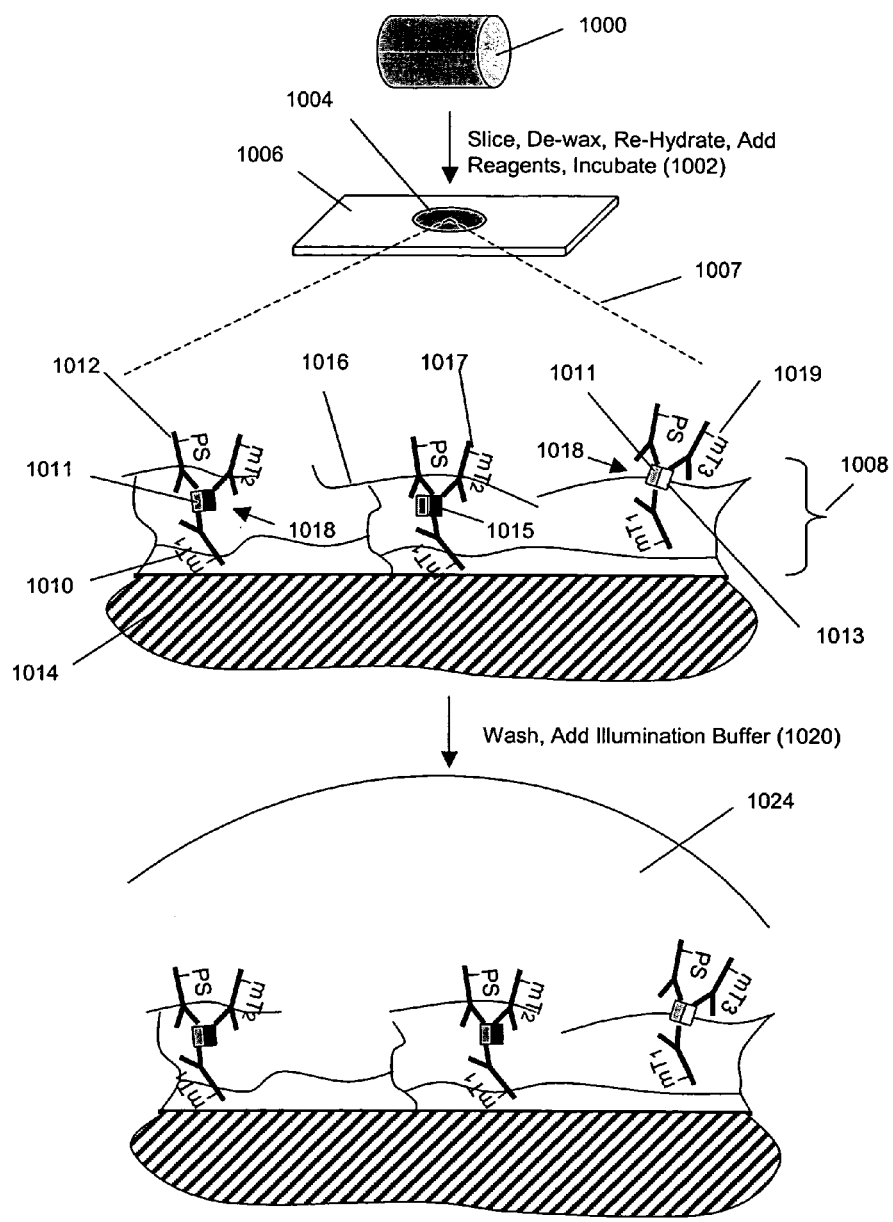
Figure 1H:
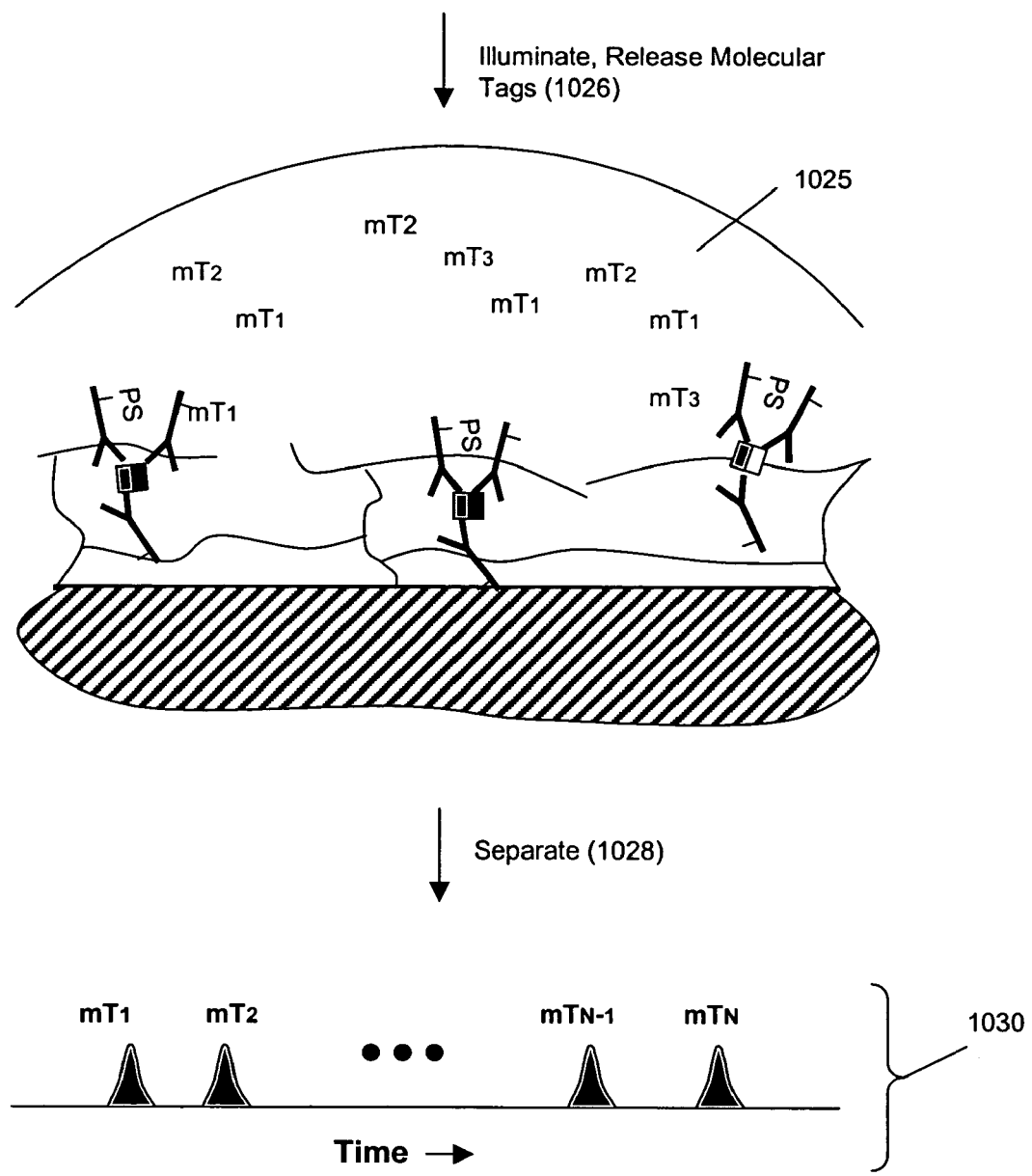

FIGS. 1G and 1H illustrate an embodiment of the invention for measuring receptor complexes in fixed or frozen tissue samples. Fixed tissue sample (1000), e.g. a formalin-fixed paraffin-embedded sample, is sliced to provide a section (1004) using a microtome, or like instrument, which after placing on surface (1006), which may be a microscope slide, it is de-waxed and re-hydrated for application of assay reagents. Enlargement (1007) shows portion (1008) of section (1004) on portion (1014) of microscope slide (1006). Receptor dimer molecules (1018) are illustrated as embedded in the remnants of membrane structure (1016) of the fixed sample. In accordance with this aspect of the invention, cleaving probe and binding compounds are incubated with the fixed sample so that they bind to their target molecules. For example, cleaving probes (1012)(illustrated in the figure as an antibody having a photosensitizer ("PS") attached) and first binding compound (1010)(illustrated as an antibody having molecular tag "$mT_1$" attached) specifically bind to receptor (1011) common to all of the dimers shown, second binding compound (1017)(with "$mT_2$") specifically binds to receptor (1015), and third binding compound (1019)(with "$mT_3$") specifically binds to receptor (1013). After washing to remove binding compounds and cleaving probe that are not specifically bound to their respective target molecules, buffer (1024) (referred to as "illumination buffer" in the figure) is added. For convenience, buffer (1024) may be contained on section (1004), or a portion thereof, by creating a hydrophobic barrier on slide (1006), e.g. with a wax pen. After illumination of photosensitizers and release of molecular tags (1026), buffer (1024) now containing release molecular tags (1025) is transferred to a separation device, such as a capillary electrophoresis instrument, for separation (1028) and identification of the released molecular tags in, for example, electropherogram (1030).

Measurements made directly on tissue samples, particularly as illustrated in FIGS. 1G and 1H, may be normalized by including measurements on cellular or tissue targets that are representative of the total cell number in the sample and/or the numbers of particular subtypes of cells in the sample. The additional measurement may be preferred, or even necessary, because of the cellular and tissue heterogeneity in patient samples, particularly tumor samples, which may comprise substantial fractions of normal cells. For example, values for the total amount of receptor may be given as a ratio of the following two measurements: area of peak of molecular tag ("$mT_1$") and the area of a peak corresponding to a molecular tag correlated with a cellular or tissue component common to all the cells in the sample, e.g. tubulin, or the like. In some cases, where all the cells in the sample are epithelial cells, cytokeratin may be used. Accordingly, detection methods based on releasable molecular tags may include an additional step of providing a binding compound (with a distinct molecular tag) specific for a normalization protein, such as tubulin.

Figure 1I:
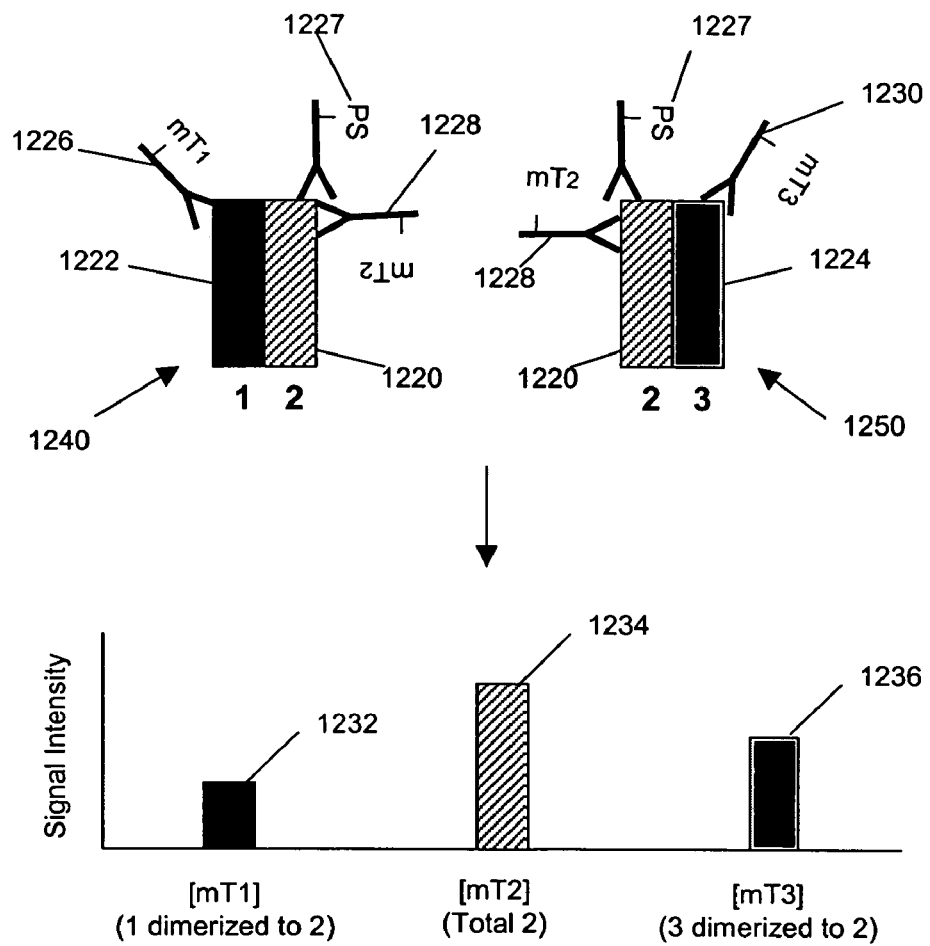

An embodiment for measuring relative amounts of dimers containing a common component is illustrated in FIG. 1I. In this assay design, two different receptor dimers ("1-2" (1240) and "2-3" (1250)) each having a common component, "2," may be measured ratiometrically with respect to the common component. An assay design is shown for measuring receptor heterodimer (1240) comprising receptor "1" (1222) and receptor "2" (1220) and receptor heterodimer (1250) comprising receptor "2" (1220) and receptor "3" (1224). A key feature of this embodiment is that cleaving probe (1227) be made specific for the common receptor of the pair of heterodimers. Binding compound (1228) specific for receptor "2" provides a signal (1234) related to the total amount of receptor "2" in the assay, whereas binding compound (1226) specific for receptor "1" and binding compound (1230) specific for receptor "3" provide signals (1232 and 1236, respectively) related only to the amount of receptor "1" and receptor "3" present as heterodimers with receptor "2, " respectively. The design of FIG. 1I may be generalized to more than two complexes that contain a common component by simply adding binding compounds specific for the components of the additional complexes.

Preparation of Samples

Samples containing molecular complexes may come from a wide variety of sources for use with the present invention to relate receptor complexes populations to disease status or health status, including cell cultures, animal or plant tissues, patient biopsies, or the like. Preferably, samples are human patient samples. Samples are prepared for assays of the invention using conventional techniques, which may depend on the source from which a sample is taken.

A. Solid Tissue Samples.

For biopsies and medical specimens, guidance is provided in the following references: Bancroft J D & Stevens A, eds. Theory and Practice of Histological Techniques (Churchill Livingstone, Edinburgh, 1977); Pearse, Histochemistry. Theory and applied. $4^{th}$ ed. (Churchill Livingstone, Edinburgh, 1980).

In the area of cancerous disease status, examples of patient tissue samples that may be used include, but are not limited to, breast, prostate, ovary, colon, lung, endometrium, stomach, salivary gland or pancreas. The tissue sample can be obtained by a variety of procedures including, but not limited to surgical excision, aspiration or biopsy. The tissue may be fresh or frozen. In one embodiment, assays of the invention are carried out on tissue samples that have been fixed and embedded in paraffin or the like; therefore, in such embodiments a step of deparaffination is carried out. A tissue sample may be fixed (i.e. preserved) by conventional methodology [See e.g., "Manual of Histological Staining Method of the Armed Forces Institute of Pathology," $3^{rd}$ edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Generally, a tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may have a thickness in a range from about three microns to about twelve microns, and preferably, a thickness in a range of from about 5 microns to about 10 microns. In one aspect, a section may have an area of from about 10 mm$^2$ to about 1 cm$^2$. Once cut, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De®(CMS, Houston, Tex.) may be used.

For mammalian tissue culture cells, fresh tissues, or like sources, samples may be prepared by conventional cell lysis techniques (e.g. 0.14 M NaCl, 1.5 mM MgCl$_2$, 10 mM Tris-Cl (pH 8.6), 0.5% Nonidet P40, and protease and/or phosphatase inhibitors as required). For fresh mammalian tissues, sample preparation may also include a tissue disaggregation step, e.g. crushing, mincing, grinding, sonication, or the like.

B. Magnetic Isolation of Cells.

In some applications, such as measuring dimers on rare metastatic cells from a patient's blood, an enrichment step may be carried out prior to conducting an assay for surface receptor dimer populations. Immunomagnetic isolation or enrichment may be carried out using a variety of techniques and materials known in the art, as disclosed in the following representative references that are incorporated by reference: Terstappen et al, U.S. Pat. No. 6,365,362; Terstappen et al, U.S. Pat. No. 5,646,001; Rohr et al, U.S. Pat. No. 5,998,224; Kausch et al, U.S. Pat. No. 5,665,582; Kresse et al, U.S. Pat. No. 6,048,515; Kausch et al, U.S. Pat. No. 5,508,164; Miltenyi et al, U.S. Pat. No. 5,691,208; Molday, U.S. Pat. No. 4,452,773; Kronick, U.S. Pat. No. 4,375,407; Radbruch et al, chapter 23, in Methods in Cell Biology, Vol, 42 (Academic Press, New York, 1994); Uhlen et al, Advances in Biomagnetic Separation (Eaton Publishing, Natick, 1994); Safarik et al, J. Chromatography B, 722: 33-53 (1999); Miltenyi et al, Cytometry, 11: 231-238 (1990); Nakamura et al, Biotechnol. Prog., 17: 1145-1155 (2001); Moreno et al, Urology, 58: 386-392 (2001); Racila et al, Proc. Natl. Acad. Sci., 95: 4589-4594 (1998); Zigeuner et al, J. Urology, 169: 701-705 (2003); Ghossein et al, Seminars in Surgical Oncology, 20: 304-311 (2001).

The preferred magnetic particles for use in carrying out this invention are particles that behave as colloids. Such particles are characterized by their sub-micron particle size, which is generally less than about 200 nanometers (nm) (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non specific interactions between biological macromolecules found in the sample and the magnetic cores. Such biological macromolecules may include sialic acid residues on the surface of non-target cells, lectins, glyproteins and other membrane components. In addition, the material should contain as much magnetic mass/nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531 and 5,698,271, which patents are incorporated by reference.

Molecular Tags and Cleavable Linkages

Many advantages are provided by measuring complexes using releasable molecular tags, including (1) separation of released molecular tags from an assay mixture provides greatly reduced background and a significant gain in sensitivity; and (2) the use of molecular tags that are specially designed for ease of separation and detection provides a convenient multiplexing capability so that multiple complexes or complex components may be readily measured simultaneously in the same assay. A wide variety of separation techniques may be employed that can distinguish molecules based on one or more physical, chemical, or optical differences among molecules being separated including but not limited to electrophoretic mobility, molecular weight, shape, solubility, pKa, hydrophobicity, charge, charge/mass ratio, polarity, or the like. In one aspect, molecular tags in a plurality or set differ in electrophoretic mobility and optical detection characteristics and are separated by electrophoresis. In another aspect, molecular tags in a plurality or set may differ in molecular weight, shape, solubility, pKa, hydrophobicity, charge, polarity, and are separated by normal phase or reverse phase HPLC, ion exchange HPLC, capillary electrochromatography, mass spectroscopy, gas phase chromatography, or like technique.

Sets of molecular tags are provided that are separated into distinct bands or peaks by a separation technique after they are released from binding compounds. Identification and quantification of such peaks provides a measure or profile of the kinds and amounts of receptor dimers. Molecular tags within a set may be chemically diverse; however, for convenience, sets of molecular tags are usually chemically related. For example, they may all be peptides, or they may consist of different combinations of the same basic building blocks or monomers, or they may be synthesized using the same basic scaffold with different substituent groups for imparting different separation characteristics, as described more fully below. The number of molecular tags in a plurality may vary depending on several factors including the mode of separation employed, the labels used on the molecular tags for detection, the sensitivity of the binding moieties, the efficiency with which the cleavable linkages are cleaved, and the like. In one aspect, the number of molecular tags in a plurality for measuring populations of receptor dimers is in the range of from 2 to 10. In other aspects, the size of the plurality may be in the range of from 2 to 8, 2 to 6, 2 to 4, or 2 to 3.

In an assay, the molecular tags are cleaved by a cleaving agent that reacts with the cleavable linkages to release the molecular tags from their respective binding compounds. The released molecular tags are then separated and detected. A wide variety of cleavable linkages and corresponding cleaving agents may be employed in the invention. Whenever a homogeneous assay format is desired, preferably, the cleaving agent is a locally acting agent. That is, as explained more fully below, a cleavage-inducing moiety is employed in the assay that may be induced to create local conditions for cleavage of the cleavable linkages. In one aspect, such a cleavage-inducing moiety is a sensitizer that generates an active species, as described more fully below. Assays of the invention may also be conducted in a heterogeneous, or non-homogeneous, format. In such a format, binding compounds are combined with a sample in an assay reaction mixture so that the binding compound can specifically bind to their target molecules, or antigenic determinants, whenever they are available to form a stable complexes. Unbound binding compounds are then removed, or separated from, the stable complexes by washing, by filtration, centrifugation, magnetic separation, or the like. In a this format, cleavage of the molecular tags from the stable complexes need not be proximity dependent, since unbound binding compounds have been removed. Therefore, a larger variety of cleavage protocols can be used. Cleavage may still employ a sensitizer, as described above, to cleave an oxidatively labile linkage, but it may also employ various types of chemical, photochemical, or enzymatic cleavage of a variety of cleavable linking groups, such as are known in the art. For example, non-limiting examples of chemically cleavable linkages include disulfides (cleavable by reduction, typically using dithiothreitol), azo groups (cleavable with dithionate), sulfones (cleavable with basic phosphate, with or without dithiothreitol), glycols, cleavable by periodate, and esters, cleavable by hydrolysis. Photolabile linkers include, for example, azo linkages and o-nitrobenzyl ethers.

After washing, the stable complexes of binding compounds and targets may be combined with a solvent into which the molecular tags are released. Depending on the nature of the cleavable bond and the method of cleavage, the solvent may include any additional reagents for the cleavage. Where reagents for cleavage are not required, the solvent is conveniently an separation buffer, such as an electrophoretic separation medium. For example, where the cleavable linkage is photolabile, the medium may be irradiated with light of appropriate wavelength to release the molecular tags into the buffer or medium.

In either format, if the assay reaction conditions interfere with the separation technique employed, it may be necessary to remove, or exchange, the assay reaction buffer prior to cleavage and separation of the molecular tags. For example, in some embodiments, assay conditions include salt concentrations (e.g. required for specific binding) that degrade separation performance when molecular tags are separated on the basis of electrophoretic mobility. In such embodiments, an assay buffer is replaced by a separation buffer, or medium, prior to release and separation of the molecular tags.

Guidance for selecting cleaving agents, molecular tags, cleavable linkages, and other components for homogeneous or heterogeneous assay formats is disclosed in the following references: International patent publications WO 00/66607; WO 01/83502; WO 02/95356; WO 03/06947; and U.S. Pat. Nos. 6,322,980 and 6,514,700.

Assays employing releasable molecular tags and cleaving probes can be made in many different formats and configuations depending on the complexes that are detected or measured. Based on the present disclosure, it is a design choice for one of ordinary skill in the art to select the numbers and specificities of particular binding compounds and cleaving probes.

As mentioned above, an aspect of the invention includes providing mixtures of pluralities of different binding compounds, wherein each different binding compound has one or more molecular tags attached through cleavable linkages. The nature of the binding compound, cleavable linkage and molecular tag may vary widely. A binding compound may comprise an antibody binding composition, an antibody, a peptide, a peptide or non-peptide ligand for a cell surface receptor, a protein, an oligonucleotide, an oligonucleotide analog, such as a peptide nucleic acid, a lectin, or any other molecular entity that is capable of specific binding or stable complex formation with an analyte of interest, such as a complex of proteins. In one aspect, a binding compound, which can be represented by the formula below, comprises one or more molecular tags attached to a binding moiety.

$$B-(L-E)_k$$

wherein B is binding moiety; L is a cleavable linkage; and E is a molecular tag. Preferably, in homogeneous assays for non-polynucleotide analytes, cleavable linkage, L, is an oxidation-labile linkage, and more preferably, it is a linkage that may be cleaved by singlet oxygen. The moiety "-(L-E)$_k$" indicates that a single binding compound may have multiple molecular tags attached via cleavable linkages. In one aspect, k is an integer greater than or equal to one, but in other embodiments, k may be greater than several hundred, e.g. 100 to 500, or k is greater than several hundred to as many as several thousand, e.g. 500 to 5000. Within a composition of the invention, usually each of the plurality of different types of binding compound has a different molecular tag, E. Cleavable linkages, e.g. oxidation-labile linkages, and molecular tags, E, are attached to B by way of conventional chemistries.

Preferably, B is an antibody binding composition. Such compositions are readily formed from a wide variety of commercially available antibodies, both monoclonal and polyclonal, specific for proteins of interest. In particular, antibodies specific for epidermal growth factor receptors are disclosed in the following patents, which are incorporated by references: U.S. Pat. Nos. 5,677,171; 5,772,997; 5,968,511; 5,480,968; 5,811,098. U.S. Pat. No. 6,488,390, incorporated herein by reference, discloses antibodies specific for a G-protein coupled receptor, CCR4. U.S. Pat. No. 5,599,681, incorporated herein by reference, discloses antibodies specific for phosphorylation sites of proteins. Commercial vendors, such as Cell Signaling Technology (Beverly, Mass.), Biosource International (Camarillo, Calif.), and Upstate (Charlottesville, Va.), also provide monoclonal and polyclonal antibodies specific for many hundreds of proteins of biological and medical interest, including proteins listed in Table II.

When L is oxidation labile, L is preferably a thioether or its selenium analog; or an olefin, which contains carbon-carbon double bonds, wherein cleavage of a double bond to an oxo group, releases the molecular tag, E. Illustrative thioether bonds are disclosed in Willner et al, U.S. Pat. No. 5,622,929 which is incorporated by reference. Illustrative olefins include vinyl sulfides, vinyl ethers, enamines, imines substituted at the carbon atoms with an α-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C., by reaction with acid or base, or by photo-activation in the absence or presence of a photosensitizer. Such reactions are described in the following exemplary references: Adam and Liu, J. Amer. Chem. Soc. 94, 1206-1209, 1972, Ando, et al., J.C.S. Chem. Comm. 1972, 477-8, Ando, et al., Tetrahedron 29, 1507-13, 1973, Ando, et al., J. Amer. Chem. Soc. 96, 6766-8, 1974, Ando and Migita, ibid. 97, 5028-9, 1975, Wasserman and Terao, Tetra. Lett. 21, 1735-38, 1975, Ando and Watanabe, ibid. 47, 4127-30, 1975, Zaklika, et al., Photochemistry and Photobiology 30, 35-44, 1979, and Adam, et al., Tetra. Lett. 36, 7853-4, 1995. See also, U.S. Pat. No. 5,756,726.

The formation of dioxetanes is obtained by the reaction of singlet oxygen with an activated olefin substituted with an molecular tag at one carbon atom and the binding moiety at the other carbon atom of the olefin. See, for example, U.S. Pat. No. 5,807,675. These cleavable linkages may be depicted by the following formula:

—W—(X)$_n$C$_\alpha$=C$_\beta$(Y)(Z)- wherein:

W may be a bond, a heteroatom, e.g., O, S, N, P, M (intending a metal that forms a stable covalent bond), or a functionality, such as carbonyl, imino, etc., and may be bonded to X or C$_\alpha$; at least one X will be aliphatic, aromatic, alicyclic or heterocyclic and bonded to C$_\alpha$ through a hetero atom, e.g., N, O, or S and the other X may be the same or different and may in addition be hydrogen, aliphatic, aromatic, alicyclic or heterocyclic, usually being aromatic or aromatic heterocyclic wherein one X may be taken together with Y to form a ring, usually a heterocyclic ring, with the carbon atoms to which they are attached, generally when other than hydrogen being from about 1 to 20, usually 1 to 12, more usually 1 to 8 carbon atoms and one X will have 0 to 6, usually 0 to 4 heteroatoms, while the other X will have at least one heteroatom and up to 6 heteroatoms, usually 1 to 4 heteroatoms;

Y will come within the definition of X, usually being bonded to C$_\beta$ through a heteroatom and as indicated may be taken together with X to form a heterocyclic ring;

Z will usually be aromatic, including heterocyclic aromatic, of from about 4 to 12, usually 4 to 10 carbon atoms and 0 to 4 heteroatoms, as described above, being bonded directly to C$_\beta$ or through a heteroatom, as described above;

n is 1 or 2, depending upon whether the molecular tag is bonded to C$_\alpha$ or X; wherein one of Y and Z will have a functionality for binding to the binding moiety, or be bound to the binding moiety, e.g. by serving as, or including a linkage group, to a binding moiety, T. Preferably, W, X, Y, and Z are selected so that upon cleavage molecular tag, E, is within the size limits described below.

Illustrative cleavable linkages include S(molecular tag)-3-thiolacrylic acid, N(molecular tag), N-methyl 4-amino-4-butenoic acid, 3-hydroxyacrolein, N-(4-carboxyphenyl)-2-(molecular tag)-imidazole, oxazole, and thiazole.

Also of interest are N-alkyl acridinyl derivatives, substituted at the 9 position with a divalent group of the formula:

—(CO)X$^1$(A)- wherein:

X$^1$ is a heteroatom selected from the group consisting of O, S, N, and Se, usually one of the first three; and A is a chain of at least 2 carbon atoms and usually not more than 6 carbon atoms substituted with an molecular tag, where preferably the other valences of A are satisfied by hydrogen, although the chain may be substituted with other groups, such as alkyl, aryl, heterocyclic groups, etc., A generally being not more than 10 carbon atoms.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the molecular tag.

Also of interest are tellurium (Te) derivatives, where the Te is bonded to an ethylene group having a hydrogen atom β to the Te atom, wherein the ethylene group is part of an alicyclic or heterocyclic ring, that may have an oxo group, preferably fused to an aromatic ring and the other valence of the Te is bonded to the molecular tag. The rings may be coumarin, benzoxazine, tetralin, etc.

Figure 3A:
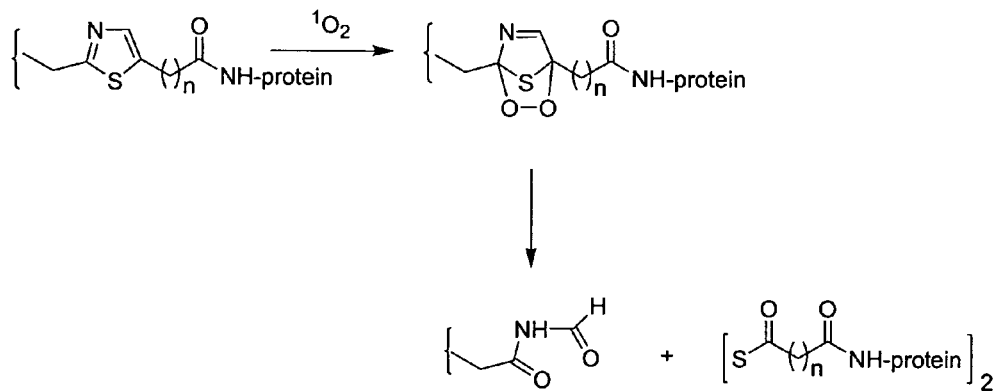
FIGS. 3A-3F illustrate oxidation-labile linkages and their respective cleavage reactions mediated by singlet oxygen.
Figure 3B:
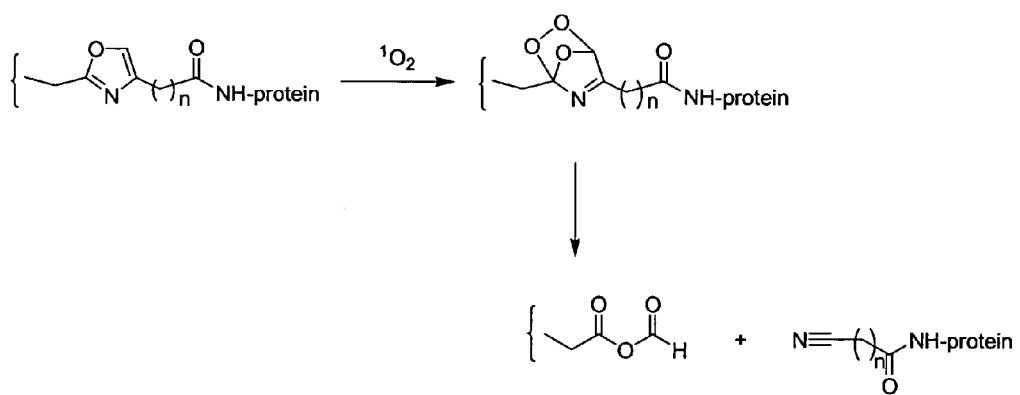
Figure 3C:
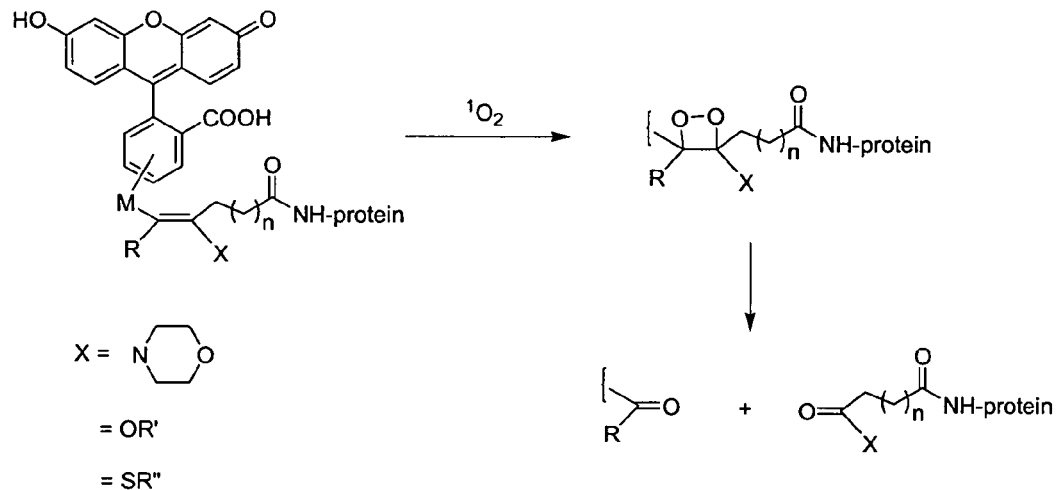
Figure 3D:
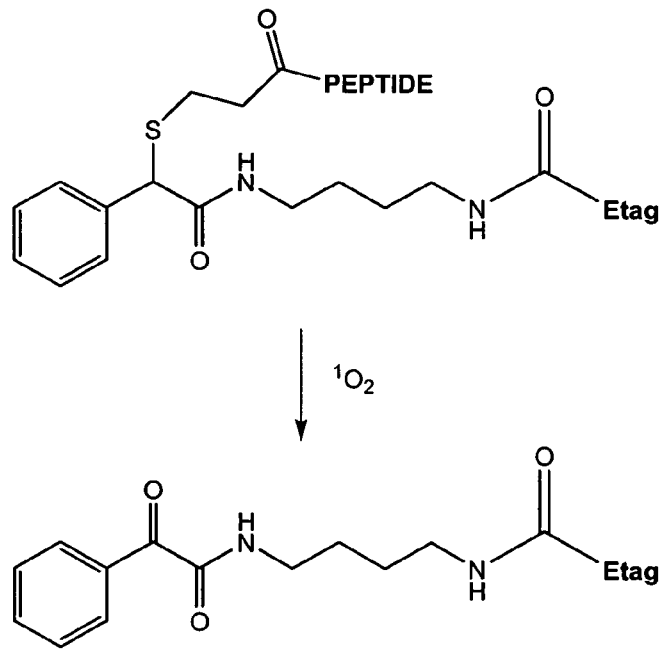
Figure 3E:
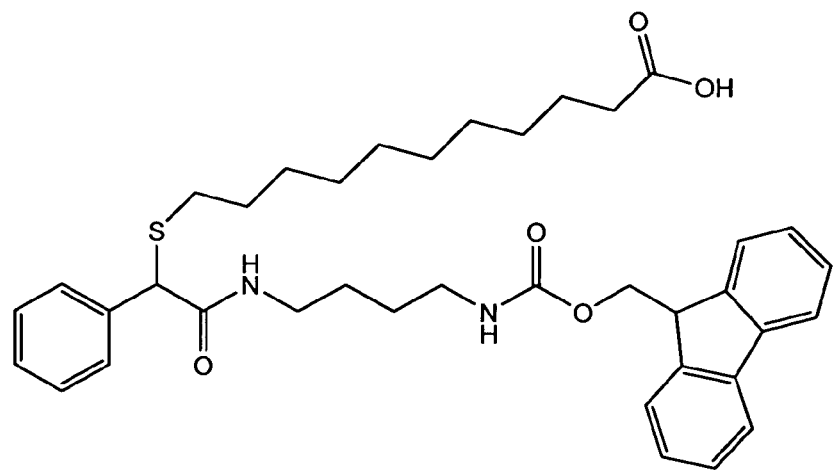
Figure 3F:
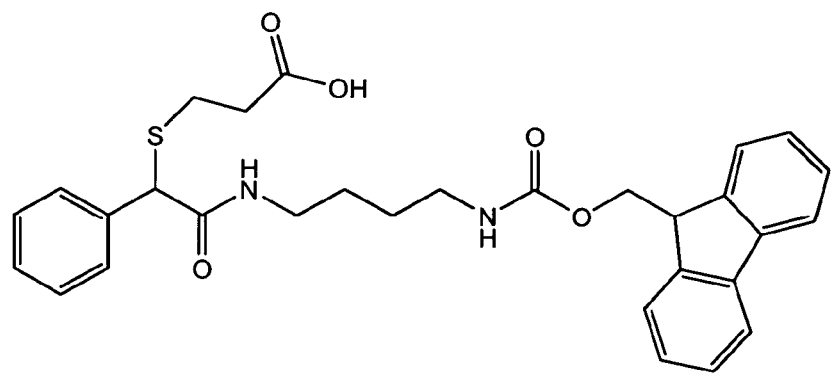
Figure 4A:
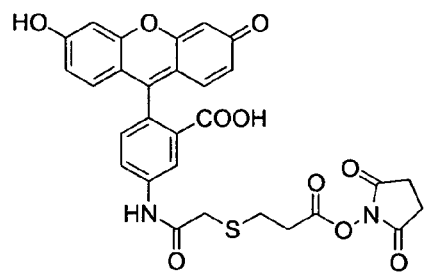
FIGS. 4A-4J show the structures of tags that have been designed and synthesized.
Figure 4A:
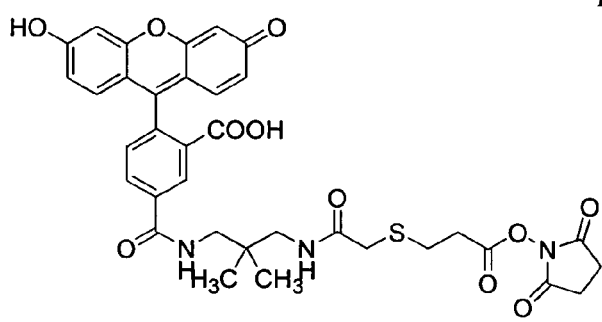
Figure 4A:
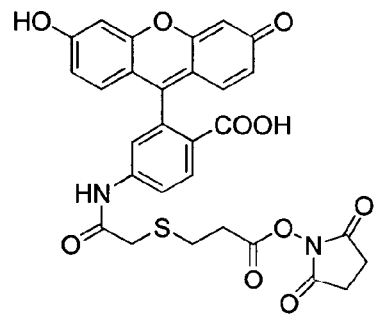
Figure 4A:
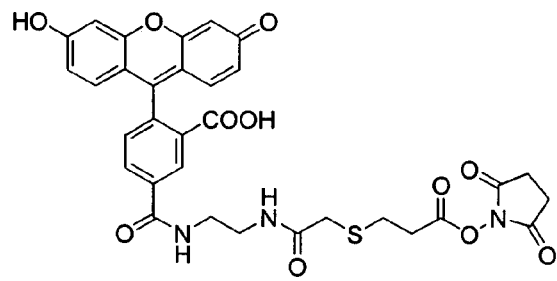
Figure 4B:
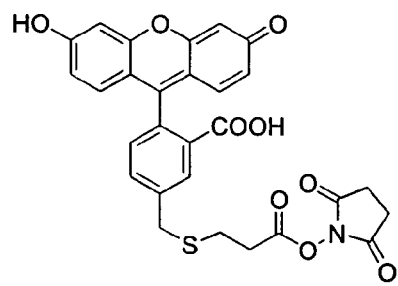
Figure 4B:
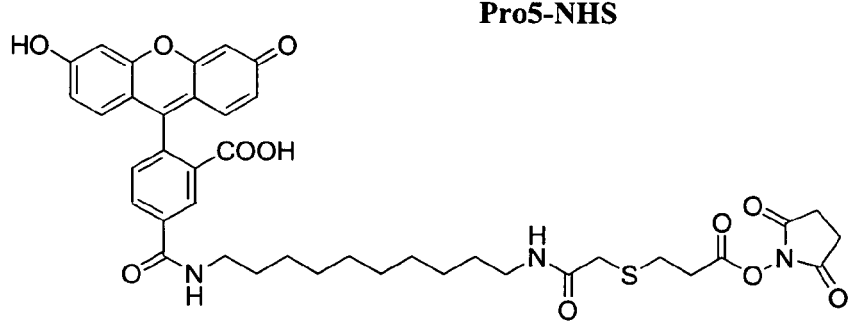
Figure 4B:
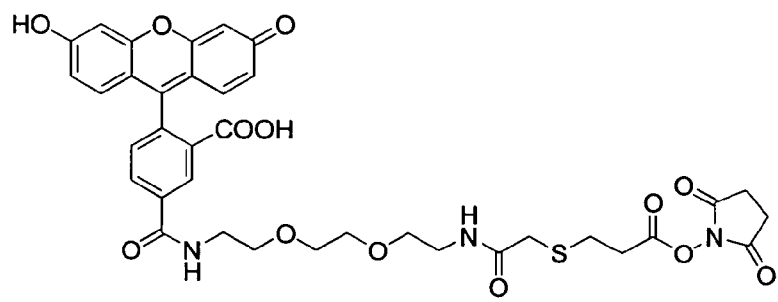
Figure 4B:
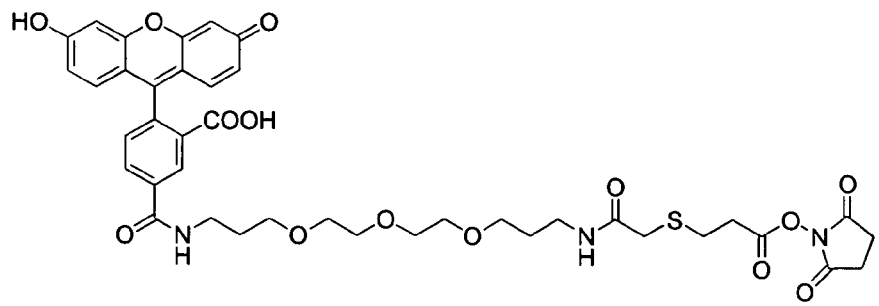
Figure 4C:
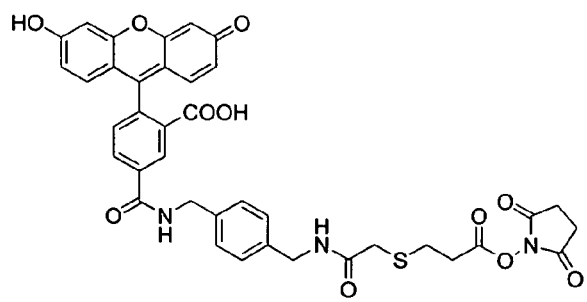
Figure 4C:
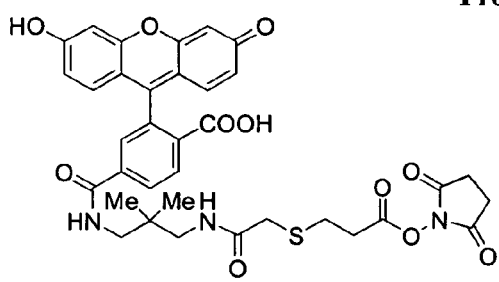
Figure 4C:
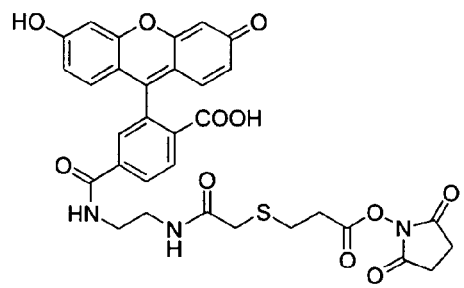
Figure 4C:
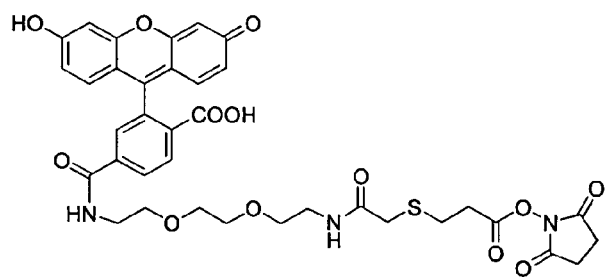
Figure 4D:
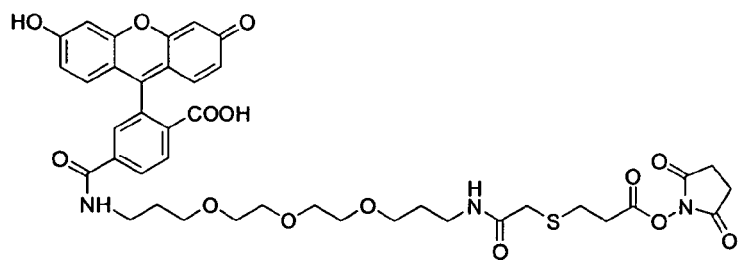
Figure 4D:
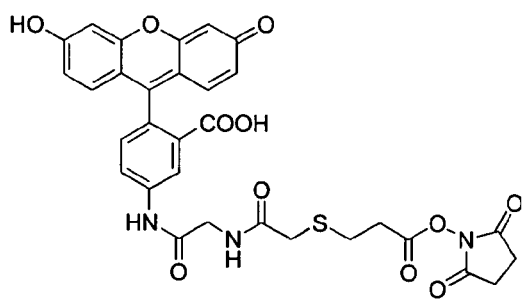
Figure 4D:
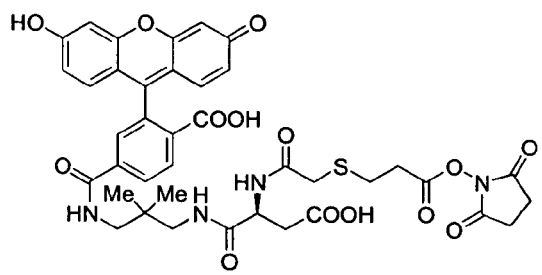
Figure 4D:
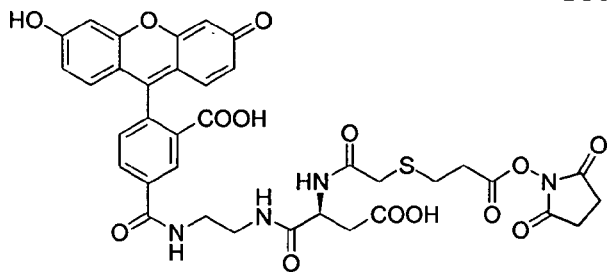
Figure 4E:
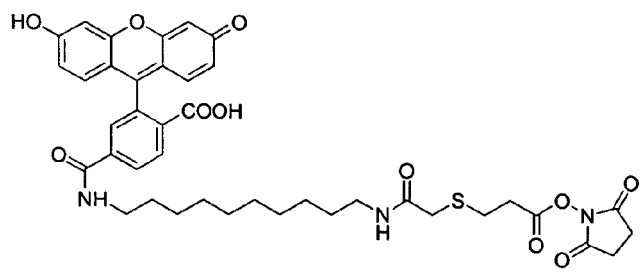
Figure 4E:
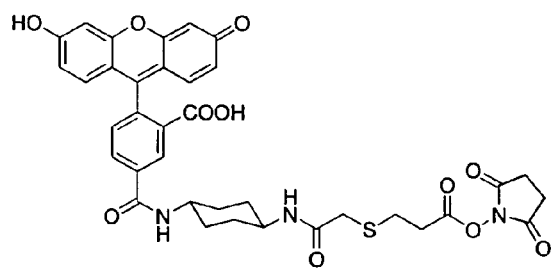
Figure 4E:
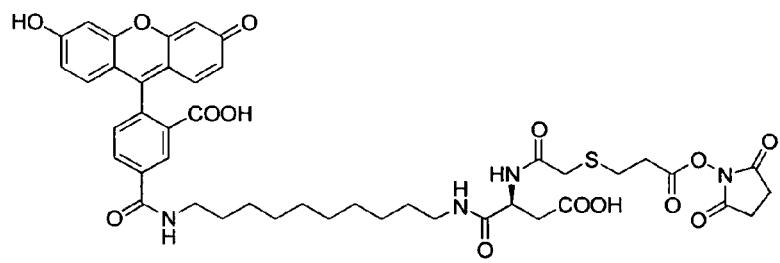
Figure 4E:
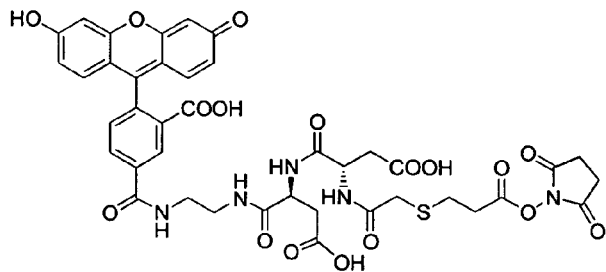
Figure 4F:
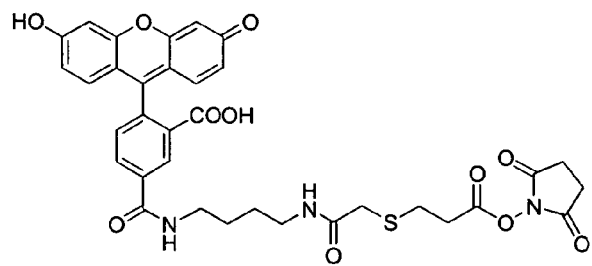
Figure 4F:
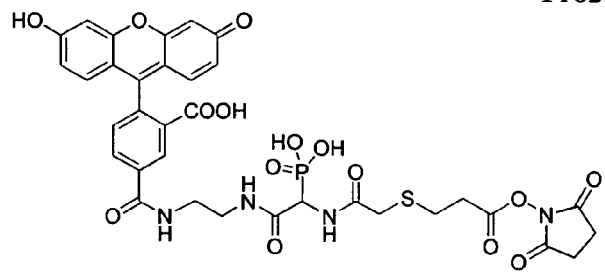
Figure 4F:
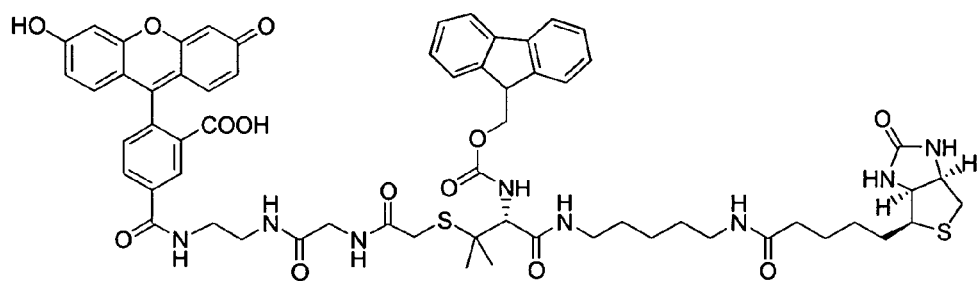
Figure 4F:
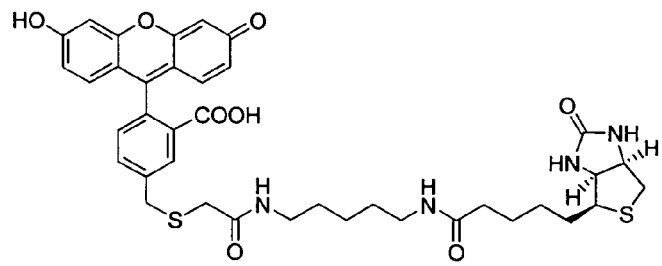
Figure 4G:
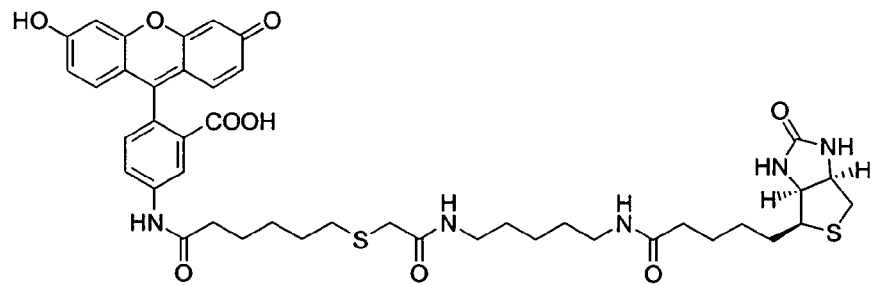
Figure 4G:
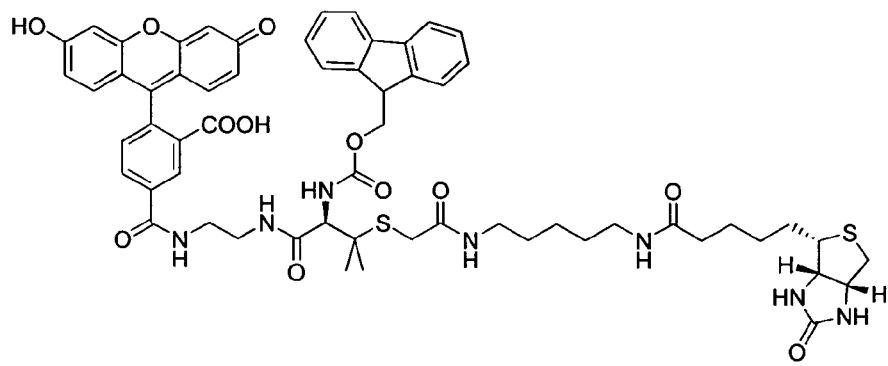
Figure 4G:
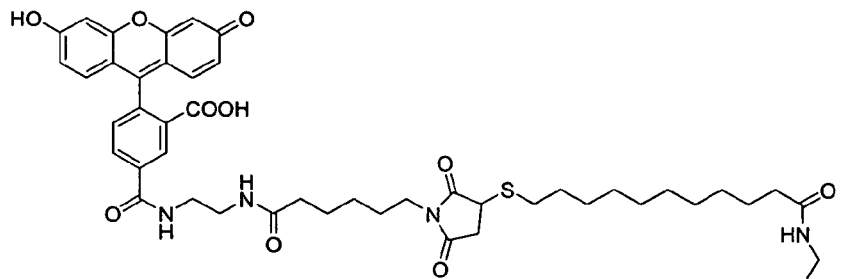
Figure 4G:
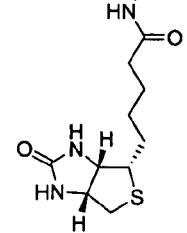
Figure 4H:
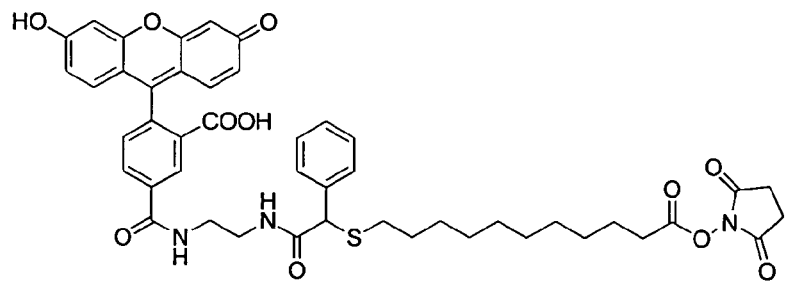
Figure 4H:
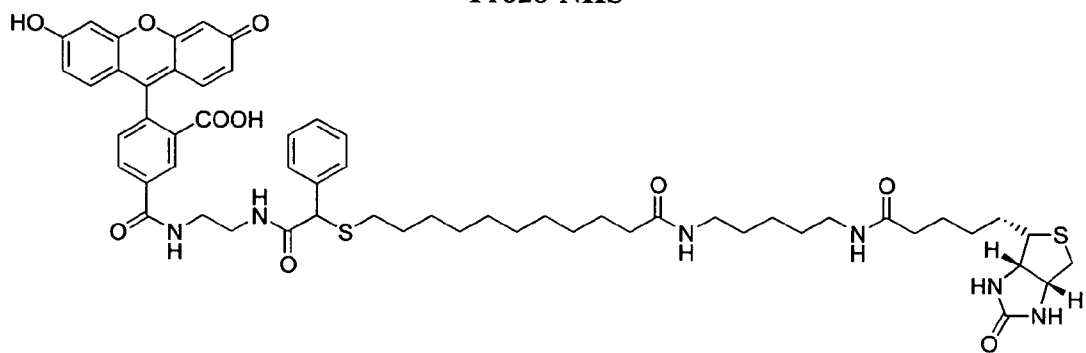
Figure 4H:
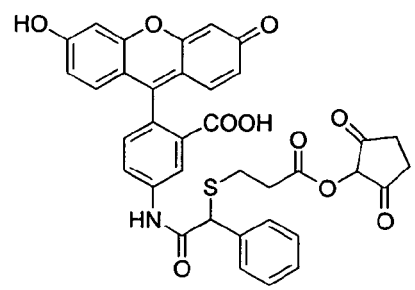
Figure 4H:
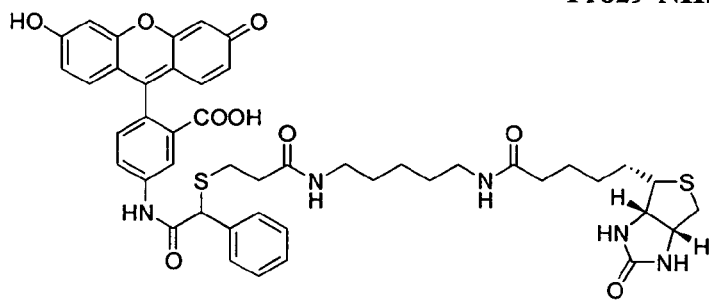
Figure 4I:
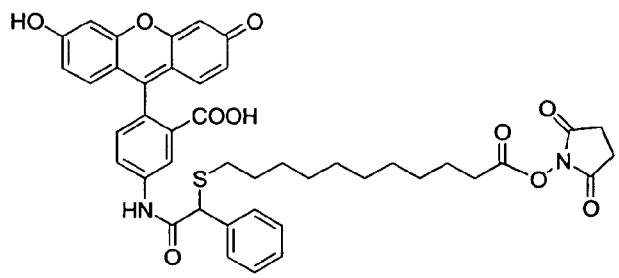
Figure 4I:
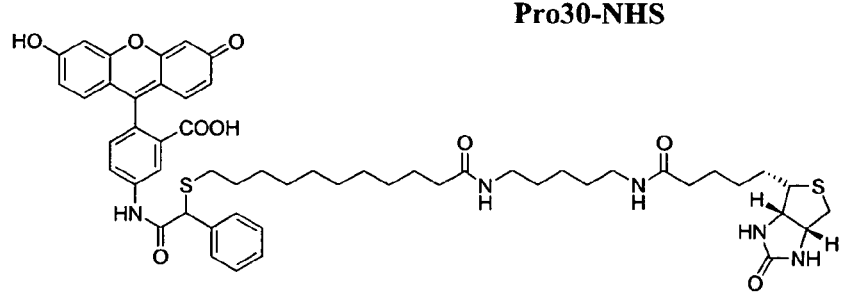
Figure 4I:
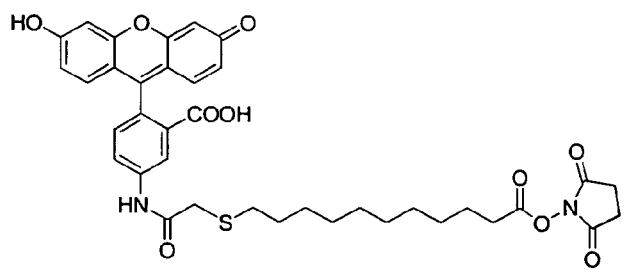
Figure 4I:
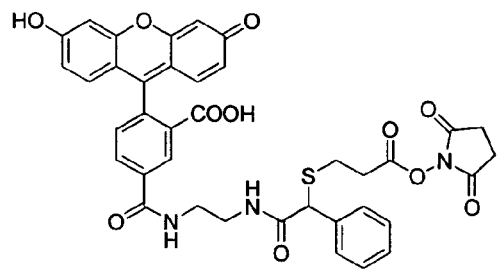
Figure 4J:
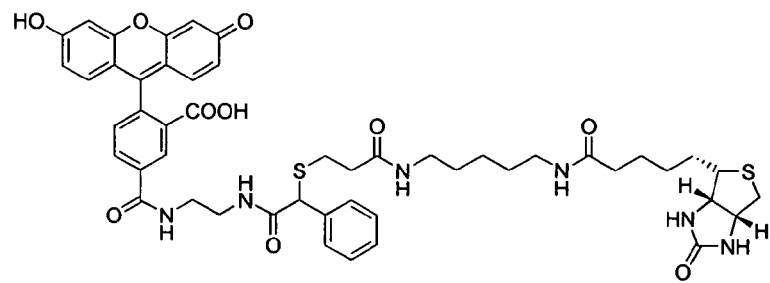
Figure 4J:
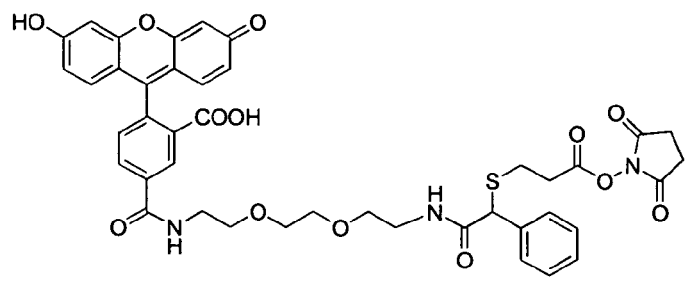
Figure 4J:
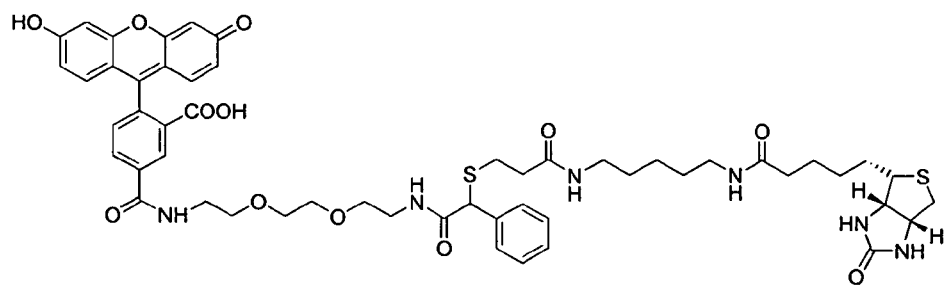
Figure 5A:
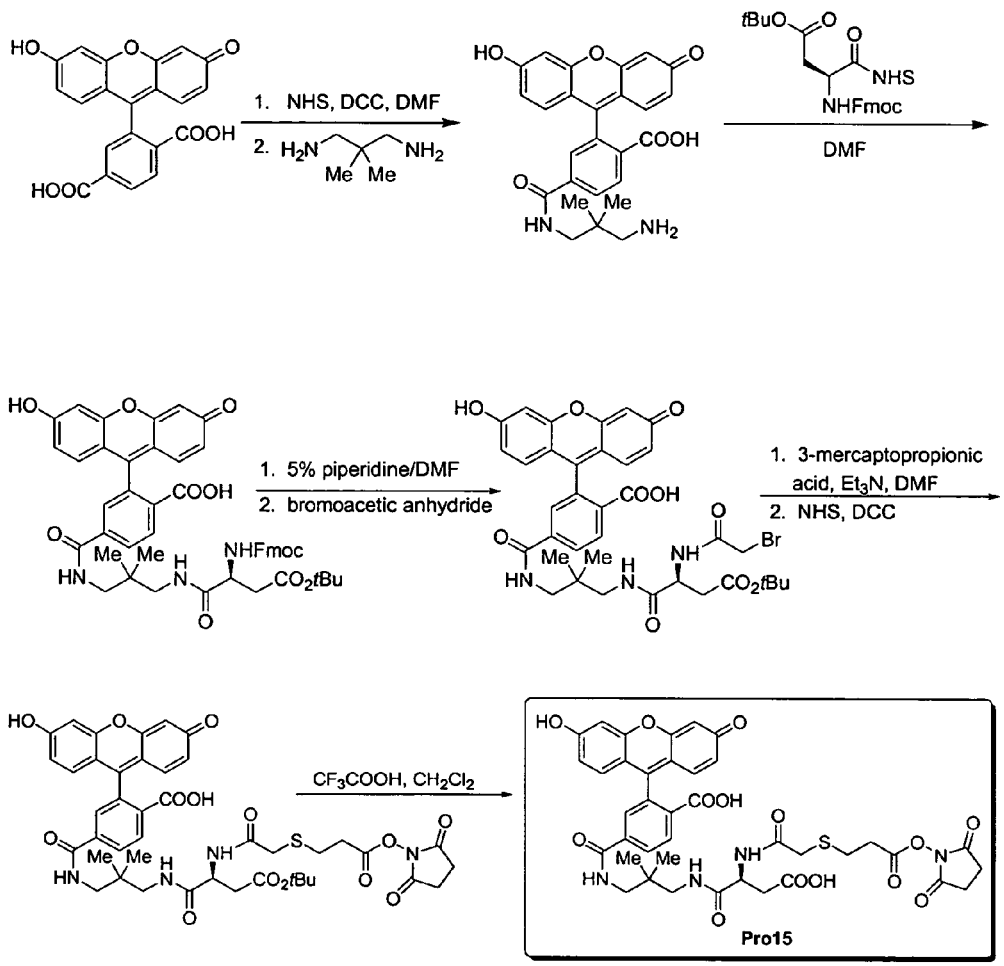
FIGS. 5A-5D illustrate the chemistries of synthesis of the tag moieties illustrated in FIG. 6.
Figure 5B:
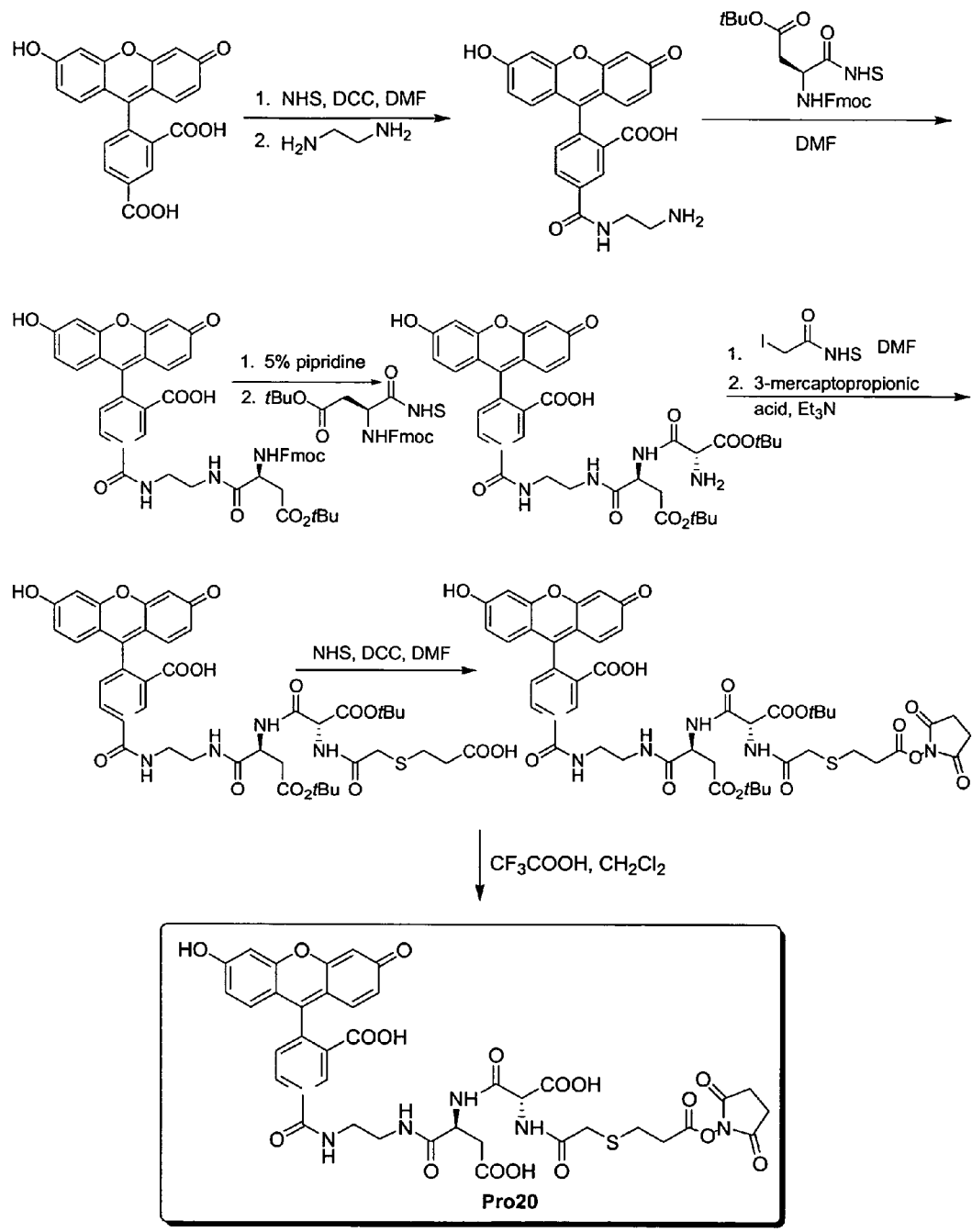
Figure 5C:
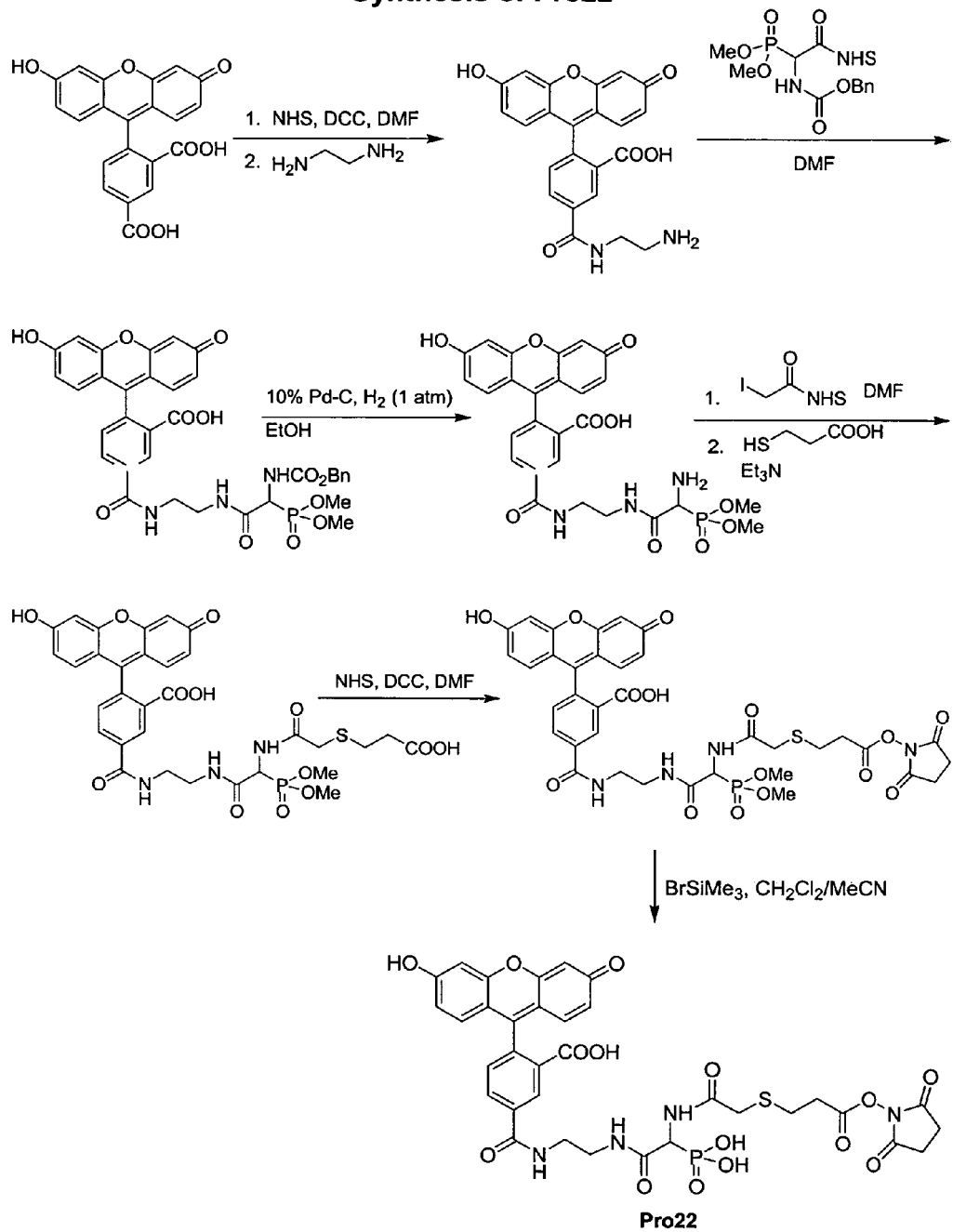
Figure 5D:
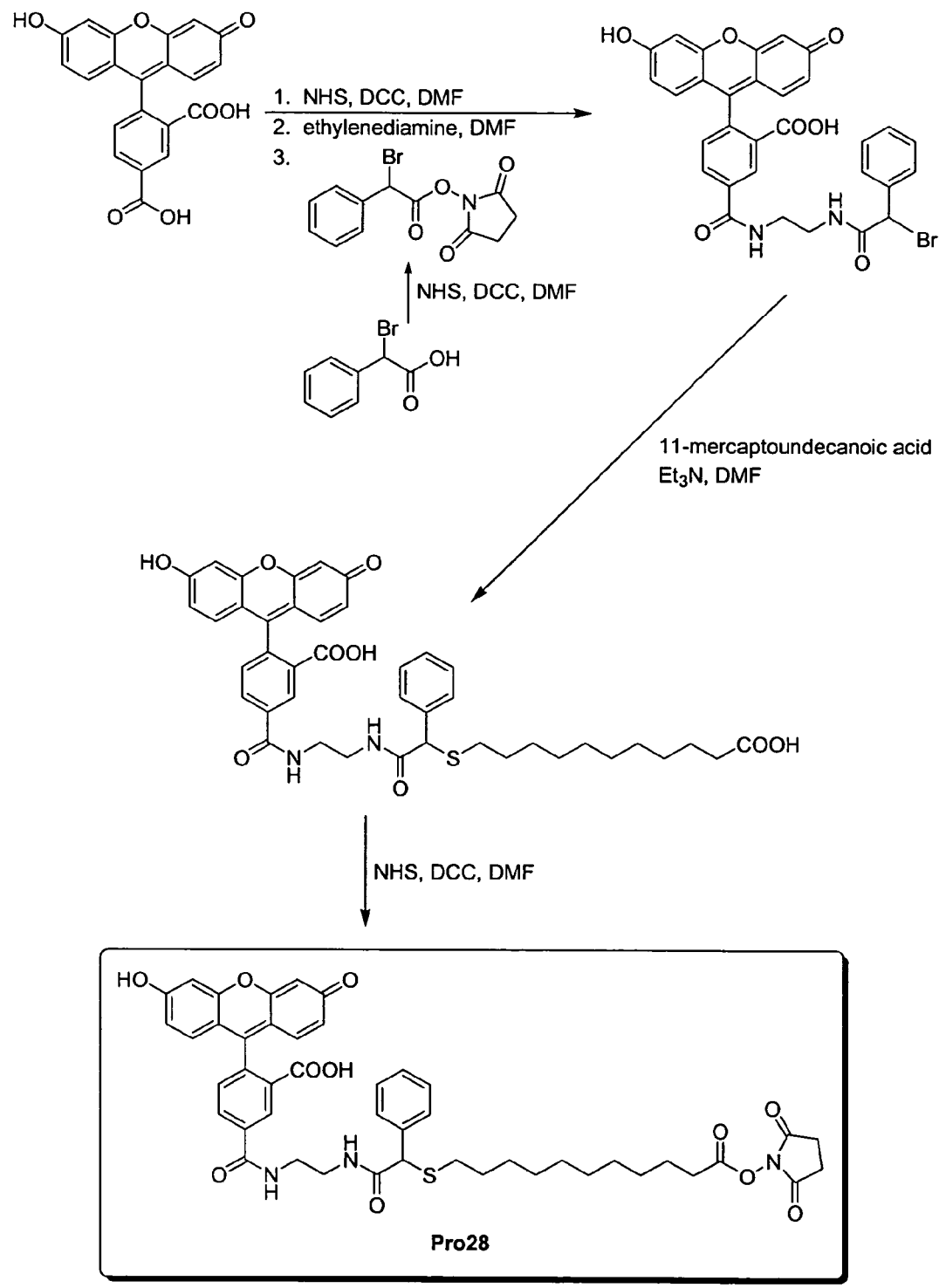

Several preferred cleavable linkages and their cleavage products are illustrated in FIGS. 3A-F. The thiazole cleavable linkage, "—CH$_2$-thiazole-(CH2)$_n$-C(=O)—NH-protein," shown in FIG. 3A, results in an molecular tag with the moiety "—CH$_2$—C(=O)—NH—CHO." Preferably, n is in the range of from 1 to 12, and more preferably, from 1 to 6. The oxazole cleavable linkage, "—CH$_2$-oxazole-(CH2)$_n$-C(=O)—NH-protein," shown in FIG. 3B, results in an molecular tag with the moiety "—CH$_2$—C(=O)O—CHO." An olefin cleavable linkage (FIG. 3C) is shown in connection with the binding compound embodiment "B-L-M-D," described above and with D being a fluorescein dye. The olefin cleavable linkage may be employed in other embodiments also. Cleavage of the illustrated olefin linkage results in an molecular tag of the form: "R—(C=O)-M-D," where "R" may be any substituent within the general description of the molecular tags, E, provided above. Preferably, R is an electron-donating group, e.g. Ullman et al, U.S. Pat. No. 6,251,581; Smith and March, March's Advanced Organic Chemistry: Reactions, Mechanisms, and Structure, 5$^{th}$ Edition (Wiley-Interscience, New York, 2001); and the like. More preferably, R is an electron-donating group having from 1-8 carbon atoms and from 0 to 4 heteroatoms selected from the group consisting of O, S, and N. In further preference, R is —N(Q)$_2$, —OQ, p-[C$_6$H$_4$N(Q)$_2$], furanyl, n-alkylpyrrolyl, 2-indolyl, or the like, where Q is alkyl or aryl. In further reference to the olefin cleavable linkage of FIG. 3C, substituents "X" and "R" are equivalent to substituents "X" and "Y" of the above formula describing cleavable linkage, L. In particular, X in FIG. 3C is preferably morpholino, —OR', or —SR", where R' and R" are aliphatic, aromatic, alicyclic or heterocyclic having from 1 to 8 carbon atoms and 0 to 4 heteroatoms selected from the group consisting of O, S, and N. A preferred thioether cleavable linkage is illustrated in FIG. 3D having the form "—(CH$_2$)$_2$-S—CH(C$_6$H$_5$)C(=O)NH—(CH$_2$)$_n$—NH—," wherein n is in the range of from 2 to 12, and more preferably, in the range of from 2 to 6. Thioether cleavable linkages of the type shown in FIG. 3D may be attached to binding moieties, T, and molecular tags, E, by way of precursor compounds shown in FIGS. 3E and 3F. To attach to an amino group of a binding moiety, T, the terminal hydroxyl is converted to an NHS ester by conventional chemistry. After reaction with the amino group and attachment, the Fmoc protection group is removed to produce a free amine which is then reacted with an NHS ester of the molecular tag.

Molecular tag, E, in the present invention may comprise an electrophoric tag as described in the following references when separation of pluralities of molecular tags are carried out by gas chromatography or mass spectrometry: Zhang et al, Bioconjugate Chem., 13: 1002-1012 (2002); Giese, Anal. Chem., 2: 165-168 (1983); and U.S. Pat. Nos. 4,650,750; 5,360,819; 5,516,931; 5,602,273; and the like.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of from about 50 to about 2500 daltons, more preferably, from about 50 to about 1500 daltons. Preferred structures of E are described more fully below. E may comprise a detection group for generating an electrochemical, fluorescent, or chromogenic signal. In embodiments employing detection by mass, E may not have a separate moiety for detection purposes. Preferably, the detection group generates a fluorescent signal.

Molecular tags within a plurality are selected so that each has a unique separation characteristic and/or a unique optical property with respect to the other members of the same plurality. In one aspect, the chromatographic or electrophoretic separation characteristic is retention time under set of standard separation conditions conventional in the art, e.g. voltage, column pressure, column type, mobile phase, electrophoretic separation medium, or the like. In another aspect, the optical property is a fluorescence property, such as emission spectrum, fluorescence lifetime, fluorescence intensity at a given wavelength or band of wavelengths, or the like. Preferably, the fluorescence property is fluorescence intensity. For example, each molecular tag of a plurality may have the same fluorescent emission properties, but each will differ from one another by virtue of a unique retention time. On the other hand, or two or more of the molecular tags of a plurality may have identical retention times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by conventional capillary electrophoresis apparatus, either in the presence or absence of a conventional sieving matrix. Exemplary capillary electrophoresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more. Preferably, in such conventional apparatus, the electrophoretic mobilities of molecular tags of a plurality differ by at least one percent, and more preferably, by at least a percentage in the range of from 1 to 10 percent.

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "B-L-(M, D)" designates binding compound of either of two forms: "B-L-M-D" or "B-L-D-M."

Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, $8^{th}$ ed., (Molecular Probes, Eugene, 2002); Lee et al, U.S. Pat. No. 6,191,278; Lee et al, U.S. Pat. No. 6,372,907; Menchen et al, U.S. Pat. No. 6,096,723; Lee et al, U.S. Pat. No. 5,945,526; Lee et al, Nucleic Acids Research, 25: 2816-2822 (1997); Hobb, Jr., U.S. Pat. No. 4,997,928; Khanna et al., U.S. Pat. No. 4,318,846; Reynolds, U.S. Pat. No. 3,932,415; Eckert et al, U.S. Pat. No. 2,153,059; Eckert et al, U.S. Pat. No. 2,242,572; Taing et al, International patent publication WO 02/30944; and the like. Further specific exemplary fluorescent dyes include 5- and 6-carboxyrhodamine 6G; 5- and 6-carboxy-X-rhodamine, 5- and 6-carboxytetramethylrhodamine, 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein. Most preferably, D is a fluorescein or a fluorescein derivative.

The size and composition of mobility-modifying moiety, M, can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mobility-modifying moiety has from about 0 to about 40, more usually from about 0 to about 30 heteroatoms, which in addition to the heteroatoms indicated above may include halogen or other heteroatom. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric, nitrous, etc. For positive charges, substituents include amino (includes ammonium), phosphonium, sulfonium, oxonium, etc., where substituents are generally aliphatic of from about 1-6 carbon atoms, the total number of carbon atoms per heteroatom, usually be less than about 12, usually less than about 9. The side chains include amines, ammonium salts, hydroxyl groups, including phenolic groups, carboxyl groups, esters, amides, phosphates, heterocycles. M may be a homo-oligomer or a hetero-oligomer, having different monomers of the same or different chemical characteristics, e.g., nucleotides and amino acids.

In another aspect, (M,D) moieties are constructed from chemical scaffolds used in the generation of combinatorial libraries. For example, the following references describe scaffold compound useful in generating diverse mobility modifying moieties: peptoids (PCT Publication No WO 91/19735, Dec. 26, 1991), encoded peptides (PCT Publication WO 93/20242, Oct. 14 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. U.S.A. 90: 6909-6913 (1993), vinylogous polypeptides (Hagihara et al. J.Amer. Chem. Soc. 114: 6568 (1992)), nonpeptidal peptidomimetics with a Beta-D-Glucose scaffolding (Hirschmann, R. et al., J.Amer. Chem. Soc. 114: 9217-9218 (1992)), analogous organic syntheses of small compound libraries (Chen, C. et al. J.Amer. Chem. Soc. 116: 2661(1994)), oligocarbamates (Cho, C. Y. et al. Science 261: 1303(1993)), peptidyl phosphonates (Campbell, D. A. et al., J. Org. Chem. 59:658(1994)); Cheng et al, U.S. Pat. No. 6,245,937; Heizmann et al, "Xanthines as a scaffold for molecular diversity," Mol. Divers. 2: 171-174 (1997); Pavia et al, Bioorg. Med. Chem., 4: 659-666 (1996); Ostresh et al, U.S. Pat. No. 5,856,107; Gordon, E. M. et al., J. Med. Chem. 37: 1385 (1994); and the like. Preferably, in this aspect, D is a substituent on a scaffold and M is the rest of the scaffold.

M may also comprise polymer chains prepared by known polymer subunit synthesis methods. Methods of forming selected-length polyethylene oxide-containing chains are well known, e.g. Grossman et al, U.S. Pat. No. 5,777,096. It can be appreciated that these methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid, polylactic acid), polypeptides, oligosaccharides, polyurethanes, polyamides, polysulfonamides, polysulfoxides, polyphosphonates, and block copolymers thereof, including polymers composed of units of multiple subunits linked by charged or uncharged linking groups. In addition to homopolymers, the polymer chains used in accordance with the invention include selected-length copolymers, e.g., copolymers of polyethylene oxide units alternating with polypropylene units. As another example, polypeptides of selected lengths and amino acid composition (i.e., containing naturally occurring or man-made amino acid residues), as homopolymers or mixed polymers.

In another aspect, after release, molecular tag, E, is defined by the formula:

A-M-D wherein:

A is —C(=O)R, where R is aliphatic, aromatic, alicyclic or heterocyclic having from 1 to 8 carbon atoms and 0 to 4 heteroatoms selected from the group consisting of O, S. and N; —CH$_2$—C(=O)—NH—CHO; —SO$_2$H; —CH$_2$—C(=O)O—CHO; —C(=O)NH—(CH$_2$)$_n$—NH—C(=O)C(=O)—(C$_6$H$_5$), where n is in the range of from 2 to 12;

D is a detection group, preferably a fluorescent dye; and

M is as described above, with the proviso that the total molecular weight of A-M-D be within the range of from about 100 to about 2500 daltons.

In another aspect, D is a fluorescein and the total molecular weight of A-M-D is in the range of from about 100 to about 1500 daltons.

In another aspect, M may be synthesized from smaller molecules that have functional groups that provide for linking of the molecules to one another, usually in a linear chain. Such functional groups include carboxylic acids, amines, and hydroxy- or thiol-groups. In accordance with the present invention the charge-imparting moiety may have one or more side groups pending from the core chain. The side groups have a functionality to provide for linking to a label or to another molecule of the charge-imparting moiety. Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g., sulfonate, phosphate esters, sulfonamides, thioesters, etc., and the like.

Attaching Molecular Tags to Binding Moieties

Extensive guidance can be found in the literature for covalently linking molecular tags to binding compounds, such as antibodies, e.g. Hermanson, Bioconjugate Techniques, (Academic Press, New York, 1996), and the like. In one aspect of the invention, one or more molecular tags are attached directly or indirectly to common reactive groups on a binding compound. Common reactive groups include amine, thiol, carboxylate, hydroxyl, aldehyde, ketone, and the like, and may be coupled to molecular tags by commercially available cross-linking agents, e.g. Hermanson (cited above); Haugland, Handbook of Fluorescent Probes and Research Products, Ninth Edition (Molecular Probes, Eugene, Oreg., 2002). In one embodiment, an NHS-ester of a molecular tag is reacted with a free amine on the binding compound.

Figure 2A:
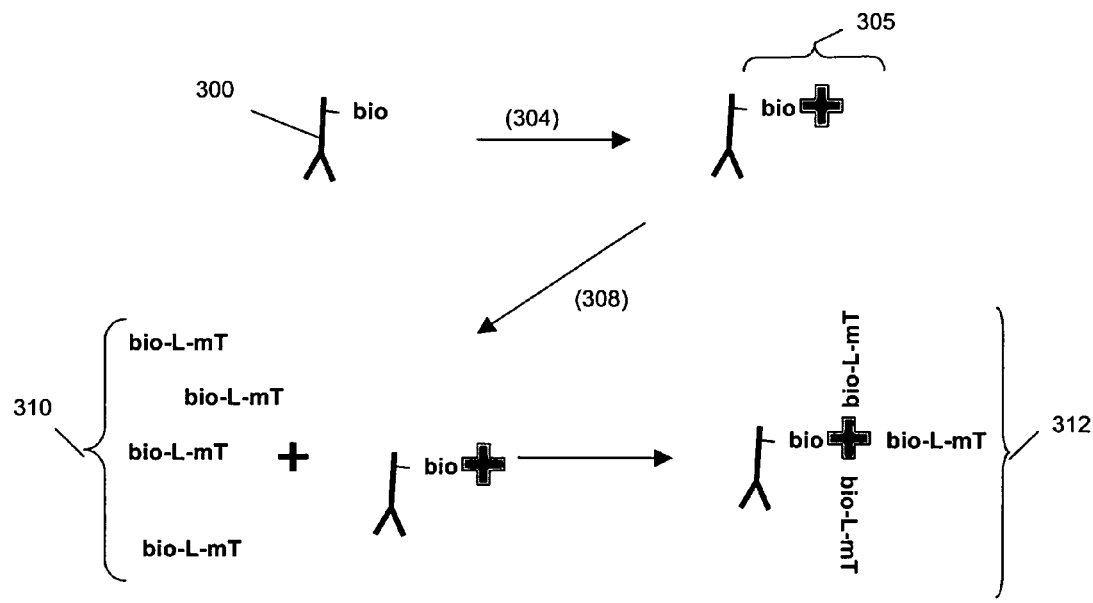
FIGS. 2A-2E illustrate diagrammatically methods for attaching molecular tags to antibodies.

In another embodiment illustrated in FIG. 2A, binding compounds comprise a biotinylated antibody (200) as a binding moiety. Molecular tags are attached to binding moiety (200) by way of avidin or streptavidin bridge (206). Preferably, in operation, binding moiety (200) is first reacted with a target complex, after which avidin or streptavidin is added (204) to form antibody-biotin-avidin complex (205). To such complexes (205) are added (208) biotinylated molecular tags (210) to form binding compound (212).

Figure 2B:
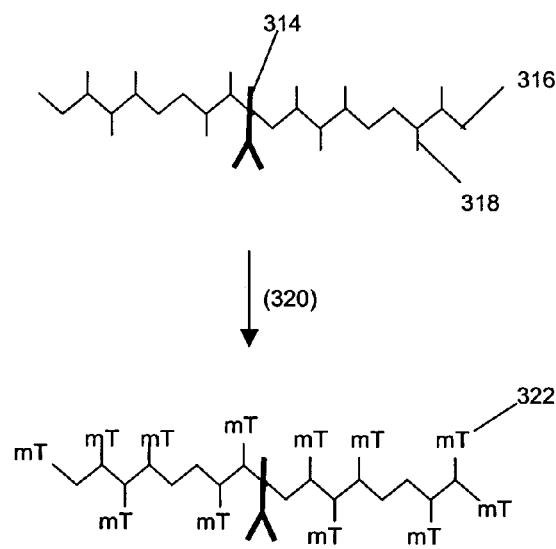

In still another embodiment illustrated in FIG. 2B, binding compounds comprise an antibody (214) derivatized with a multi-functional moiety (216) that contains multiple functional groups (218) that are reacted (220) molecular tag precursors to give a final binding compound having multiple molecular tags (222) attached. Exemplary multi-functional moieties include aminodextran, and like materials.

Once each of the binding compounds is separately derivatized by a different molecular tag, it is pooled with other binding compounds to form a plurality of binding compounds. Usually, each different kind of binding compound is present in a composition in the same proportion; however, proportions may be varied as a design choice so that one or a subset of particular binding compounds are present in greater or lower proportion depending on the desirability or requirements for a particular embodiment; or assay. Factors that may affect such design choices include, but are not limited to, antibody affinity and avidity for a particular target, relative prevalence of a target, fluorescent characteristics of a detection moiety of a molecular tag, and the like.

Cleavage-Inducing Moiety Producing Active Species

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226-241 (2000).

An important consideration for the cleavage-inducing moiety and the cleavable linkage is that they not be so far removed from one another when bound to a target protein that the active species generated by the sensitizer diffuses and loses its activity before it can interact with the cleavable linkage. Accordingly, a cleavable linkage preferably are within 1000 nm, preferably 20-200 nm of a bound cleavage-inducing moiety. This effective range of a cleavage-inducing moiety is referred to herein as its "effective proximity."

Generators of active species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al, FEBS Lett., 355: 287 (1994) (peroxidases and oxygenases); Kanofsky, J.Biol. Chem. 258: 5991-5993 (1983)(lactoperoxidase); Pierlot et al, Meth. Enzymol., 319: 3-20 (2000)(thermal lysis of endoperoxides); and the like.

Attachment of a binding agent to the cleavage-inducing moiety may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245:3059 (1970). A wide variety of functional groups are available or can be incorporated. Functional groups include carboxylic acids, aldehydes, amino groups, cyano groups, ethylene groups, hydroxyl groups, mercapto groups, and the like. The manner of linking a wide variety of compounds is well known and is amply illustrated in the literature (see above). The length of a linking group to a binding agent may vary widely, depending upon the nature of the compound being linked, the effect of the distance on the specific binding properties and the like.

It may be desirable to have multiple cleavage-inducing moieties attached to a binding agent to increase, for example, the number of active species generated. This can be accomplished with a polyfunctional material, normally polymeric, having a plurality of functional groups, e.g., hydroxy, amino, mercapto, carboxy, ethylenic, aldehyde, etc., as sites for linking. Alternatively a support may be used. The support can have any of a number of shapes, such as particle including bead, film, membrane, tube, well, strip, rod, and the like. For supports in which photosensitizer is incorporated, the surface of the support is, preferably, hydrophilic or capable of being rendered hydrophilic and the body of the support is, preferably, hydrophobic. The support may be suspendable in the medium in which it is employed. Examples of suspendable supports, by way of illustration and not limitation, are polymeric materials such as latex, lipid bilayers, oil droplets, cells and hydrogels. Other support compositions include glass, metals, polymers, such as nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, poly (vinyl butyrate), etc.; either used by themselves or in conjunction with other materials. Attachment of binding agents to the support may be direct or indirect, covalent or non-covalent and can be accomplished by well-known techniques, commonly available in the literature as discussed above. See, for example, "Immobilized Enzymes," Ichiro Chibata, supra. The surface of the support will usually be polyfunctional or be capable of being polyfunctionalized or be capable of binding to a target-binding moiety, or the like, through covalent or specific or non-specific non-covalent interactions.

The cleavage-inducing moiety may be associated with the support by being covalently or non-covalently attached to the surface of the support or incorporated into the body of the support. Linking to the surface may be accomplished as discussed above. The cleavage-inducing moiety may be incorporated into the body of the support either during or after the preparation of the support. In general, the cleavage-inducing moiety is associated with the support in an amount necessary to achieve the necessary amount of active species. Generally, the amount of cleavage-inducing moiety is determined empirically.

Photosensitizers as Cleavage-Inducing Moieties

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a class-specific reagent. Guidance for constructiing of such compositions, particularly for antibodies as binding agents, available in the literature, e.g. in the fields of photodynamic therapy, immunodiagnostics, and the like. The following are exemplary references: Ullman, et al., Proc. Natl. Acad. Sci. USA 91, 5426-5430 (1994); Strong et al, Ann. New York Acad. Sci., 745: 297-320 (1994); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251, 581; McCapra, U.S. Pat. No. 5,516,636; and the like.

Likewise, there is guidance in the literature regarding the properties and selection of photosensitizers suitable for use in the present invention. The following are exemplary references: Wasserman and R. W. Murray. Singlet Oxygen. (Academic Press, New York, 1979); Baumstark, Singlet Oxygen, Vol. 2 (CRC Press Inc., Boca Raton, Fla. 1983); and Turro, Modem Molecular Photochemistry (University Science Books, 1991).

The photosensitizers are sensitizers for generation of singlet oxygen by excitation with light. The photosensitizers include dyes and aromatic compounds, and are usually compounds comprised of covalently bonded atoms, usually with multiple conjugated double or triple bonds. The compounds typically absorb light in the wavelength range of about 200 to about 1,100 nm, usually, about 300 to about 1,000 nm, preferably, about 450 to about 950 nm, with an extinction coefficient at its absorbance maximum greater than about 500 $M^{-1}$ $cm^{-1}$, preferably, about 5,000 $M^{-1}$ $cm^{-1}$, more preferably, about 50,000 $M^{-1}$ $cm^{-1}$, at the excitation wavelength. The lifetime of an excited state produced following absorption of light in the absence of oxygen will usually be at least about 100 nanoseconds, preferably, at least about 1 millisecond. In general, the lifetime must be sufficiently long to permit cleavage of a linkage in a reagent in accordance with the present invention. Such a reagent is normally present at concentrations as discussed below. The photosensitizer excited state usually has a different spin quantum number (S) than its ground state and is usually a triplet (S=1) when the ground state, as is usually the case, is a singlet (S=0). Preferably, the photosensitizer has a high intersystem crossing yield. That is, photoexcitation of a photosensitizer usually produces a triplet state with an efficiency of at least about 10%, desirably at least about 40%, preferably greater than about 80%.

Photosensitizers chosen are relatively photostable and, preferably, do not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures.

A large variety of light sources are available to photoactivate photosensitizers to generate singlet oxygen. Both polychromatic and monchromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like. By way of example, a photoactivation device disclosed in Bjornson et al, International patent publication WO 03/051669 is employed. Briefly, the photoactivation device is an array of light emitting diodes (LEDs) mounted in housing that permits the simultaneous illumination of all the wells in a 96-well plate. A suitable LED for use in the present invention is a high power GaAIAs IR emitter, such as model OD-880W manufactured by OPTO DIODE CORP. (Newbury Park, Calif.).

Examples of photosensitizers that may be utilized in the present invention are those that have the above properties and are enumerated in the following references: Singh and Ullman, U.S. Pat. No. 5,536,834; Li et al, U.S. Pat. No. 5,763,602; Martin et al, Methods Enzymol., 186: 635-645 (1990); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; Thetford, European patent publ. 0484027; Sessler et al, SPIE, 1426: 318-329 (1991); Magda et al, U.S. Pat. No. 5,565,552; Roelant, U.S. Pat. No. 6,001,673; and the like.

As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically.

Figure 2C:
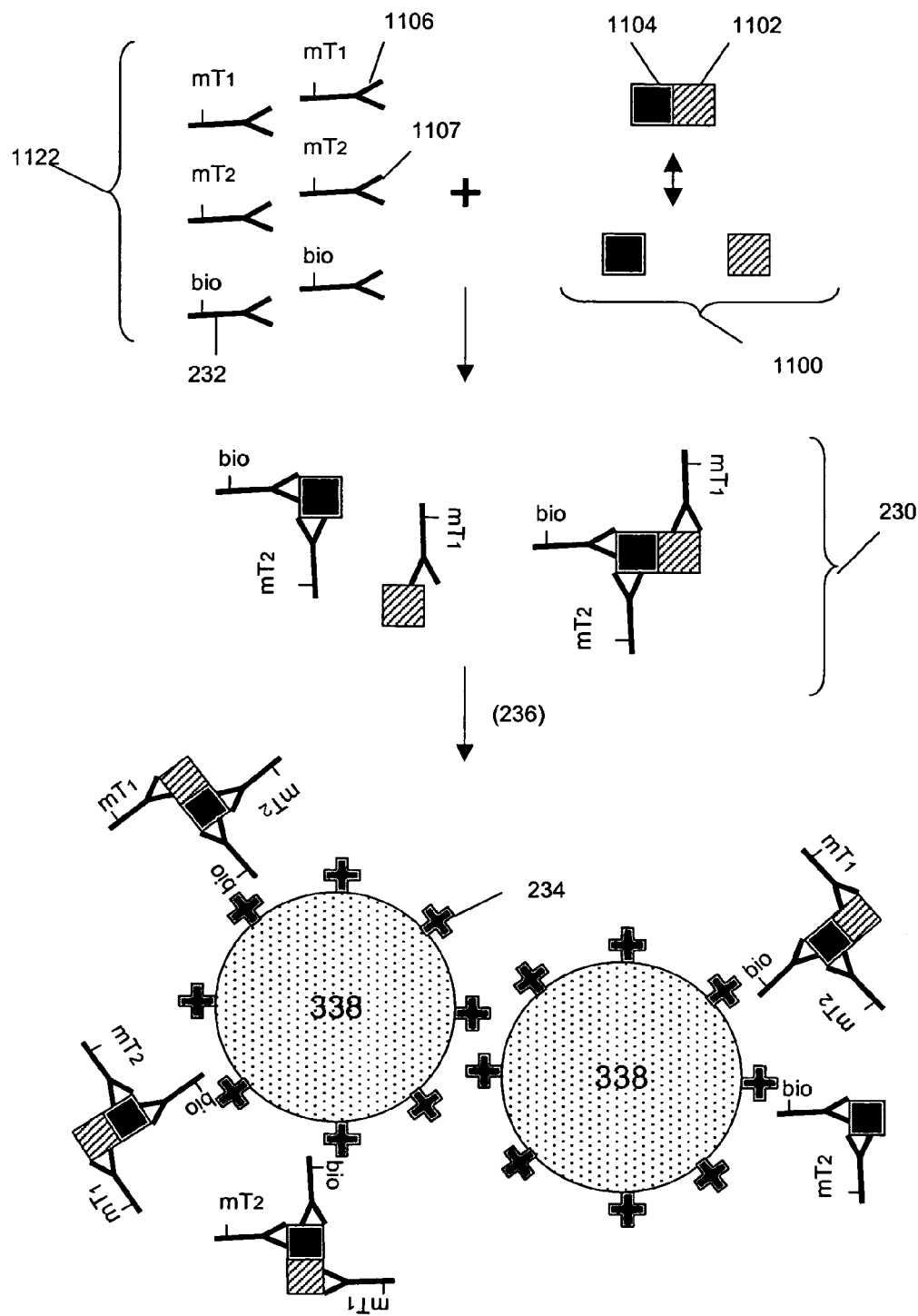
Figure 2D:
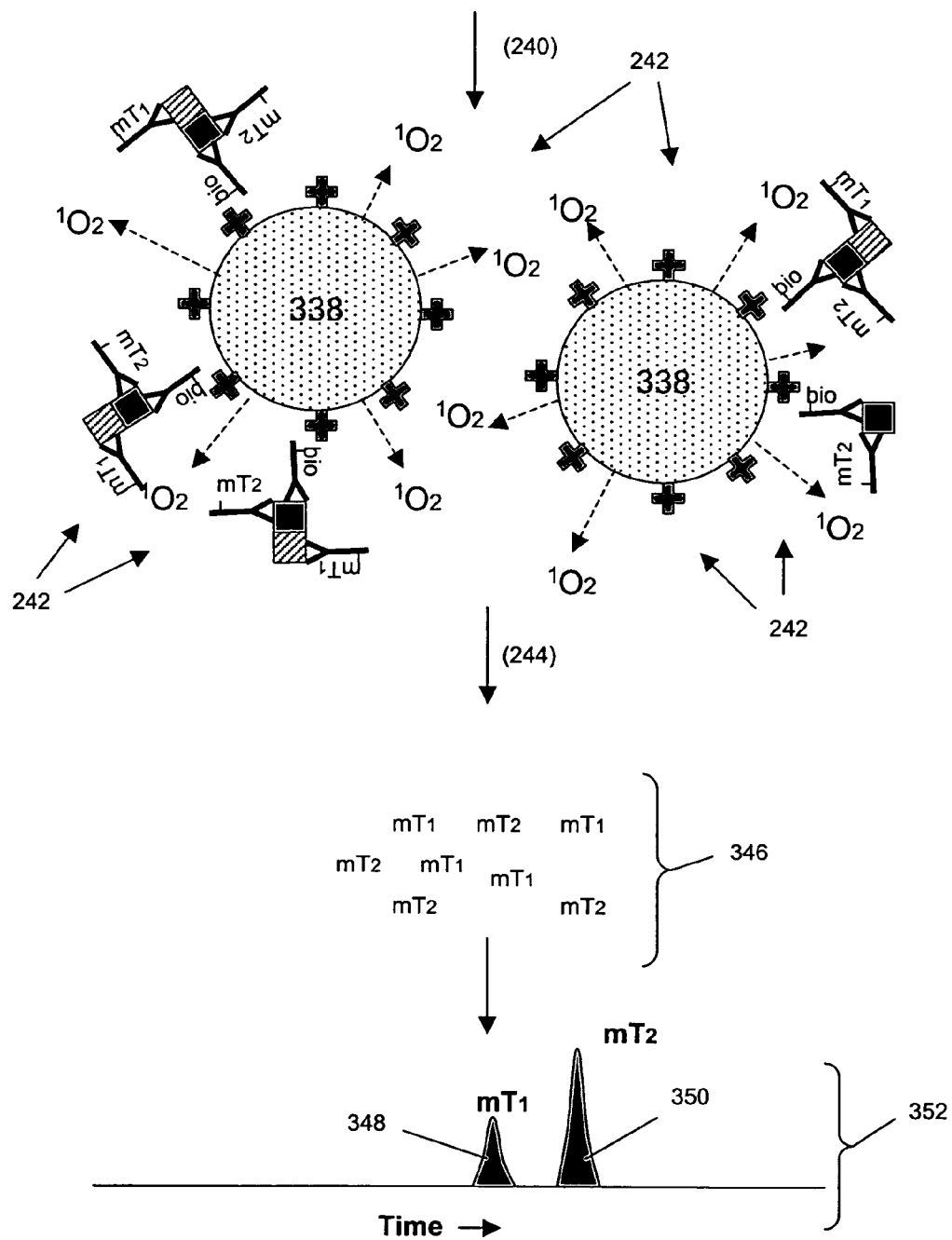

In one embodiment, a photosensitizer is incorporated into a latex particle to form photosensitizer beads, e.g. as disclosed by Pease et al., U.S. Pat. No. 5,709,994; Pollner, U.S. Pat. No. 6,346,384; and Pease et al, PCT publication WO 01/84157. Alternatively, photosensitizer beads may be prepared by covalently attaching a photosensitizer, such as rose bengal, to 0.5 micron latex beads by means of chloromethyl groups on the latex to provide an ester linking group, as described in J. Amer. Chem. Soc., 97: 3741 (1975). Use of such photosensitizer beads is illustrated in FIG. 2C. Complexes (230) are formed after combining reagents (1122) with a sample. This reaction may be carried out, for example, in a conventional 96-well or 384-well microtiter plate, or the like, having a filter membrane that forms one wall, e.g. the bottom, of the wells that allows reagents to be removed by the application of a vacuum. This allows the convenient exchange of buffers, if the buffer required for specific binding of binding compounds is different that the buffer required for either singlet oxygen generation or separation. For example, in the case of antibody-based binding compounds, a high salt buffer is required. If electrophoretic separation of the released tags is employed, then better performance is achieved by exchanging the buffer for one that has a lower salt concentration suitable for electrophoresis. In this embodiment, instead of attaching a photosensitizer directly to a binding compound, such as an antibody, a cleaving probe comprises two components: antibody (232) derivatized with a capture moiety, such as biotin (indicated in FIG. 2C as "bio") and photosensitizer bead (338) whose surface is derivatized with an agent (234) that specifically binds with the capture moiety, such as avidin or streptavidin. Complexes (230) are then captured (236) by photosensitizer beads by way of the capture moiety, such as biotin. Conveniently, if the pore diameter of the filter membrane is selected so that photosensitizer beads (338) cannot pass, then a buffer exchange also serves to remove unbound binding compounds, which leads to an improved signal. After an appropriate buffer for separation has been added, if necessary, photosensitizer beads (338) are illuminated (240) so that singlet oxygen is generated (242) and molecular tags are released (244). Such released molecular tags (346) are then separated to form separation profile (352) and dimers are quantified ratiometrically from peaks (348) and (350). Photosensitizer beads may be used in either homogeneous or heterogeneous assay formats.

Preferably, when analytes, such as cell surface receptors, are being detected or antigen in a fixed sample, a cleaving probe may comprise a primary haptenated antibody and a secondary anti-hapten binding protein derivatized with multiple photosensitizer molecules. A preferred primary haptenated antibody is a biotinylated antibody, and preferred secondary anti-hapten binding proteins may be either an anti-biotin antibody or streptavidin. Other combinations of such primary and secondary reagents are well known in the art, e.g.

Figure 2E:
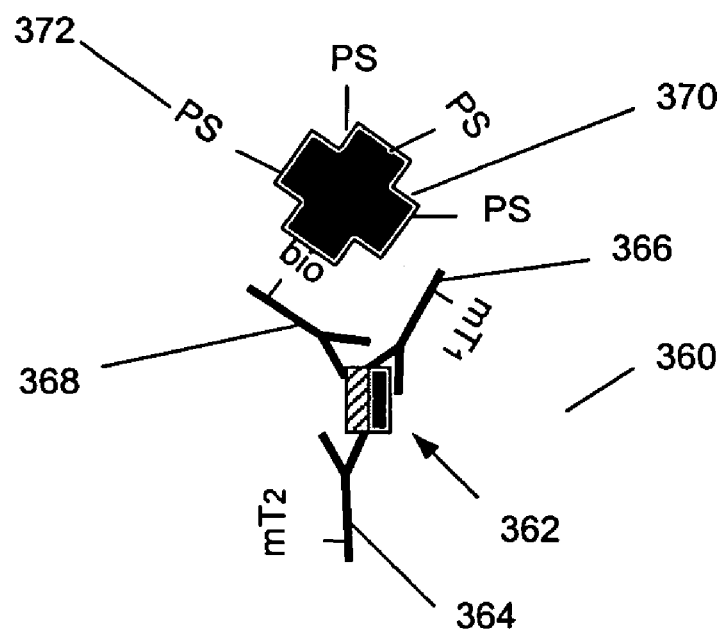

Haugland, Handbook of Fluorescent Probes and Research Reagents, Ninth Edition (Molecular Probes, Eugene, Oreg., 2002). An exemplary combination of such reagents is illustrated in FIG. 2E. There binding compounds (366 and 368) having releasable tags ("mT$_1$" and "mT$_2$" in the FIG), and primary antibody (368) derivatized with biotin (369) are specifically bound to different epitopes of receptor dimer (362) in membrane (360). Biotin-specific binding protein (370), e.g. streptavidin, is attached to biotin (369) bringing multiple photosensitizers (372) into effective proximity of binding compounds (366 and 368). Biotin-specific binding protein (370) may also be an anti-biotin antibody, and photosensitizers may be attached via free amine group on the protein by conventional coupling chemistries, e.g. Hermanson (cited above). An exemplary photosensitizer for such use is an NHS ester of methylene blue prepared as disclosed in Shimadzu et al, European patent publication 0510688.

Exemplary Proteins Forming Detectable Complexes

Assays of the invention may be used to detect or measure concentrations or amounts of virtually any molecular complexes that permit specific binding of binding compounds. Of particular interest are protein complexes related to mammalian signal transduction, including cell surface receptors and intracellular signaling proteins. Such proteins include, but are not limited to, the proteins of the following Table I. Preferably, the human forms of the following proteins and protein families are intended.

TABLE I

Exemplary Target Proteins

| Abbreviation | Name | Reference |
|---|---|---|
| 14-3-3 protein | | Aitken et al, Biochem. Soc. Trans., 30: 351-360 (2002) |
| Akt/PKB | Serine/threonine protein kinase | Summers et al, Ann. N.Y. Acad. Sci., 892: 169-186 (1999) |
| Bad | Member of Bcl-2 protein family | Schurmann et al, Mol. Cell. Biol. 20: 453-461 (2000) |
| Bax | Member of Bcl-2 family | Gross et al, Mol. Cell. Biol. 20: 3125-3136 (2000) |
| Bcl-2 | | Srivastava et al, Proc. Natl. Acad. Sci., 96: 3775-3780 (1999) |
| EGF receptors | Also known as Her family of receptors: Her1, Her2, Her3, and Her4 | Yarden and Sliwkowski, Nature Reviews Molecular Cell Biology, 2: 127-137 (2001) |
| Erk | Extracellular signal-regulated protein, including Erk1, Erk2, Erk3, Erk4, and Erk5. | Burack et al, Biochemistry, 36: 5929-5933 (1997) |
| Grb2 | Growth factor receptor binding protein-2 | El-Shemerly et al, J. Biol. Chem., 272: 30500-30602 (1997) |
| IGF-1 receptor | Insulin-like growth factor receptor | Butler et al, Comp. Biochem. Physiol. B. Biochem. Mol. Biol. 121: 19-26 (1998) |
| Insulin receptor | | |
| Integrin receptor | Including alpha, beta, alpha2, alpha6, beta1, beta3 isoforms | |
| IRS-1 | Insulin receptor substrate | DeFea et al, Biochemistry, 36: 12939-12947 (1997) |
| JNK1 (SAPKγ) | c-Jun amino-terminal kinase | Coso et al, Cell, 81: 1137-1146 (1995) |
| MEK | Mitogen-activated Erk-activating kinase | Alessandrini et al, J. Biol. Chem. 271: 31612-31618 (1996) |
| MEKK1 | | Siow et al, J. Biol. Chem. 272: 7586-7594 (1997) |
| p38 (Erk6) | MAPK family member | Weinbrenner et al, J. Mol. Cell. Cardiol., 29: 2383-2391 (1997) |
| PDGF receptor | Platelet derived growth factor receptor | |
| PI3K | Phosphatidyl inositol-3 kinase | von Willebrand et al, Cell Signal., 10: 407-413 (1998) |
| PTEN | | |
| Raf | Cytoplasmic serine/threonine protein kinase activated by Ras-GTP | Diaz et al, Mol. Cell. Biol. 17: 4509-4516 (1997) |
| B-Raf | | |
| Ras | GDP/GTP binding protein that activates the Raf-MEK-MAPK pathway | Porfiri and McCormick, J. Biol Chem. 271: 5871-5877 (1996) |
| Shc | Early signaling intermediates between receptor tyrosine kinases and other components of Ras pathway | Walk et al, Eur. J. Immunol., 28: 2265-2275 (1998). |
| Src | | |
| SOS | Son of sevenless | Corbalan-Garcia et al, Mol. Cell. Biol., 16: 5674-5682 (1996) |
| TNF-R1 | Tumor necrosis factor receptor-1 | |
| TRADD | TNF-receptor associated death domain protein | Yu et al, Curr. Biol., 9: 539-542 (1999) |

Assay Conditions

The following general discussion of methods and specific conditions and materials are by way of illustration and not limitation. One of ordinary skill in the art will understand how the methods described herein can be adapted to other applications, particularly with using different samples, cell types and target complexes.

In conducting the methods of the invention, a combination of the assay components is made, including the sample being tested, the binding compounds, and optionally the cleaving probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages, and may require incubations before the complete mixture has been assembled, or before the cleaving reaction is initiated.

The amounts of each reagent are usually determined empirically. The amount of sample used in an assay will be determined by the predicted number of target complexes present and the means of separation and detection used to monitor the signal of the assay. In general, the amounts of the binding compounds and the cleaving probe are provided in molar excess relative to the expected amount of the target molecules in the sample, generally at a molar excess of at least 1.5, more desirably about 10-fold excess, or more. In specific applications, the concentration used may be higher or lower, depending on the affinity of the binding agents and the expected number of target molecules present on a single cell. Where one is determining the effect of a chemical compound on formation of oligomeric cell surface complexes, the compound may be added to the cells prior to, simultaneously with, or after addition of the probes, depending on the effect being monitored.

The assay mixture is combined and incubated under conditions that provide for binding of the probes to the cell surface molecules, usually in an aqueous medium, generally at a physiological pH (comparable to the pH at which the cells are cultures), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually 25° to 37°.

After assembly of the assay mixture and incubation to allow the probes to bind to cell surface molecules, the mixture is treated to activate the cleaving agent to cleave the tags from the binding compounds that are within the effective proximity of the cleaving agent, releasing the corresponding tag from the cell surface into solution. The nature of this treatment will depend on the mechanism of action of the cleaving agent. For example, where a photosensitizer is employed as the cleaving agent, activation of cleavage will comprise irradiation of the mixture at the wavelength of light appropriate to the particular sensitizer used.

Following cleavage, the sample is then analyzed to determine the identity of tags that have been released. Where an assay employing a plurality of binding compounds is employed, separation of the released tags will generally precede their detection. The methods for both separation and detection are determined in the process of designing the tags for the assay. A preferred mode of separation employs electrophoresis, in which the various tags are separated based on known differences in their electrophoretic mobilities.

As mentioned above, in some embodiments, if the assay reaction conditions may interfere with the separation technique employed, it may be necessary to remove, or exchange, the assay reaction buffer prior to cleavage and separation of the molecular tags. For example, assay conditions may include salt concentrations (e.g. required for specific binding) that degrade separation performance when molecular tags are separated on the basis of electrophoretic mobility. Thus, such high salt buffers may be removed, e.g. prior to cleavage of molecular tags, and replaced with another buffer suitable for electrophoretic separation through filtration, aspiration, dilution, or other means.

Separation of Released Molecular Tags

As mentioned above, molecular tags are designed for separation by a separation technique that can distinguish molecular tags based on one or more physical, chemical, and/or optical characteristics (referred to herein as "separation characteristics"). As also mentioned above, separation techniques that may be used with the various embodiments of the invention include normal phase or reverse phase HPLC, ion exchange HPLC, capillary electrochromatography, mass spectroscopy, gas phase chromatography, and the like. Preferably, the separation technique selected is capable of providing quantitative information as well as qualitative information about the presence or absence of molecular tags (and therefore, corresponding analytes). In one aspect, a liquid phase separation technique is employed so that a solution, e.g. buffer solution, reaction solvent, or the like, containing a mixture of molecular tags is processed to bring about separation of individual kinds of molecular tags. Usually, such separation is accompanied by the differential movement of molecular tags from such a starting mixture along a path until discernable peaks or bands form that correspond to regions of increased concentration of the respective molecular tags. Such a path may be defined by a fluid flow, electric field, magnetic field, or the like. The selection of a particular separation technique depends on several factors including the expense and convenience of using the technique, the resolving power of the technique given the chemical nature of the molecular tags, the number of molecular tags to be separated, the type of detection mode employed, and the like. Preferably, molecular tags are electrophoretically separated to form an electropherogram in which the separated molecular tags are represented by distinct peaks.

A. Electrophoretic Separation

Methods for electrophoresis of are well known and there is abundant guidance for one of ordinary skill in the art to make design choices for forming and separating particular pluralities of molecular tags. The following are exemplary references on electrophoresis: Krylov et al, Anal. Chem., 72: 111R-128R (2000); P. D. Grossman and J. C. Colburn, Capillary Electrophoresis: Theory and Practice, Academic Press, Inc., NY (1992); U.S. Pat. Nos. 5,374,527; 5,624,800; 5,552,028; ABI PRISM 377 DNA Sequencer User's Manual, Rev. A, January 1995, Chapter 2 (Applied Biosystems, Foster City, Calif.); and the like. In one aspect, molecular tags are separated by capillary electrophoresis. Design choices within the purview of those of ordinary skill include but are not limited to selection of instrumentation from several commercially available models, selection of operating conditions including separation media type and concentration, pH, desired separation time, temperature, voltage, capillary type and dimensions, detection mode, the number of molecular tags to be separated, and the like.

In one aspect of the invention, during or after electrophoretic separation, the molecular tags are detected or identified by recording fluorescence signals and migration times (or migration distances) of the separated compounds, or by constructing a chart of relative fluorescent and order of migration of the molecular tags (e.g., as an electropherogram). To perform such detection, the molecular tags can be illuminated by standard means, e.g. a high intensity mercury vapor lamp, a laser, or the like. Typically, the molecular tags are illuminated by laser light generated by a He—Ne gas laser or a solid-state diode laser. The fluorescence signals can then be detected by a light-sensitive detector, e.g., a photomultiplier tube, a charged-coupled device, or the like. Exemplary electrophoresis detection systems are described elsewhere, e.g., U.S. Pat. Nos. 5,543,026; 5,274,240; 4,879,012; 5,091,652; 6,142,162; or the like. In another aspect, molecular tags may be detected electrochemically detected, e.g. as described in U.S. Pat. No. 6,045,676.

Electrophoretic separation involves the migration and separation of molecules in an electric field based on differences in mobility. Various forms of electrophoretic separation include, by way of example and not limitation, free zone electrophoresis, gel electrophoresis, isoelectric focusing, isotachophoresis, capillary electrochromatography, and micellar electrokinetic chromatography. Capillary electrophoresis involves electroseparation, preferably by electrokinetic flow, including electrophoretic, dielectrophoretic and/or electroosmotic flow, conducted in a tube or channel of from about 1 to about 200 micrometers, usually, from about 10 to about 100 micrometers cross-sectional dimensions. The capillary may be a long independent capillary tube or a channel in a wafer or film comprised of silicon, quartz, glass or plastic.

In capillary electroseparation, an aliquot of the reaction mixture containing the molecular tags is subjected to electroseparation by introducing the aliquot into an electroseparation channel that may be part of, or linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan. Detection may be by any of the known methods associated with the analysis of capillary electrophoresis columns including the methods shown in U.S. Pat. No. 5,560,811 (column 11, lines 19-30), U.S. Pat. Nos. 4,675,300, 4,274,240 and 5,324,401, the relevant disclosures of which are incorporated herein by reference. Those skilled in the electrophoresis arts will recognize a wide range of electric potentials or field strengths may be used, for example, fields of 10 to 1000 V/cm are used with about 200 to about 600 V/cm being more typical. The upper voltage limit for commercial systems is about 30 kV, with a capillary length of about 40 to about 60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from about 180 to about 1500 nm, usually about 220 to about 800 nm, more usually about 450 to about 700 nm, to have low transmission losses. Suitable materials include fused silica, plastics, quartz, glass, and so forth.

Figure 6A:
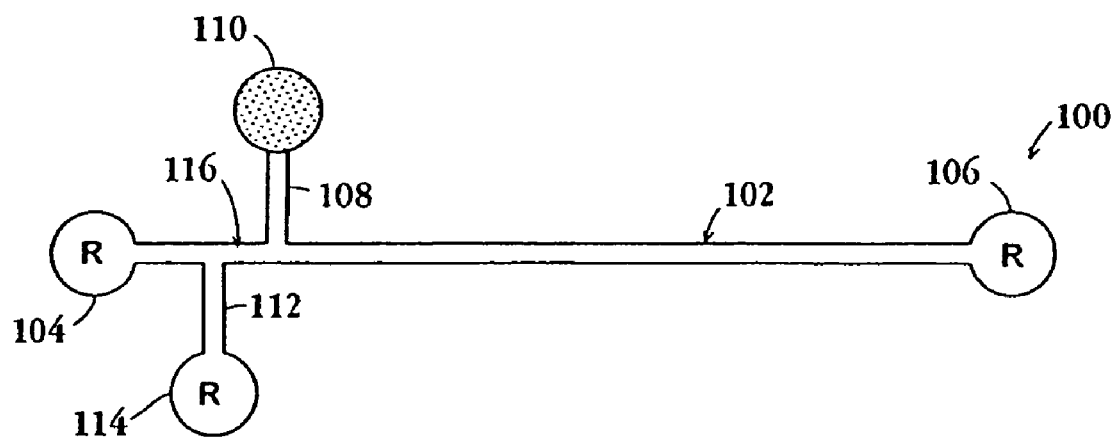
FIGS. 6A-6C diagrammatically illustrate a microfluidics device for implementing a step of electrophoretically separating molecular tags.
Figure 6B:
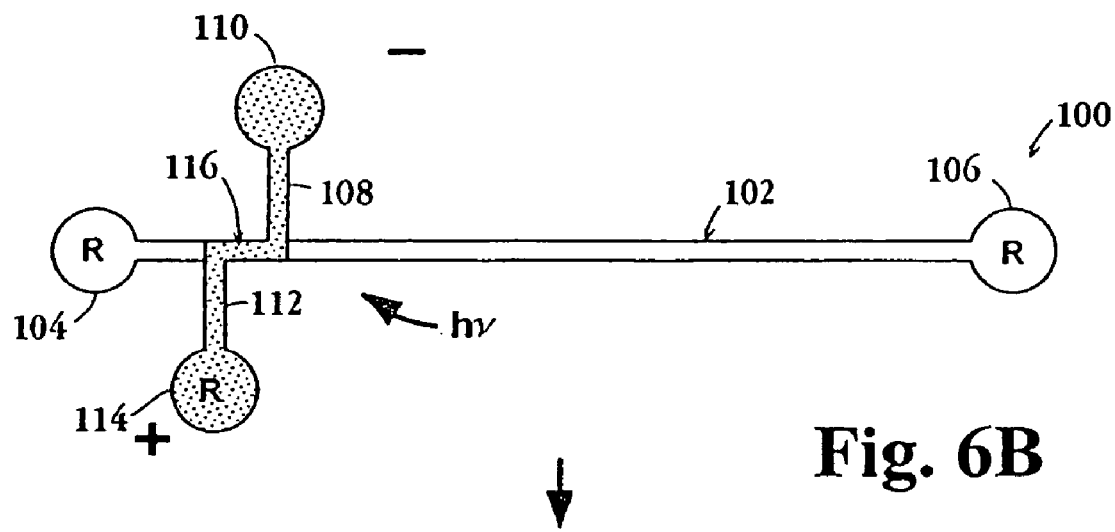
Figure 6C:
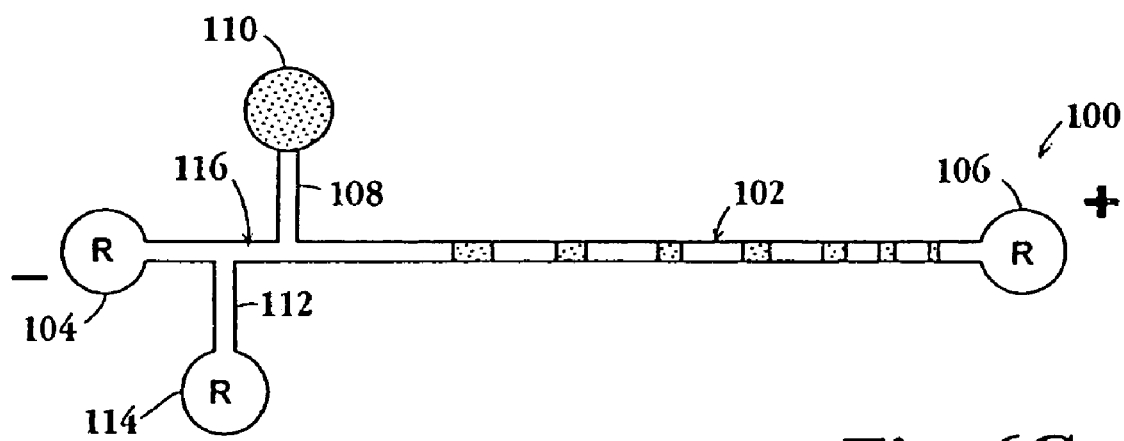

In one aspect of the invention, molecular tags are separated by electrophoresis in a microfluidics device, as illustrated diagrammatically in FIGS. 6A-6C. Microfluidics devices are described in a number of domestic and foreign Letters Patent and published patent applications. See, for example, U.S. Pat. Nos. 5,750,015; 5,900,130; 6,007,690; and WO 98/45693; WO 99/19717 and WO 99/15876. Conveniently, an aliquot, generally not more than about 5 µl, is transferred to the sample reservoir of a microfluidics device, either directly through electrophoretic or pneumatic injection into an integrated system or by syringe, capillary or the like. The conditions under which the separation is performed are conventional and will vary with the nature of the products.

By way of illustration, FIGS. 6A-6C show a microchannel network 100 in a microfluidics device of the type detailed in the application noted above, for sample loading and electrophoretic separation of a sample of probes and tags produced in the assay above. Briefly, the network includes a main separation channel 102 terminating at upstream and downstream reservoirs 104, 106, respectively. The main channel is intersected at offset axial positions by a side channel 108 that terminates at a reservoir 110, and a side channel 112 that terminates at a reservoir 114. The offset between the two-side channels forms a sample loading zone 116 within the main channel.

In operation, an assay mixture is placed in sample reservoir 110, illustrated in FIG. 6A. As noted, the assay mixture contains one or more target cells with surface-bound cleaving agent, one or more protein probes, and optionally, molecular tag standard. The assay reaction, involving initial probe binding to target cell(s), followed by cleavage of probe linkers in probe-bound cells, may be carried out in sample reservoir 110, or alternatively, the assay reactions can be carried out in another reaction vessel, with-the reacted sample components the added to the sample reservoir.

To load released molecular tags into the sample-loading zone, an electric field is applied across reservoirs 110, 114, in the direction indicated in FIG. 6B, wherein negatively charged released molecular tags are drawn from reservoir 110 into loading zone 116, while uncharged or positively charged sample components remain in the sample reservoir. The released tags in the loading zone can now be separated by conventional capillary electrophoresis, by applying an electric filed across reservoirs 104, 106, in the direction indicated in FIG. 6C.

From the resulting electrophoretic pattern, the molecular tags, and corresponding analytes, can be identified. This is typically done by placing a fluorescence detector near the downstream end of the separation channel, and constructing a electropherogram of the separated molecular tags, first to determine the separation characteristic (in this case, electrophoretic mobility) as above, and secondly, to measure signal intensity, e.g., peak height or peak area, as a measure of the relative amount of tag associated with each probe. Methods for detecting and quantifying levels of a detectable probe are well known. In one preferred method, the molecular tags are fluorescent labeled. A standard fluorescence-emission source is directed against a detection zone in a downstream portion of the separation medium, and fluorescence emission of the zone is measured by a standard light detector. The signal height or area recorded provides a measure of product and substrate concentration in the sample. With the above detection information, it is now possible to assign each detected molecular tag to a particular probe in the probe set, and to compare the relative levels of each detectable probe, as a measure of its relatively substrate conversion or ligand binding.

B. Chromatographic Separation

In one aspect of the invention, pluralities of molecular tags are designed for separation by chromatography based on one or more physical characteristics that include but are not limited to molecular weight, shape, solubility, pKa, hydrophobicity, charge, polarity, or the like. A chromatographic separation technique is selected based on parameters such as column type, solid phase, mobile phase, and the like, followed by selection of a plurality of molecular tags that may be separated to form distinct peaks or bands in a single operation. Several factors determine which HPLC technique is selected for use in the invention, including the number of molecular tags to be detected (i.e. the size of the plurality), the estimated quantities of each molecular tag that will be generated in the assays, the availability and ease of synthesizing molecular tags that are candidates for a set to be used in multiplexed assays, the detection modality employed, and the availability, robustness, cost, and ease of operation of HPLC instrumentation, columns, and solvents. Generally, columns and techniques are favored that are suitable for analyzing limited amounts of sample and that provide the highest resolution separations. Guidance for making such selections can be found in the literature, e.g. Snyder et al, Practical HPLC Method Development, (John Wiley & Sons, New York, 1988); Millner, "High Resolution Chromatography: A Practical Approach", Oxford University Press, New York (1999), Chi-San Wu, "Column Handbook for Size Exclusion Chromatography", Academic Press, San Diego (1999), and Oliver, "HPLC of Macromolecules: A Practical Approach, Oxford University Press", Oxford, England (1989). In particular, procedures are available for systematic development and optimization of chromatographic separations given conditions, such as column type, solid phase, and the like, e.g. Haber et al, J. Chromatogr. Sci., 38: 386-392 (2000); Outinen et al, Eur. J. Pharm. Sci., 6: 197-205 (1998); Lewis et al, J. Chromatogr., 592: 183-195 and 197-208 (1992); and the like.

In one aspect, initial selections of molecular tag candidates are governed by the physiochemical properties of molecules typically separated by the selected column and stationary phase. The initial selections are then improved empirically by following conventional optimization procedure, as described in the above reference, and by substituting more suitable candidate molecular tags for the separation objectives of a particular embodiment. In one aspect, separation objectives of the invention include (i) separation of the molecular tags of a plurality into distinguishable peaks or bands in a separation time of less than 60 minutes, and more preferably in less than 40 minutes, and still more preferably in a range of between 10 to 40 minutes, (ii) the formation of peaks or bands such that any pair has a resolution of at least 1.0, more preferably at least 1.25, and still more preferably, at least 1.50, (iii) column pressure during separation of less than 150 bar, (iv) separation temperature in the range of from 25° C. to 90° C., preferably in the range of from 35° C. to 80° C., and (v) the plurality of distinguishable peaks is in the range of from 5 to 30 and all of the peaks in the same chromatogram. As used herein, "resolution" in reference to two peaks or bands is the distance between the two peak or band centers divided by the average base width of the peaks, e.g. Snyder et al (cited above). A chromatographic method is used to separate molecular tags based on their chromatographic properties. A chromatographic property can be, for example, a retention time of a molecular tag on a specific chromatographic medium under defined conditions, or a specific condition under which a molecular tag is eluted from a specific chromatographic medium. A chromatographic property of a molecular tag can also be an order of elution, or pattern of elution, of a molecular tag contained in a group or set of molecular tags being chromatographically separated using a specific chromatographic medium under defined conditions. A chromatographic property of a molecular tag is determined by the physical properties of the molecular tag and its interactions with a chromatographic medium and mobile phase. Defined conditions for chromatography include particular mobile phase solutions, column geometry, including column diameter and length, pH, flow rate, pressure and temperature of column operation, and other parameters that can be varied to obtain the desired separation of molecular tags. A molecular tag, or chromatographic property of a molecular tag, can be detected using a variety of chromatography methods.

Sets of molecular tags detected in a single experiment generally are a group of chemically related molecules that differ by mass, charge, mass-charge ratio, detectable tag, such as differing fluorophores or isotopic labels, or other unique characteristic. Therefore, both the chemical nature of the molecular tag and the particular differences among molecular tags in a group of molecular tags can be considered when selecting a suitable chromatographic medium for separating molecular tags in a sample.

Separation of molecular tags by liquid chromatography can be based on physical characteristics of molecular tags such as charge, size and hydrophobicity of molecular tags, or functional characteristics such as the ability of molecular tags to bind to molecules such as dyes, lectins, drugs, peptides and other ligands on an affinity matrix. A wide variety of chromatographic media are suitable for separation of molecular tag based on charge, size, hydrophobicity and other chromatographic properties of molecular tags. Selection of a particular chromatographic medium will depend upon the properties of molecular tags employed.

Separated molecular tags can be detected using a variety of analytical methods, including detection of intrinsic properties of molecular tags, such as absorbance, fluorescence or electrochemical properties, as well as detection of a detection group or moiety attached to a molecular tag. Although not required, a variety of detection groups or moieties can be attached to molecular tags to facilitate detection after chromatographic separation.

Detection methods for use with liquid chromatography are well known, commercially available, and adaptable to automated and high-throughput sampling. The detection method selected for analysis of molecular tags will depend upon whether the molecular tags contain a detectable group or moiety, the type of detectable group used, and the physicochemical properties of the molecular tag and detectable group, if used. Detection methods based on fluorescence, electrolytic conductivity, refractive index, and evaporative light scattering can be used to detect various types of molecular tags.

A variety of optical detectors can be used to detect a molecular tag separated by liquid chromatography. Methods for detecting nucleic acids, polypeptides, peptides, and other macromolecules and small molecules using ultraviolet (UV)/visible spectroscopic detectors are well known, making UV/visible detection the most widely used detection method for HPLC analysis. Infrared spectrophotometers also can be used to detect macromolecules and small molecules when used with a mobile phase that is a transparent polar liquid.

Variable wavelength and diode-array detectors represent two commercially available types of UV/visible spectrophotometers. A useful feature of some variable wavelength UV detectors is the ability to perform spectroscopic scanning and precise absorbance readings at a variety of wavelengths while the peak is passing through the flowcell. Diode array technology provides the additional advantage of allowing absorbance measurements at two or more wavelengths, which permits the calculation of ratios of such absorbance measurements. Such absorbance rationing at multiple wavelengths is particularly helpful in determining whether a peak represents one or more than one molecular tag.

Fluorescence detectors can also be used to detect fluorescent molecular tags, such as those containing a fluorescent detection group and those that are intrinsically fluorescent. Typically, fluorescence sensitivity is relatively high, providing an advantage over other spectroscopic detection methods when molecular tags contain a fluorophore. Although molecular tags can have detectable intrinsic fluorescence, when a molecular tag contains a suitable fluorescent detection group, it can be possible to detect a single molecular tag in a sample.

Electrochemical detection methods are also useful for detecting molecular tags separated by HPLC. Electrochemical detection is based on the measurement of current resulting from oxidation or reduction reaction of the molecular tags at a suitable electrode. Since the level of current is directly proportional to molecular tag concentration, electrochemical detection can be used quantitatively, if desired.

Evaporative light scattering detection is based on the ability of particles to cause photon scattering when they traverse the path of a polychromatic beam of light. The liquid effluent from an HPLC is first nebulized and the resultant aerosol mist, containing the molecular tags, is directed through a light beam. A signal is generated that is proportional to the amount of the molecular tag present in a sample, and is independent of the presence or absence of detectable groups such as chromophores, fluorophores or electroactive groups. Therefore, the presence of a detection group or moiety on a molecular tag is not required for evaporative light scattering detection.

Mass spectrometry methods also can be used to detect molecular tags separated by HPLC. Mass spectrometers can resolve ions with small mass differences and measure the mass of ions with a high degree of accuracy and sensitivity. Mass spectrometry methods are well known in the art (see Burlingame et al. *Anal. Chem.* 70:647R-716R (1998); Kinter and Sherman, Protein Sequencing and Identification Using Tandem Mass Spectrometry Wiley-Interscience, New York (2000)).

Analysis of data obtained using any detection method, such as spectral deconvolution and quantitative analysis can be manual or computer-assisted, and can be performed using automated methods. A variety of computer programs can be used to determine peak integration, peak area, height and retention time. Such computer programs can be used for convenience to determine the presence of a molecular tag qualitatively or quantitatively. Computer programs for use with HPLC and corresponding detectors are well known to those skilled in the art and generally are provided with commercially available HPLC and detector systems.

A variety of commercially available systems are well-suited for high throughput analysis of molecular tags. Those skilled in the art can determine appropriate equipment, such as automated sample preparation systems and autoinjection systems, useful for automating HPLC analysis of molecular tags. Automated methods can be used for high-throughput analysis of molecular tags, for example, when a large number of samples are being processes or for multiplexed application of the methods of the invention for detecting target analytes. An exemplary HPLC instrumentation system suitable for use with the present invention is the Agilent 1100 Series HPLC system (Agilent Technologies, Palo Alto, Calif.).

Those skilled in the art will be aware of quality control measures useful for obtaining reliable analysis of molecular tags, particular when analysis is performed in a high-throughput format. Such quality control measures include the use of external and internal reference standards, analysis of chromatograph peak shape, assessment of instrument performance, validation of the experimental method, for example, by determining a range of linearity, recovery of sample, solution stability of sample, and accuracy of measurement.

C. Separation by Mass Spectrometry

Mass spectrometry methods are well known in the art (see Burlingame et al. Anal. Chem. 70:647R-716R (1998); Kinter and Sherman, Protein Sequencing and Identification Using Tandem Mass Spectrometry Wiley-Interscience, New York (2000)). The basic processes associated with a mass spectrometry method are the generation of gas-phase ions derived from the sample, and the measurement of their mass.

The movement of gas-phase ions can be precisely controlled using electromagnetic fields generated in the mass spectrometer. The movement of ions in these electromagnetic fields is proportional to the m/z of the ion and this forms the basis of measuring the m/z and therefore the mass of a sample. The movement of ions in these electromagnetic fields allows the ions to be contained and focused which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Exemplary mass analyzers include a quadrupole mass filter, ion trap mass analyzer and time-of-flight mass analyzer.

The ion formation process is a starting point for mass spectrum analysis. Several ionization methods are available and the choice of ionization method depends on the sample to be analyzed. For example, for the analysis of polypeptides a relatively gentle ionization procedure such as electrospray ionization (ESI) can be desirable. For ESI, a solution containing the sample is passed through a fine needle at high potential, which creates a strong electrical field resulting in a fine spray of highly charged droplets that is directed into the mass spectrometer. Other ionization procedures include, for example, fast-atom bombardment (FAB), which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix. Other ionization procedures known in the art include, for example, plasma and glow discharge, plasma desorption ionization, resonance ionization, and secondary ionization. A tag reporter can become ionized prior to, during, or after cleavage from the binding compound.

Electrospray ionization (ESI) has several properties that are useful for the invention described herein. For example, ESI can be used for biological molecules such as polypeptides that are difficult to ionize or vaporize. In addition, the efficiency of ESI can be very high which provides the basis for highly sensitive measurements. Furthermore, ESI produces charged molecules from solution, which is convenient for analyzing tag reporters that are in solution. In contrast, ionization procedures such as MALDI require crystallization of the sample prior to ionization.

Since ESI can produce charged molecules directly from solution, it is compatible with samples from liquid chromatography systems. For example, a mass spectrometer can have an inlet for a liquid chromatography system, such as an HPLC, so that fractions flow from the chromatography column into the mass spectrometer. This in-line arrangement of a liquid chromatography system and mass spectrometer is sometimes referred to as LC-MS. A LC-MS system can be used, for example, to separate un-cleaved or partially cleaved tag reporters from cleaved tag reporters before mass spectrometry analysis. In addition, chromatography can be used to remove salts or other buffer components from the tag reporter sample before mass spectrometry analysis. For example, desalting of a sample using a reversed-phase HPLC column, in-line or off-line, can be used to increase the efficiency of the ionization process and thus improve sensitivity of detection by mass spectrometry.

A variety of mass analyzers are available that can be paired with different ion sources. Different mass analyzers have different advantages as known to one skilled in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering. This will be of use in tandem mass spectrometry as described further below.

A quadrupole mass analyzer, as well as the other mass analyzers described herein, can be programmed to analyze a defined m/z or mass range. This property of mass spectrometers is useful for the invention described herein. Since the mass range of cleaved tag reporters will be known prior to an assay, a mass spectrometer can be programmed to transmit ions of the projected correct mass range while excluding ions of a higher or lower mass range. The ability to select a mass range can decrease the background noise in the assay and thus increase the signal-to-noise ratio. In addition, a defined mass range can be used to exclude analysis of any un-cleaved or partially-cleaved binding compounds, which would be of higher mass than the mass of the fully-cleaved binding compounds (tag reporters). Therfore, the mass spectrometer can accomplish an inherent separation step as well as detection and identification of the tag reporters.

Ion trap mass spectrometry utilizes an ion trap mass analyzer. In these mass analyzers, fields are applied so that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis is accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. One advantage to ion traps is that they have very high sensitivity, as long as one is careful to limit the number of ions being tapped at one time. Control of the number of ions can be accomplished by varying the time over which ions are injected into the trap. The mass resolution of ion traps is similar to that of quadrupole mass filters, although ion traps do have low m/z limitations.

Time-of-flight mass spectrometry utilizes a time-of-flight mass analyzer. For this method of m/z analysis, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion. One consideration in this type of mass analysis is that the set of ions being studied be introduced into the analyzer at the same time. For example, this type of mass analysis is well suited to ionization techniques like MALDI which produces ions in short well-defined pulses. Another consideration is to control velocity spread produced by ions that have variations in their amounts of kinetic energy. The use of longer flight tubes, ion reflectors, or higher accelerating voltages can help minimize the effects of velocity spread. Time-of-flight mass analyzers have a high level of sensitivity and a wider m/z range than quadrupole or ion trap mass analyzers. Also data can be acquired quickly with this type of mass analyzer because no scanning of the mass analyzer is necessary.

Synthesis of Assay Reagents

Binding compounds for use of the invention are synthesized as disclosed in the following references, which are incorporated herein by reference: International patent publications WO 00/66607; WO 01/83502; WO 02/95356; WO 03/06947; and U.S. Pat. Nos. 6,322,980 and 6,514,700. Exemplary reagents for synthesis of binding compounds are shown in FIGS. 4 A-J. Exemplary synthesis protocols are illustrated in FIGS. 5A-7D.

EXAMPLE 1

PI3K/Her-3 Receptor Activation Complex

Figure 7A:
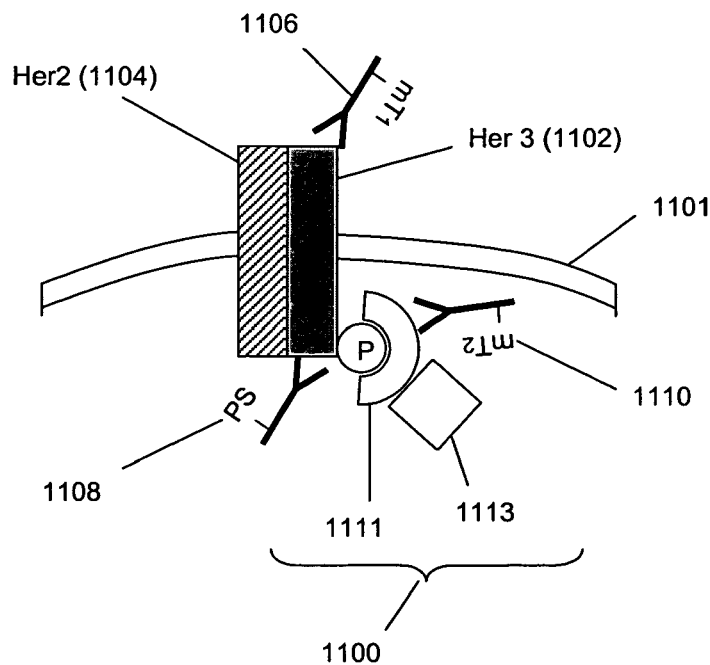
FIGS. 7A-7D illustrate the assay design and experimental results for detecting a PI3 kinase-Her3 receptor activation complex.
Figure 7B:
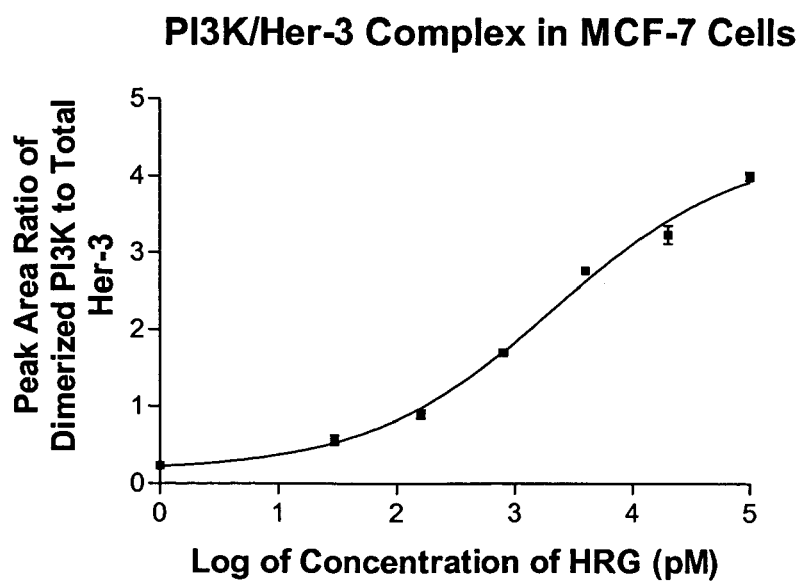
Figure 7C:
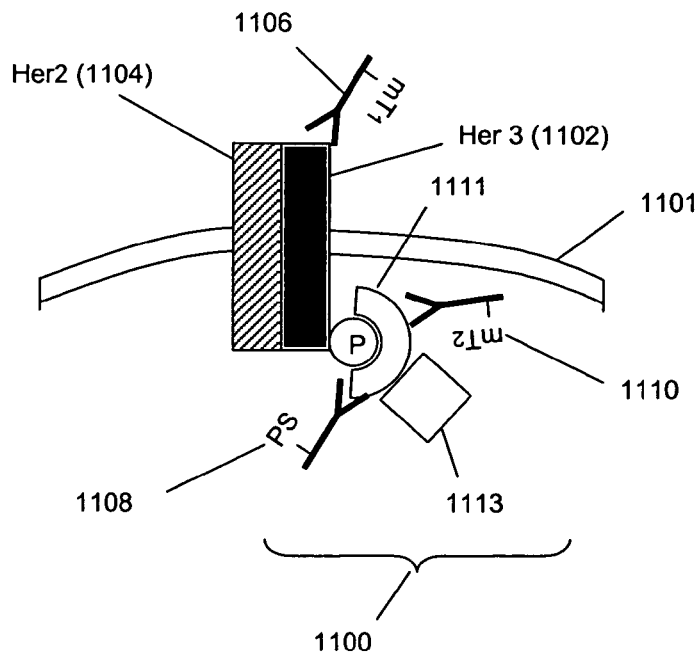
Figure 7D:
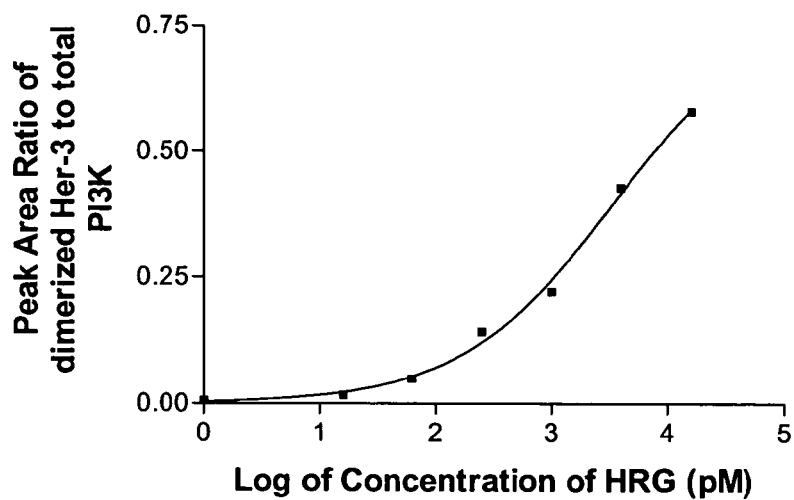

In this example, assays were designed as shown in FIGS. 7A and 7C to measure a receptor complex comprising Her2, Her3, and PI3K in breast cancer cell line, MCF-7. Binding compound (1106) having a first molecular tag ("mT$_1$" in the figure and "eTag1" below) is specific for the extracellular domain of Her3 receptor (1102), binding compound (1110) having a second molecular tag ("mT2" in the figure and "eTag2" below) is specific for the p85 component (1111) of PI3K protein (1100), and cleaving probe (1108) having a photosensitizer attached (is specific for the intracellular domain of Her3 receptor (1102) where "H2" indicates a Her2 receptor (1104), "H3" indicates a Her3 receptor (1102), "p85" and "p110" are components of PI3 kinase (1100), which binds to a phosphorylation site of H3 (denoted by "P") through its p85 moiety. The two assay designs are similar, except that in the design of FIG. 7A the cleaving probe is specific for the Her3 receptor, and in the design of FIG. 7C, the cleaving probe is specific for the p85 component of P13 kinase. The assays were carried out as follows.

Sample Preparation:
1. Serum-starve breast cancer cell line culture overnight before use.
2. Stimulate cell lines with HRG in culture media for 10 minutes at 37° C. Exemplary doses of HRG are 0, 0.032, 0.16, 0.8, 4, 20, 100 nM for MCF-7 cells.
3. Aspirate culture media, transfer onto ice, and add lysis buffer (described above to lyse cells in situ.
4. Scrape and transfer lysate to microfuge tube. Incubate on ice for 30 min. Centrifuge at 14,000 rpm, 4° C., for 10 min.
5. Collect supernatants as lysates and aliquot for storage at −80° C. until use.

| Lysis Buffer (made fresh and stored on ice): | | |
|---|---|---|
| Final | ul | Stock |
| 1% Triton X-100 | 1000 | 10% |
| 20 mM Tris-HCl (pH 7.5) | 200 | 1 M |
| 100 mM NaCl | 200 | 5 M |
| 50 mM NaF | 500 | 1 M |
| 50 mM Na beta-glycerophosphate | 1000 | 0.5 M |
| 1 mM Na$_3$VO$_4$ | 100 | 0.1 M |
| 5 mM EDTA | 100 | 0.5 M |
| ug/ml pepstatin | 100 | 1 mg/ml |
| 1 tablet (per 10 ml) Roche Complete protease inhibitor (#1836170) | N/A | N/A |
| Water | 6500 | N/A |
|  | 10 ml | Total |

Assay design: Receptor complex formation is quantified ratiometrically based on the schematics illustrated in each figure. That is, the readout of the assays are the peak ratios of molecular tags, eTag2/eTag1.

The total assay volume is 40 ul. The lysate volume is adjusted to 10 ul with lysis buffer. The antibodies are diluted in lysis buffer up to 20 ul. Typically ~5000 to 500,000 cell-equivalent of lysates is used per reaction.

Procedure: Working concentrations of pre-mixed antibodies prior to adding into reaction:

For Her-3/PI3K complex with cleaving probe at Her-3 (the design of FIG. 7A)
    eTag1_anti-Her-3 at 10 nM (eTag1 was Pro14 in this assay)
    eTag2_anti-PI3K at 10 nM (eTag2 was Pro1 in this assay)
    Biotin_anti-Her-3 at 20 nM
    Universal Standard US-1 at 700 pM
    [The Universal Standard US-1 is BSA conjugated with biotin and molecular tag Pro8, which is used to normalize the amount of streptavidin-photosensitizer beads in an assay]. The molecular tags were attached directly to antibodies by reacting an NHS-ester of a molecular tag precursor (see FIGS. 4A-4J) with free amines on the antibodies using conventional techniques, e.g. Hermanson (cited above).

For Her-3/PI3K complex with cleaving probe at PI3K (the design of FIG. 7C):
    eTag1_anti-PI3K at 10 nM (eTag1 was Pro1 in this assay)
    eTag2_anti-Her-3 at 10 nM (eTag2 was Pro14 in this assay)
    Biotin_anti-PI3K at 20 nM
    Universal Standard US-1 at 700 nM
1. To assay 96-well filter plate (Millipore MAGVN2250), add 20 ul antibody mix to 10 ul lysate and incubate for 1 hour at 4° C.
2. Add 10 ul streptavidin-derivatized cleaving probe (final 4 ug/well) to assay well and incubate for 40 min.
3. Add 200 ul wash buffer and apply vacuum to empty.
4. Add 30 ul illumination buffer and illuminate.
5. Transfer 10 ul of each reaction to CE assay plate for analysis.

Data Analysis:
1. Normalize relative fluorescence units (RFU) signal of each molecular tag against that of internal Universal Standard US-1.
2. Subtract RFU of "no lysate" background control from corresponding normalized eTag reporter signals.
3. Report receptor complex formation as the ratiometric of normalized eTag2/eTag1 signal (shown in FIGS. 7B and 7D).

EXAMPLE 2

Shc/Her-3 Receptor-Adaptor Interaction

Figure 8A:
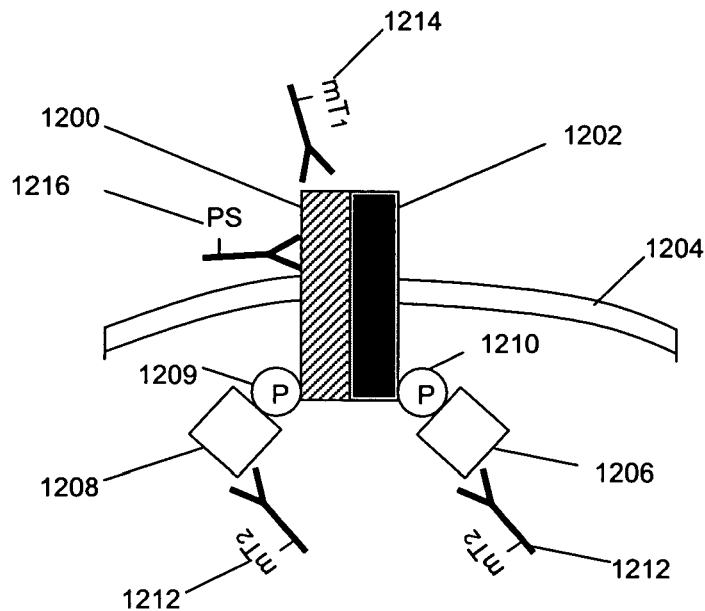
FIGS. 8A-8D illustrate the assay design and experimental results for detecting a Shc/Her3 receptor-adaptor complex.
Figure 8B:
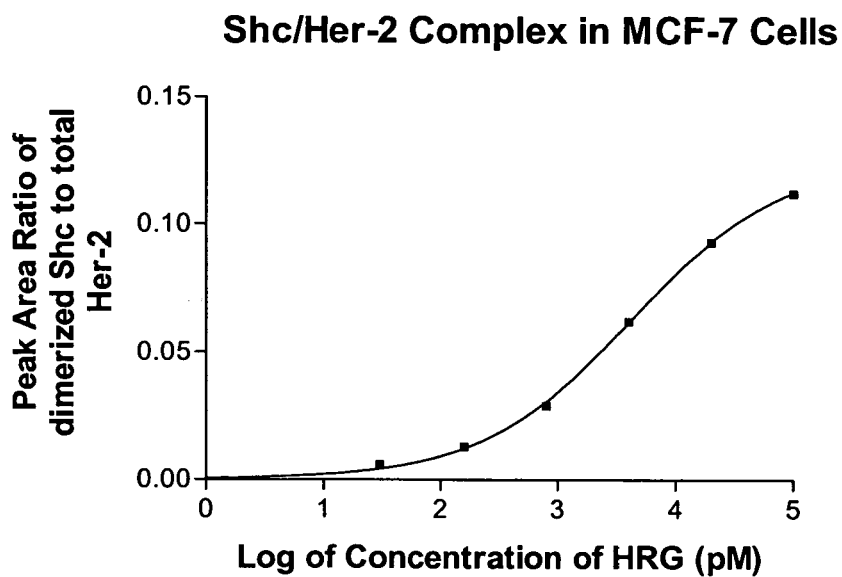
Figure 8C:
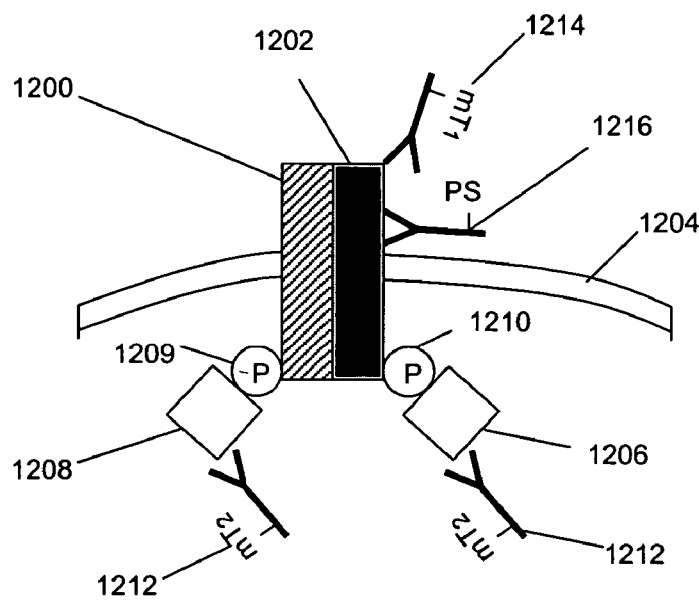

In this example, an assays were designed as shown in FIGS. 8A and 8C. In FIG. 8A, Her2 receptor (1200) and Her3 receptor (1202) form a dimer in cell surface membrane (1204) and each receptor is represented as having phosphorylated sites (1209 and 1210). Shc proteins (1206 and 1208) bind to phosphylation sites (1210) and (1209), respectively. A first binding compound (1214) and cleaving probe (1216) are specific for different antigenic determinants of the extracellular domain of Her2 receptor (1200). A second binding compound (1212) is specific for Shc proteins (1206 and 1208). The assay designs of FIGS. 8A and 8C are similar, except that in the design of FIG. 8A the cleaving probe is specific for the Her2 receptor, and in the design of FIG. 8C, the cleaving probe is specific for the Her3 receptor. Thus, in the former case, total Her2 receptor is measured, whereas in the latter case total Her3 receptor is measured. The assays were carried out as follows. Sample preparation was carried out as above (Example 1).

Figure 8D:
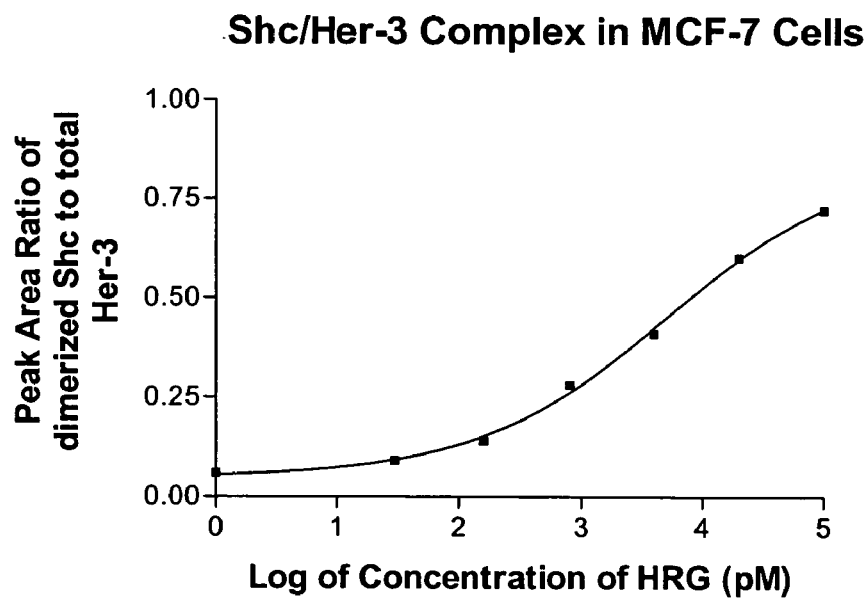

Assay design: Receptor complex formation is quantified ratiometrically based on the schematics illustrated in each figure. That is, in FIGS. 8B and 8D the readout of the assays are the peak ratios of $mT_2/mT_1$ as a function of HRG concentration.

The total assay volume is 40 ul. The lysate volume is adjusted to 10 ul with lysis buffer.

The antibodies are diluted in lysis buffer up to 20 ul. Typically about 5000 to 500,000 cell-equivalent of lysates is used per reaction.

Procedure: Working concentrations of pre-mixed antibodies prior to adding into reaction:
For Her-3/Shc complex with cleaving probe at Her-3 (the design of FIG. 8A):
eTag1_anti-Her-3 at 10 nM (eTag1 was Pro14 in this assay)
eTag2_anti-Shc at 10 nM (eTag2 was Pro12 in this assay)
eTag3_anti-phospho-Tyr at 10 nM (eTag3 was Pro2 in this assay)
Biotin_anti-Her-3 at 20 nM
Universal Standard US-1 at 700 pM
For Her-2/Shc complex with cleaving probe at Her-2 (the design of 8A):
eTag1_anti-Her-2 at 10 nM (eTag1 was Pro14 in this assay)
eTag2_anti-Shc at 10 nM (eTag2 was Pro12 in this assay)
eTag3_anti-phospho-Tyr at 10 nM (eTag3 was Pro2 in this assay)
Biotin_anti-Her-2 at 20 nM
Universal Standard US-1 at 700 pM 1. To assay 96-well filter plate (Millipore MAGVN2250), add 20 ul antibody mix to 10 ul lysate and incubate for 1 hour at 4° C.
2. Add 10 ul streptavidin-derivatized cleaving probe (final 4 ug/well) to assay well and incubate for 40 min.
3. Add 200 ul wash buffer and apply vacuum to empty.
4. Add 30 ul illumination buffer and illuminate.
5. Transfer 10 ul of each reaction to CE assay plate for analysis.

Data Analysis:
1. Normalize relative fluorescence units (RFU) signal of each molecular tag against that of internal Universal Standard US-1.
2. Subtract RFU of "no lysate" background control from corresponding normalized signals for molecular tags.
3. Report receptor complex formation as the ratiometric of normalized $mT_2/mT_1$ signals (shown in FIGS. 8B and 8D) and receptor phosphorylation (data not shown) as $mT_3/mT_1$ signals.

EXAMPLE 3

SHC//Grb2 Protein-Protein Interaction

In this example, an assay was designed as shown in FIG. 1B to detect Grb2//SHC protein-protein complexes in cell lysates. A first binding compound having a first molecular tag was specific for Grb2 and a cleaving probe was provided that was specific for a separate antigenic determinant of Grb2 than that of the first binding compound. A second binding compound specific for SHC having a second molecular tag was also provided. The assays were carried out as follows. Sample preparation was carried out as above.

The total assay volume is 40 ul. The lysate volume is adjusted to 10 ul with lysis buffer.

The antibodies are diluted in lysis buffer up to 20 ul. Typically about 5000 to 500,000 cell-equivalent of lysates is used per reaction.

Procedure: Working concentrations of pre-mixed antibodies prior to adding into reaction:
For Grb2//SHC complex with cleaving probe at Grb2:
eTag1_anti-Grb2 at 10 nM (eTag1 was Pro14 in this assay)
eTag2_anti-SHC at 10 nM (eTag2 was Pro12 in this assay)
Biotin_anti-Grb2 at 20 nM
Universal Standard US-1 at 700 pM
For Grb2/SHC complex with cleaving probe at SHC:
eTag1_anti-Grb2 at 10 nM (eTag1 was Pro14 in this assay)
eTag2_anti-SHC at 10 nM (eTag2 was Pro12 in this assay)
Biotin_anti-SHC at 20 nM
Universal Standard US-1 at 700 pM 1. To assay 96-well filter plate (Millipore MAGVN2250), add 20 ul antibody mix to 10 ul lysate and incubate for 1 hour at 4° C.
2. Add 10 ul streptavidin-derivatized cleaving probe (final 2 ug/well) to assay well and incubate for 40 min.
3. Add 200 ul wash buffer and apply vacuum to empty.
4. Add 50 ul illumination buffer and illuminate.
5. Transfer 20 ul of each reaction to CE assay plate for analysis.

Figure 9:
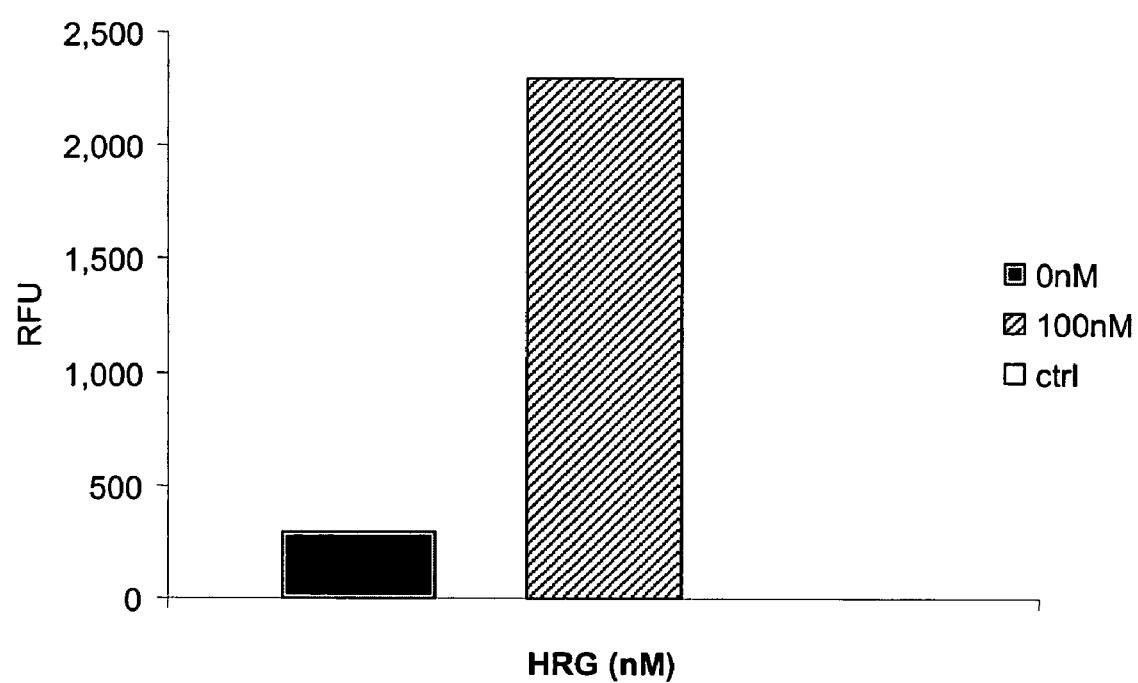
FIG. 9 shows data from assays of Grb2//SHC complexes in lysates of MCF-7 cells.

Data Analysis:
1. Normalize relative fluorescence units (RFU) signal of each molecular tag against that of internal Universal Standard US-1.
2. Subtract RFU of "no lysate" background control from corresponding normalized signals for molecular tags.
3. FIG. 9 shows Grb2//SHC complex formation in MCF-7 cell lysates after stimulation with 0 and 100 nM of heregulin.

EXAMPLE 4

PI3K//IRS-1 Complexes in Cell Line Lysates

Figure 10:
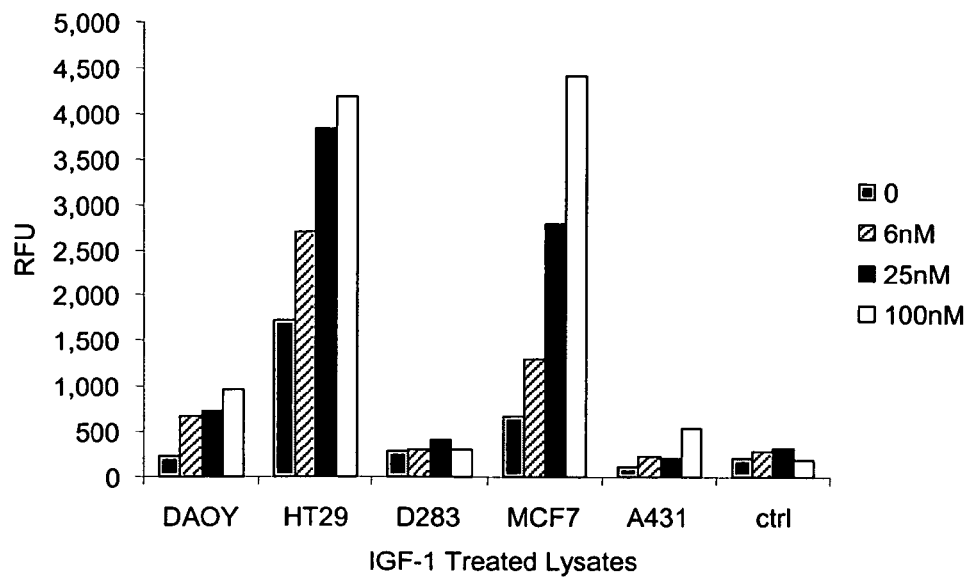
FIG. 10 shows data from assays of IRS-1//PI3K complexes in the lysates of various cell lines after incubation in different concentrations of IGF-1.

In this example, assays to detect PI3K//IRS-1 complexes were performed on the following cell lines: MCF-7, DAOY, HT29, D283, and A431 after each were separately incubated with 0, 6, 25, and 100 nM IGF-1. In the assays, a first binding compound specific for PI3K was provided that had a molecular tag attached, and a cleaving probe specific for IRS-1 was provided, otherwise the assays were carried out using substantially the same procedures as described above. Results of the assays are shown in FIG. 10.

EXAMPLE 5

IGF-1R//IRS-1 Complexes in MCF-7 Lysates

Figure 11:
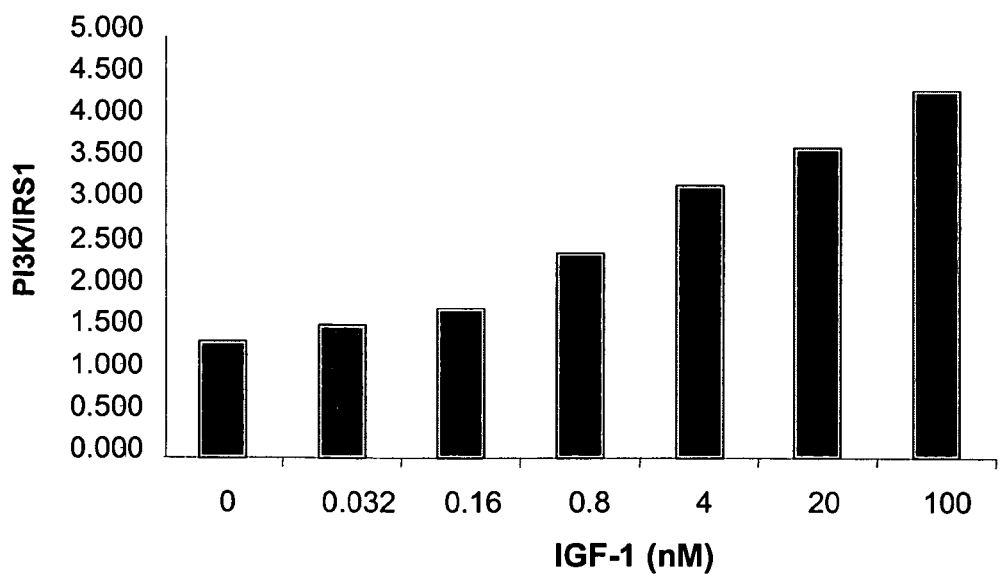
FIG. 11 shows data from assays of IRS-1//PI3K complexes in lysates of MCF-7 cells after incubation in various concentrations of IGF-1.

In this example, an assay was designed as shown in FIGS. 1B to detect IGF-1R//IRS-1 protein-protein complexes in MCF-7 cell lysates after incubation in different concentrations of IGF-1. A first binding compound having a first molecular tag was specific for IRS-1 and a cleaving probe was provided that was specific for a separate antigenic determinant of IRS-1 than that of the first binding compound. A second binding compound specific for IGF-1R having a second molecular tag was also provided. The assays were carried out using substantially the same procedures as described above. Results of the assays are shown in FIG. 11.

EXAMPLE 6

Her3//PI3K Complexes in MCF-7 Lysates

Figure 12:
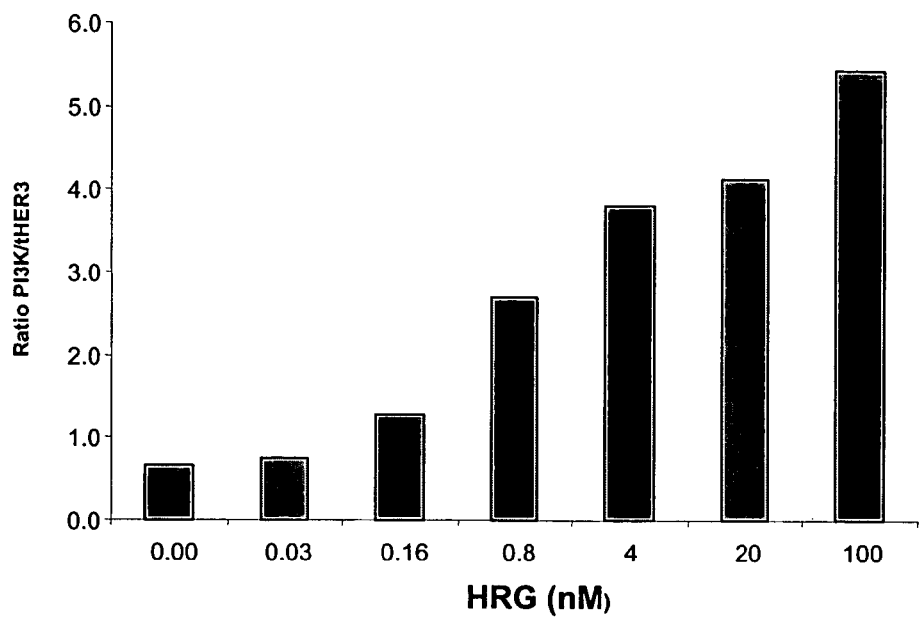
FIG. 12 shows data from assays of Her3//PI3K complexes in lysates of MCF-7 cells after incubation in various concentrations of heregulin.

In this example, an assay was designed as shown in FIGS. 1B to detect Her3//PI3K protein-protein complexes in MCF-7 cell lysates after incubation in different concentrations of heregulin. A first binding compound having a first molecular tag was specific for Her3 and a cleaving probe was provided that was specific for a separate antigenic determinant of Her3 than that of the first binding compound. A second binding compound specific for PI3K having a second molecular tag was also provided. The assays were carried out using substantially the same procedures as described above. Results of the assays are shown in FIG. 12.

EXAMPLE 7

Her3//SHC Complexes in MCF-7 Lysates

Figure 13:
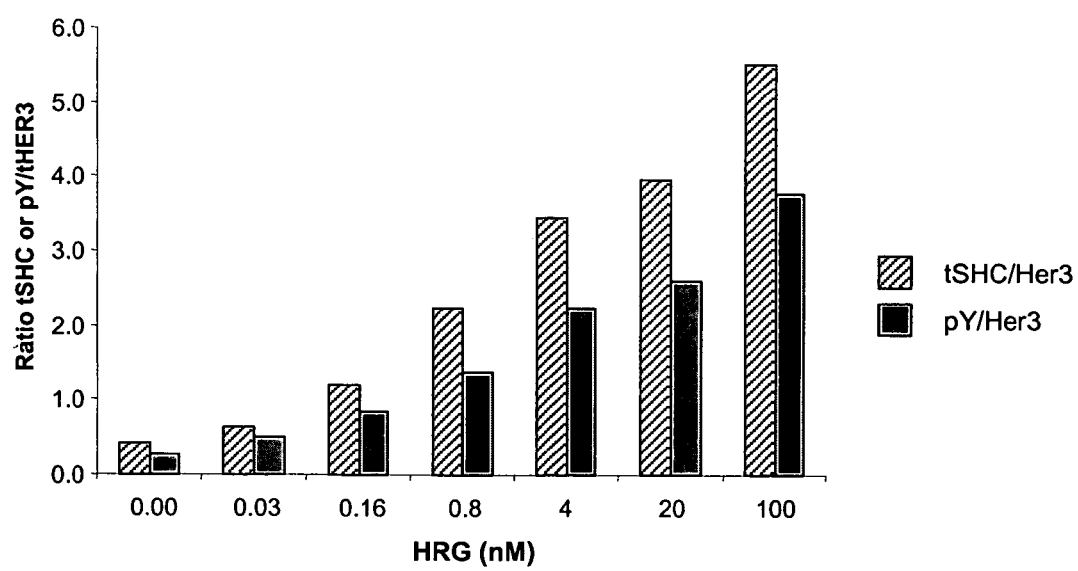
FIG. 13 shows data from assays of Her3//SHC complexes in lysates of MCF-7 cells after incubation in various concentrations of heregulin.

In this example, an assay was designed as shown in FIG. 1B to detect Her3//SHC protein-protein complexes in MCF-7 cell lysates after incubation in different concentrations of heregulin. A first binding compound having a first molecular tag was specific for Her3 and a cleaving probe was provided that was specific for a separate antigenic determinant of Her3 than that of the first binding compound. A second binding compound specific for SHC having a second molecular tag was also provided. The assays were carried out using substantially the same procedures as described above. Results of the assays are shown in FIG. 13.

What is claimed is:

1. A method of detecting one or more complexes comprising a first protein and one or more second proteins, the method comprising the steps of:
    providing for each of the one or more complexes a cleaving probe specific for the first protein in each of the one or more complexes, each cleaving probe comprising a cleavage-inducing moiety;
    providing one or more binding compounds specific for the second protein of each of the one or more complexes, such that each binding compound comprises one or more molecular tags each attached thereto by a cleavable linkage, and such that the one or more molecular tags attached to different binding compounds have different separation characteristics so that upon separation molecular tags from different binding compounds form distinct peaks in a separation profile;
    mixing the cleaving probes, the binding compounds, and the one or more complexes such that cleaving probes specifically bind to first proteins of the complexes and binding compounds specifically bind to the second proteins of the complexes and such that cleavable linkages of the binding compounds are within the effective proximity of cleavage-inducing moieties of the cleaving probes so that molecular tags are released; and
    separating and identifying the released molecular tags to determine the presence or absence or the amount of the one or more complexes of proteins.

2. The method of claim 1 wherein said step of mixing includes generating an active species by said cleavage-inducing moiety, the active species cleaving said cleavable linkages with said effective proximity.

3. The method of claim 2 wherein said cleavage-inducing moiety is a photosensitizer and said active species is singlet oxygen.

4. The method of claim 2 wherein said separation characteristic is electrophoretic mobility and wherein said separation profile is an electropherogram.

5. The method according to claims 1, 2, 3, or 4 wherein said one or more complexes of proteins comprise up to three complexes, and wherein said one or more binding compounds comprise up to three binding compounds.

6. The method of claim 5 wherein each of said cleaving probes and said one or more binding compounds comprises an antibody binding composition.

7. The method of claim 6 wherein said one or more complexes includes a complex comprising a Her3 receptor and a PI3 kinase.

8. The method of claim 7 wherein said Her3 receptor is said first protein whenever said PI3 kinase is said second protein, and wherein said PI3 kinase is said first protein whenever said Her3 receptor is said second protein.

9. The method of claim 6 wherein said one or more complexes include a complex comprising said first protein and said one or more second proteins each selected from the group consisting of a receptor tyrosine kinase, Grb2, SOS, Ras, and Raf, with the proviso that said first protein is different from said one or more second proteins.

10. The method of claim 9 wherein said receptor tyrosine kinase is a human receptor tyrosine kinase selected from the group consisting of Hen, Her2, Her3, Her4, IGF-1R, VEGFR1, VERFR2, PDGFRα, and PDGFRβ.

* * * * *

UNITED STATES PATENT AND TRADEMARK OFFICE
CERTIFICATE OF CORRECTION

PATENT NO. : 7,402,397 B2  Page 1 of 1
APPLICATION NO. : 10/916291
DATED : July 22, 2008
INVENTOR(S) : Po-Ying Chan-Hui et al.

It is certified that error appears in the above-identified patent and that said Letters Patent is hereby corrected as shown below:

Column 46, line 44, delete "Hen" and insert --Her1--.

Signed and Sealed this

Twenty-third Day of September, 2008

JON W. DUDAS
*Director of the United States Patent and Trademark Office*